United States Patent
Pu et al.

(10) Patent No.: US 11,788,072 B2
(45) Date of Patent: Oct. 17, 2023

(54) ACTIVATION OF APC IN IMMUNOTHERAPY

(71) Applicant: Innovative Cellular Therapeutics Holdings, Ltd., Grand Cayman (KY)

(72) Inventors: Chengfei Pu, Shanghai (CN); Lei Xiao, Rockville, MD (US); He Sun, Shanghai (CN); Xiaogang Shen, Shanghai (CN); Cheng Lu, Shanghai (CN)

(73) Assignee: Innovative Cellular Therapeutics Holdings, Ltd., George Town (KY)

( * ) Notice: Subject to any disclaimer, the term of this patent is extended or adjusted under 35 U.S.C. 154(b) by 632 days.

(21) Appl. No.: 16/861,993

(22) Filed: Apr. 29, 2020

(65) Prior Publication Data

US 2020/0347367 A1    Nov. 5, 2020

Related U.S. Application Data

(60) Provisional application No. 62/880,298, filed on Jul. 30, 2019, provisional application No. 62/878,067, filed on Jul. 24, 2019, provisional application No. 62/840,985, filed on Apr. 30, 2019.

(51) Int. Cl.
| | |
|---|---|
| *C12N 9/12* | (2006.01) |
| *C07K 14/725* | (2006.01) |
| *C07K 14/47* | (2006.01) |
| *C07K 16/28* | (2006.01) |
| *A61P 35/00* | (2006.01) |
| *A61K 35/17* | (2015.01) |

(52) U.S. Cl.
CPC ............ *C12N 9/12* (2013.01); *A61K 35/17* (2013.01); *A61P 35/00* (2018.01); *C07K 14/4748* (2013.01); *C07K 14/7051* (2013.01); *C07K 16/2803* (2013.01); *C12Y 207/10001* (2013.01); *C07K 2319/02* (2013.01); *C07K 2319/03* (2013.01); *C07K 2319/30* (2013.01); *C07K 2319/33* (2013.01)

(58) Field of Classification Search
CPC .......... C12N 9/12; A61K 35/17; A61K 38/00; A61K 35/15; A61P 35/00; C07K 14/4748; C07K 14/7051; C07K 16/2803; C07K 2319/02; C07K 2319/03; C07K 2319/30; C07K 2319/33; C07K 2317/622; C07K 2319/00; C12Y 207/10001
See application file for complete search history.

(56) References Cited

U.S. PATENT DOCUMENTS 10,273,281 B2 * 4/2019 Brennan ................ C07K 16/00

FOREIGN PATENT DOCUMENTS

WO    WO 2019/047932    *    3/2019    ......... A61K 39/5156

OTHER PUBLICATIONS

National Library of Medicine—NCBI Reference Sequence: NP_001450. 2—fms-related tyrosine kinase 3 ligand isoform 1 precursor [*Homo sapiens*] (https://www.ncbi.nlm.nih.gov/protein/NP_001450.2).*

* cited by examiner

*Primary Examiner* — Nelson B Moseley, II
(74) *Attorney, Agent, or Firm* — Lee & Hayes, P.C.

(57) ABSTRACT

Embodiments relate to compositions and methods for treating solid tumors. For example, the compositions comprise modified cells comprising an isolated polynucleotide comprising a polynucleotide encoding a nuclear factor of activated T cells (NFAT) promoter operatively associated with a polynucleotide encoding FLT3L.

18 Claims, 12 Drawing Sheets

Specification includes a Sequence Listing.

SEQUENCE LISTING

<160> NUMBER OF SEQ ID NOS: 134

<210> SEQ ID NO 1
<211> LENGTH: 21
<212> TYPE: PRT
<213> ORGANISM: Artificial Sequence
<220> FEATURE:
<223> OTHER INFORMATION: Synthesized

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 69
<212> TYPE: PRT
<213> ORGANISM: Artificial Sequence
<220> FEATURE:
<223> OTHER INFORMATION: Synthesized

<400> SEQUENCE: 2

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr Ile Trp Ala Pro Leu Ala Gly Thr Cys Gly Val Leu Leu Leu
    50                  55                  60

Ser Leu Val Ile Thr
65

<210> SEQ ID NO 3
<211> LENGTH: 42
<212> TYPE: PRT
<213> ORGANISM: Artificial Sequence
<220> FEATURE:
<223> OTHER INFORMATION: Synthesized

<400> SEQUENCE: 3

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 4
<211> LENGTH: 112
<212> TYPE: PRT
<213> ORGANISM: Artificial Sequence
<220> FEATURE:
<223> OTHER INFORMATION: Synthesized

<400> SEQUENCE: 4

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys

```
                35                  40                  45
Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
                100                 105                 110

<210> SEQ ID NO 5
<211> LENGTH: 242
<212> TYPE: PRT
<213> ORGANISM: Artificial Sequence
<220> FEATURE:
<223> OTHER INFORMATION: Synthesized

<400> SEQUENCE: 5

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Lys Tyr
                 20                  25                  30

Leu Asn Trp Tyr Gln Gln Lys Pro Gly Lys Ala Pro Lys Leu Leu Ile
             35                  40                  45

Tyr His Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Tyr
                 85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Gly Ser Glu Val Gln Leu Val Glu
            115                 120                 125

Ser Gly Gly Gly Leu Val Gln Pro Gly Gly Ser Leu Arg Leu Ser Cys
130                 135                 140

Ala Ala Ser Gly Val Ser Leu Pro Asp Tyr Gly Val Ser Trp Val Arg
145                 150                 155                 160

Gln Ala Pro Gly Lys Gly Leu Glu Trp Val Ser Val Ile Trp Gly Ser
                165                 170                 175

Glu Thr Thr Tyr Tyr Asn Ser Ala Leu Lys Ser Arg Phe Thr Ile Ser
            180                 185                 190

Arg Asp Asn Ala Lys Asn Ser Leu Tyr Leu Gln Met Asn Ser Leu Arg
            195                 200                 205

Ala Glu Asp Thr Ala Val Tyr Tyr Cys Ala Lys His Tyr Tyr Tyr Gly
        210                 215                 220

Gly Ser Tyr Ala Met Asp Tyr Trp Gly Gln Gly Thr Leu Val Thr Val
225                 230                 235                 240

Ser Ser

<210> SEQ ID NO 6
<211> LENGTH: 242
<212> TYPE: PRT
<213> ORGANISM: Artificial Sequence
<220> FEATURE:
<223> OTHER INFORMATION: Synthesized
```

<400> SEQUENCE: 6

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
        115                 120                 125

Ser Gly Pro Gly Leu Val Ala Pro Ser Gln Ser Leu Ser Val Thr Cys
130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser
```

<210> SEQ ID NO 7
<211> LENGTH: 237
<212> TYPE: PRT
<213> ORGANISM: Artificial Sequence
<220> FEATURE:
<223> OTHER INFORMATION: Synthesized

<400> SEQUENCE: 7

```
Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu Gly Gly Gly Gly Ser Gly Gly Gly
            100                 105                 110
```

```
Gly Ser Gly Gly Gly Ser Glu Val Gln Leu Gln Gln Ser Gly Ala
            115                 120                 125
Glu Leu Val Lys Pro Gly Ala Ser Val Lys Leu Ser Cys Thr Ala Ser
130                 135                 140
Gly Phe Asn Ile Asn Asp Thr Tyr Met His Trp Val Lys Gln Arg Pro
145                 150                 155                 160
Glu Gln Gly Leu Glu Trp Ile Gly Arg Ile Asp Pro Ala Asn Gly Asn
                165                 170                 175
Thr Lys Tyr Asp Pro Lys Phe Gln Gly Lys Ala Thr Ile Thr Ala Asp
                180                 185                 190
Thr Ser Ser Asn Thr Ala Tyr Leu Gln Leu Ser Ser Leu Thr Ser Glu
                195                 200                 205
Asp Thr Ala Val Tyr Tyr Cys Ala Arg Gly Ala Arg Gly Ser Arg Phe
210                 215                 220
Ala Tyr Trp Gly Gln Gly Thr Leu Val Thr Val Ser Ala
225                 230                 235
```

<210> SEQ ID NO 8
<211> LENGTH: 244
<212> TYPE: PRT
<213> ORGANISM: Artificial Sequence
<220> FEATURE:
<223> OTHER INFORMATION: Synthesized

<400> SEQUENCE: 8

```
Gln Ser Val Leu Thr Gln Pro Pro Ser Val Ser Ala Ala Pro Gly Gln
1               5                   10                  15
Lys Val Thr Ile Ser Cys Ser Gly Ser Ser Ser Asp Ile Gly Ser Asn
                20                  25                  30
Tyr Val Ser Trp Tyr Gln Gln Phe Pro Gly Thr Ala Pro Lys Leu Leu
            35                  40                  45
Ile Tyr Asp Asn Asn Lys Arg Pro Ser Ala Ile Pro Asp Arg Phe Ser
50                  55                  60
Gly Ser Lys Ser Gly Thr Ser Ala Thr Leu Gly Ile Thr Gly Leu Gln
65                  70                  75                  80
Thr Gly Asp Glu Ala Asp Tyr Tyr Cys Gly Thr Trp Asp Ser Arg Leu
                85                  90                  95
Gly Ile Ala Val Phe Gly Gly Gly Thr Gln Leu Thr Val Leu Gly Gly
            100                 105                 110
Gly Gly Ser Gly Gly Gly Gly Ser Gly Gly Gly Gly Ser Glu Val Gln
            115                 120                 125
Leu Val Gln Ser Gly Ala Glu Val Lys Lys Pro Gly Gln Ser Leu Lys
130                 135                 140
Ile Ser Cys Lys Ala Ser Gly Tyr Ser Leu Thr Asp Asn Trp Ile Gly
145                 150                 155                 160
Trp Val Arg Gln Lys Pro Gly Lys Gly Leu Glu Trp Met Gly Ile Ile
                165                 170                 175
Tyr Pro Gly Asp Ser Asp Thr Arg Tyr Ser Pro Ser Phe Gln Gly Gln
                180                 185                 190
Val Thr Ile Ser Ala Asp Lys Ser Ile Asn Thr Ala Tyr Leu Gln Trp
                195                 200                 205
Ser Ser Leu Lys Ala Ser Asp Thr Ala Ile Tyr Tyr Cys Val Gly Leu
            210                 215                 220
Asp Trp Asn Tyr Asn Pro Leu Arg Tyr Trp Gly Pro Gly Thr Leu Val
225                 230                 235                 240
```

<210> SEQ ID NO 9
<211> LENGTH: 252
<212> TYPE: PRT
<213> ORGANISM: Artificial Sequence
<220> FEATURE:
<223> OTHER INFORMATION: Synthesized

<400> SEQUENCE: 9

```
Thr Val Ser Ser

Asp Ile Val Leu Thr Gln Ser Pro Ala Ser Leu Ala Val Ser Leu Gly
1               5                   10                  15

Gln Gly Ala Thr Ile Ser Cys Arg Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Gly
                85                  90                  95

Glu Leu Pro Pro Ser Phe Gly Gly Gly Thr Lys Leu Glu Ile Lys Arg
            100                 105                 110

Ala Gly Gly Gly Gly Ser Gly Gly Gly Gly Ser Gly Gly Gly Gly Ser
        115                 120                 125

Glu Val Gln Leu Val Glu Ser Gly Gly Asp Leu Val Lys Pro Gly Gly
    130                 135                 140

Ser Leu Lys Leu Ser Cys Ala Val Ser Gly Phe Thr Phe Ser Ser Tyr
145                 150                 155                 160

Gly Met Ser Trp Val Arg Gln Thr Pro Asp Lys Arg Leu Glu Trp Val
                165                 170                 175

Ala Thr Val Ser Ser Gly Gly Thr Tyr Thr Tyr Tyr Pro Asp Ser Val
            180                 185                 190

Lys Gly Arg Phe Thr Ile Ser Arg Asp Asn Ala Lys Asn Thr Leu Tyr
        195                 200                 205

Leu Gln Met Ser Ser Leu Lys Ser Glu Asp Ser Ala Met Tyr Tyr Cys
    210                 215                 220

Ala Arg His Arg Gly Asn Tyr Tyr Ala Thr Tyr Tyr Ala Met Asp
225                 230                 235                 240

Tyr Trp Gly Gln Gly Thr Ser Val Thr Val Ser Ser
                245                 250
```

<210> SEQ ID NO 10
<211> LENGTH: 243
<212> TYPE: PRT
<213> ORGANISM: Artificial Sequence
<220> FEATURE:
<223> OTHER INFORMATION: Synthesized

<400> SEQUENCE: 10

```
Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45
```

Tyr Ser Gly Ser Thr Leu Gln Ser Gly Ile Pro Ser Arg Phe Ser Gly
                50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His His Glu Tyr Pro Tyr
                85                  90                  95

Thr Phe Gly Gly Gly Thr Lys Leu Glu Ile Lys Gly Gly Gly Gly Ser
                100                 105                 110

Gly Gly Gly Gly Ser Gly Gly Gly Ser Gln Val Gln Leu Gln Gln
                115                 120                 125

Pro Gly Ala Glu Leu Val Arg Pro Gly Ala Ser Val Lys Leu Ser Cys
                130                 135                 140

Lys Ala Ser Gly Tyr Thr Phe Thr Thr Tyr Trp Met Asn Trp Val Lys
145                 150                 155                 160

Gln Arg Pro Glu Gln Gly Leu Glu Trp Ile Gly Arg Ile Asp Pro Tyr
                165                 170                 175

Asp Ser Glu Thr His Tyr Asn Gln Lys Phe Lys Asp Lys Ala Ile Leu
                180                 185                 190

Thr Val Asp Lys Ser Ser Ser Thr Ala Tyr Met Gln Leu Ser Ser Leu
                195                 200                 205

Thr Ser Glu Asp Ser Ala Val Tyr Tyr Cys Ala Arg Gly Pro Tyr Tyr
                210                 215                 220

Gly Thr Asn Pro Trp Phe Pro Tyr Trp Gly Gln Gly Thr Leu Val Thr
225                 230                 235                 240

Val Ser Ser

<210> SEQ ID NO 11
<211> LENGTH: 241
<212> TYPE: PRT
<213> ORGANISM: Artificial Sequence
<220> FEATURE:
<223> OTHER INFORMATION: Synthesized

<400> SEQUENCE: 11

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Thr Phe Gly Gln Gly Thr Asn Val Glu Ile Lys Gly Gly Gly Gly Ser
                100                 105                 110

Gly Gly Gly Gly Ser Gly Gly Gly Ser Gln Val Gln Leu Gln Gln
                115                 120                 125

Trp Gly Ala Gly Leu Leu Lys Pro Ser Glu Thr Leu Ser Leu Thr Cys
                130                 135                 140

Ala Val Phe Gly Gly Ser Phe Ser Gly Tyr Tyr Trp Ser Trp Ile Arg
145                 150                 155                 160

```
Gln Pro Pro Gly Lys Gly Leu Glu Trp Ile Gly Glu Ile Asn His Arg
            165                 170                 175
Gly Asn Thr Asn Asp Asn Pro Ser Leu Lys Ser Arg Val Thr Ile Ser
        180                 185                 190
Val Asp Thr Ser Lys Asn Gln Phe Ala Leu Lys Leu Ser Ser Val Thr
        195                 200                 205
Ala Ala Asp Thr Ala Val Tyr Tyr Cys Ala Arg Glu Arg Gly Tyr Thr
    210                 215                 220
Tyr Gly Asn Phe Asp His Trp Gly Gln Gly Thr Leu Val Thr Val Ser
225                 230                 235                 240
Ser
```

<210> SEQ ID NO 12
<211> LENGTH: 246
<212> TYPE: PRT
<213> ORGANISM: Artificial Sequence
<220> FEATURE:
<223> OTHER INFORMATION: Synthesized

<400> SEQUENCE: 12

```
Asp Val Val Met Thr Gln Thr Pro Leu Ser Leu Pro Val Arg Leu Gly
1               5                   10                  15
Asp Gln Ala Ser Ile Ser Cys Arg Ser Ser Gln Ser Leu Val His Ser
            20                  25                  30
Asn Gly Asn Thr Tyr Leu His Trp Tyr Leu Gln Lys Pro Gly Gln Ser
        35                  40                  45
Pro Lys Leu Leu Ile Tyr Lys Val Ser Asn Arg Phe Ser Gly Val Pro
    50                  55                  60
Asp Arg Phe Ser Gly Ser Gly Ser Gly Thr Asn Phe Thr Leu Lys Ile
65                  70                  75                  80
Ser Arg Val Glu Ala Glu Asp Leu Gly Leu Tyr Phe Cys Ser Gln Ser
                85                  90                  95
Thr His Val Pro Tyr Thr Phe Gly Gly Gly Thr Lys Leu Glu Ile Lys
            100                 105                 110
Arg Ala Gly Gly Gly Gly Ser Gly Gly Gly Gly Ser Gly Gly Gly Gly
        115                 120                 125
Ser Gln Val Gln Leu Arg Gln Ser Gly Pro Glu Leu Val Lys Pro Gly
130                 135                 140
Ala Ser Val Lys Met Ser Cys Lys Ala Ser Gly Tyr Thr Phe Thr Asp
145                 150                 155                 160
Tyr Val Ile Ser Trp Val Lys Gln Arg Thr Gly Gln Gly Leu Glu Trp
            165                 170                 175
Ile Gly Asp Ile Tyr Pro Gly Ser Gly Tyr Ser Phe Tyr Asn Glu Asn
        180                 185                 190
Phe Lys Gly Lys Ala Thr Leu Thr Ala Asp Lys Ser Ser Thr Thr Ala
    195                 200                 205
Tyr Met Gln Leu Ser Ser Leu Thr Ser Glu Asp Ser Ala Val Tyr Phe
    210                 215                 220
Cys Ala Thr Tyr Tyr Asn Tyr Pro Phe Ala Tyr Trp Gly Gln Gly Thr
225                 230                 235                 240
Leu Val Thr Val Ser Ala
            245
```

<210> SEQ ID NO 13
<211> LENGTH: 199
<212> TYPE: PRT

<213> ORGANISM: Artificial Sequence
<220> FEATURE:
<223> OTHER INFORMATION: Synthesized

<400> SEQUENCE: 13

Leu Pro Ile Cys Pro Gly Gly Ala Ala Arg Cys Gln Val Thr Leu Arg
1               5                   10                  15

Asp Leu Phe Asp Arg Ala Val Val Leu Ser His Tyr Ile His Asn Leu
            20                  25                  30

Ser Ser Glu Met Phe Ser Glu Phe Asp Lys Arg Tyr Thr His Gly Arg
        35                  40                  45

Gly Phe Ile Thr Lys Ala Ile Asn Ser Cys His Thr Ser Ser Leu Ala
    50                  55                  60

Thr Pro Glu Asp Lys Glu Gln Ala Gln Gln Met Asn Gln Lys Asp Phe
65                  70                  75                  80

Leu Ser Leu Ile Val Ser Ile Leu Arg Ser Trp Asn Glu Pro Leu Tyr
                85                  90                  95

His Leu Val Thr Glu Val Arg Gly Met Gln Glu Ala Pro Glu Ala Ile
            100                 105                 110

Leu Ser Lys Ala Val Glu Ile Glu Glu Gln Thr Lys Arg Leu Leu Glu
        115                 120                 125

Gly Met Glu Leu Ile Val Ser Gln Val His Pro Glu Thr Lys Glu Asn
130                 135                 140

Glu Ile Tyr Pro Val Trp Ser Gly Leu Pro Ser Leu Gln Met Ala Asp
145                 150                 155                 160

Glu Glu Ser Arg Leu Ser Ala Tyr Tyr Asn Leu Leu His Cys Leu Arg
                165                 170                 175

Arg Asp Ser His Lys Ile Asp Asn Tyr Leu Lys Leu Leu Lys Cys Arg
            180                 185                 190

Ile Ile His Asn Asn Asn Cys
        195

<210> SEQ ID NO 14
<211> LENGTH: 240
<212> TYPE: PRT
<213> ORGANISM: Artificial Sequence
<220> FEATURE:
<223> OTHER INFORMATION: Synthesized

<400> SEQUENCE: 14

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

Gly Gly Gly Gly Ser Gly Gly Gly Gly Ser Gly Gly Gly Gly Ser
        115                 120                 125

```
Asp Ile Val Met Thr Gln Ser Pro Asp Ser Leu Ala Val Ser Leu Gly
    130                 135                 140

Glu Arg Ala Thr Ile Asn Cys Lys Ser Ser Gln Ser Leu Leu Asn Ser
145                 150                 155                 160

Arg Thr Arg Lys Asn Tyr Leu Ala Trp Tyr Gln Gln Lys Pro Gly Gln
                165                 170                 175

Pro Pro Lys Leu Leu Ile Tyr Trp Ala Ser Thr Arg Glu Ser Gly Val
            180                 185                 190

Pro Asp Arg Phe Ser Gly Ser Gly Ser Gly Thr Asp Phe Thr Leu Thr
        195                 200                 205

Ile Ser Ser Leu Gln Ala Glu Asp Val Ala Val Tyr Tyr Cys Thr Gln
    210                 215                 220

Ser Phe Ile Leu Arg Thr Phe Gly Gln Gly Thr Lys Val Glu Ile Lys
225                 230                 235                 240

<210> SEQ ID NO 15
<211> LENGTH: 281
<212> TYPE: PRT
<213> ORGANISM: Artificial Sequence
<220> FEATURE:
<223> OTHER INFORMATION: Synthesized

<400> SEQUENCE: 15

Met Asn Val Pro Thr Gln Leu Leu Gly Leu Leu Leu Leu Trp Leu Thr
1               5                   10                  15

Gly Gly Lys Cys Asp Ile Gln Met Thr Gln Ser Pro Ala Ser Leu Ser
                20                  25                  30

Ala Ser Leu Glu Glu Ile Val Thr Ile Thr Cys Lys Ala Ser Gln Ala
            35                  40                  45

Ile Asp Ala Tyr Leu Ser Trp Tyr Gln Gln Lys Pro Gly Lys Ser Pro
    50                  55                  60

Gln Leu Leu Ile Tyr Asp Ala Thr Ser Leu Ala Asp Gly Val Pro Ser
65                  70                  75                  80

Arg Phe Ser Gly Ser Arg Ser Gly Thr Gln Tyr Ser Leu Lys Ile Ser
                85                  90                  95

Arg Pro Gln Val Asp Asp Ser Gly Ile Tyr Tyr Cys Leu Gln Ser Tyr
            100                 105                 110

Ser Thr Pro Phe Thr Phe Gly Ser Gly Thr Lys Leu Glu Ile Lys Gly
        115                 120                 125

Gly Gly Gly Gly Ser Gly Gly Gly Ser Gly Gly Gly Ser Met
    130                 135                 140

Ala Val Leu Val Leu Leu Leu Cys Leu Leu Ile Phe Pro Ser Cys Val
145                 150                 155                 160

Leu Ser Gln Val Gln Leu Lys Glu Ser Gly Pro Gly Leu Val Gln Pro
                165                 170                 175

Ser Gln Thr Leu Ser Leu Thr Cys Thr Val Ser Gly Ser Ser Leu Thr
            180                 185                 190

Ser Asn Ser Val Ser Trp Ile Arg Gln Pro Pro Gly Lys Gly Leu Glu
        195                 200                 205

Trp Met Gly Val Ile Trp Ser Asn Gly Asp Ala Asp Tyr Asn Ser Ala
    210                 215                 220

Ile Lys Ser Arg Leu Ser Ile Ser Arg Asp Thr Ser Lys Ser Gln Val
225                 230                 235                 240

Phe Leu Lys Met Asn Ser Leu Gln Thr Glu Asp Thr Ala Met Tyr Phe
                245                 250                 255
```

```
Cys Ala Ser Pro Tyr Tyr Gly Tyr Tyr Phe Pro Phe Asp Tyr Trp Gly
                260                 265                 270

Gln Gly Val Met Val Thr Val Ser Ser
        275                 280
```

<210> SEQ ID NO 16
<211> LENGTH: 285
<212> TYPE: PRT
<213> ORGANISM: Artificial Sequence
<220> FEATURE:
<223> OTHER INFORMATION: Synthesized

<400> SEQUENCE: 16

```
Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Leu Ala Val
            20                  25                  30

Ser Leu Gly Gln Arg Ala Thr Ile Ser Cys Arg Ala Ser Gln Ser Val
        35                  40                  45

Ser Ile Ser Ser His Asp Leu Met Gln Trp Tyr Gln Gln Lys Pro Gly
    50                  55                  60

Gln Gln Pro Lys Leu Leu Ile Tyr Asp Ala Phe Asn Leu Ala Ser Gly
65                  70                  75                  80

Ile Pro Val Arg Phe Ser Gly Ser Gly Ser Gly Thr Asp Phe Thr Leu
                85                  90                  95

Thr Ile Asp Pro Val Gln Ala Asp Asp Ile Ala Thr Tyr Tyr Cys Gln
            100                 105                 110

Gln Ser Lys Asp Asp Pro Tyr Thr Phe Gly Ala Gly Thr Lys Leu Glu
        115                 120                 125

Leu Lys Gly Gly Gly Gly Ser Gly Gly Gly Gly Ser Gly Gly Gly Gly
    130                 135                 140

Gly Ser Met Asp Ile Arg Leu Ser Leu Ala Phe Leu Val Leu Phe Ile
145                 150                 155                 160

Lys Gly Val Gln Cys Glu Val Gln Leu Val Glu Ser Gly Gly Gly Leu
                165                 170                 175

Val Gln Pro Gly Arg Ser Met Lys Leu Ser Cys Ala Ala Ser Gly Phe
            180                 185                 190

Thr Phe Ser Asn Tyr Gly Met Ala Trp Val Arg Gln Ala Pro Thr Lys
        195                 200                 205

Gly Leu Glu Trp Val Ala Thr Ile Ser Tyr Asp Gly Ser Ile Thr Tyr
    210                 215                 220

Tyr Arg Asp Ser Val Lys Gly Arg Phe Thr Ile Ser Arg Asp His Ala
225                 230                 235                 240

Lys Ser Thr Leu Tyr Leu Gln Met Asn Ser Leu Arg Ser Glu Asp Thr
                245                 250                 255

Ala Thr Tyr Tyr Cys Thr Arg Glu Glu Gln Tyr Ser Ser Trp Tyr Phe
            260                 265                 270

Asp Phe Trp Gly Pro Gly Ile Met Val Thr Val Ser Ser
        275                 280                 285
```

<210> SEQ ID NO 17
<211> LENGTH: 242
<212> TYPE: PRT
<213> ORGANISM: Artificial Sequence
<220> FEATURE:
<223> OTHER INFORMATION: Synthesized

<400> SEQUENCE: 17

Asn Ile Val Met Thr Gln Ser Pro Ser Ser Leu Ser Ala Ser Val Gly
1               5                   10                  15

Asp Arg Val Thr Ile Thr Cys Gln Ala Ser Gln Asp Val Gly Thr Ala
            20                  25                  30

Val Ala Trp Tyr Gln Gln Lys Pro Asp Gln Ser Pro Lys Leu Leu Ile
        35                  40                  45

Tyr Trp Thr Ser Thr Arg His Thr Gly Val Pro Asp Arg Phe Thr Gly
50                  55                  60

Ser Gly Ser Gly Thr Asp Phe Thr Leu Thr Ile Ser Ser Leu Gln Pro
65                  70                  75                  80

Glu Asp Ile Ala Thr Tyr Phe Cys His Gln Tyr Asn Ser Tyr Asn Thr
                85                  90                  95

Phe Gly Ser Gly Thr Lys Leu Glu Ile Lys Gly Gly Gly Gly Gly Ser
            100                 105                 110

Gly Gly Gly Gly Ser Gly Gly Gly Ser Gln Val Thr Leu Lys Glu
        115                 120                 125

Ser Gly Pro Val Leu Val Lys Pro Thr Glu Thr Leu Thr Leu Thr Cys
130                 135                 140

Thr Phe Ser Gly Phe Ser Leu Ser Thr Ser Gly Met Gly Val Gly Trp
145                 150                 155                 160

Ile Arg Gln Ala Pro Gly Lys Gly Leu Glu Trp Val Ala His Ile Trp
                165                 170                 175

Trp Asp Asp Asp Val Tyr Tyr Asn Pro Ser Leu Lys Ser Arg Leu Thr
            180                 185                 190

Ile Thr Lys Asp Ala Ser Lys Asp Gln Val Ser Leu Lys Leu Ser Ser
        195                 200                 205

Val Thr Ala Ala Asp Thr Ala Val Tyr Tyr Cys Val Arg Arg Arg Ala
    210                 215                 220

Thr Gly Thr Gly Phe Asp Tyr Trp Gly Gln Gly Thr Leu Val Thr Val
225                 230                 235                 240

Ser Ser

<210> SEQ ID NO 18
<211> LENGTH: 339
<212> TYPE: DNA
<213> ORGANISM: Homo sapiens

<400> SEQUENCE: 18
agagtgaagt tcagcaggag cgcagacgcc cccgcgtacc agcagggcca gaaccagctc      60
tataacgagc tcaatctagg acgaagagag gagtacgatg tttttggacaa gaggcgtggc     120 cgggaccctg agatggggggg aaagccgaga aggaagaacc ctcaggaagg cctgtacaat    180
gaactgcaga aagataagat ggcggaggcc tacagtgaga ttgggatgaa aggcgagcgc     240 cggagggggca aggggcacga tggcctttac cagggtctca gtacagccac caaggacacc    300
tacgacgccc ttcacatgca ggccctgccc cctcgctaa                            339

<210> SEQ ID NO 19
<211> LENGTH: 1689
<212> TYPE: DNA
<213> ORGANISM: Artificial Sequence
<220> FEATURE:
<223> OTHER INFORMATION: Synthesized

<400> SEQUENCE: 19
cggctccggt gcccgtcagt gggcagagcg cacatcgccc acagtccccg agaagttggg      60

-continued

```
gggaggggtc ggcaattgaa ccggtgccta gagaaggtgg cgcggggtaa actgggaaag      120
tgatgtcgtg tactggctcc gccttttcc cgagggtggg ggagaaccgt atataagtgc       180
agtagtcgcc gtgaacgttc ttttcgcaa cgggtttgcc gccagaacac aggatccgcc       240
accatggcct taccagtgac cgccttgctc ctgccgctgg ccttgctgct ccacgccgcc      300
aggccggaca tccagctcac ccagtccccg agctcgctgt ccgcctccgt gggagatcgg      360
gtcaccatca cgtgccgcgc cagccagtcg atttcctcct acctgaactg gtaccaacag      420
aagcccggaa aagcccgaa gcttctcatc tacgccgcct cgagcctgca gtcaggagtg       480
ccctcacggt tctccggctc cggttccggt actgatttca ccctgaccat ttcctccctg      540
caaccggagg acttcgctac ttactactgc cagcagtcgt actccacccc ctacactttc      600
ggacaaggca ccaaggtcga aatcaagggt ggcggtggct cgggcggtgg tgggtcgggt      660
ggcggcggat ctgaagtgca attggtggaa tcaggggag acttgtgca gcctggagga       720 tcgctgagac tgtcatgtgc cgtgtccggc tttgccctgt ccaaccacgg gatgtcctgg      780
gtccgccgcg cgcctggaaa gggcctcgaa tgggtgtcgg gtattgtgta cagcggtagc     840
acctactatg ccgcatccgt gaaggggaga ttcaccatca gccgggacaa ctccaggaac      900
actctgtacc tccaaatgaa ttcgctgagg ccagaggaca ctgccatcta ctactgctcc      960
gcgcatggcg gagagtccga cgtctgggga caggggacca ccgtgaccgt gtctagcacc     1020
acgacgccag cgccgcgacc accaacaccg gcgcccacca tcgcgtcgca gccccctgtcc    1080 ctgcgcccag aggcgtgccg gccagcggcg gggggcgcag tgcacacgag ggggctggac     1140
ttcgcctgtg atatctacat ctgggcgccc ttggccggga cttgtggggt ccttctcctg     1200
tcactggtta tcaccctta ctgcaaacgg ggcagaaaga aactcctgta tatattcaaa      1260 caaccatta tgagaccagt acaaactact caagaggaag atgctgtag ctgccgattt       1320 ccagaagaag aagaaggagg atgtgaactg agagtgaagt tcagcaggag cgcagacgcc     1380
cccgcgtacc agcagggcca gaaccagctc tataacgagc tcaatctagg acgaagagag     1440
gagtacgatg tttggacaa gaggcgtgg cgggaccctg agatggggg aaagccgaga        1500 aggaagaacc ctcaggaagg cctgtacaat gaactgcaga agataagat ggcggaggcc      1560 tacagtgaga ttgggatgaa aggcgagcgc cggaggggca aggggcacga tggcctttac     1620
cagggtctca gtacagccac caaggacacc tacgacgccc ttcacatgca ggccctgccc     1680
cctcgctaa                                                              1689
```

<210> SEQ ID NO 20
<211> LENGTH: 1446
<212> TYPE: DNA
<213> ORGANISM: Artificial Sequence
<220> FEATURE:
<223> OTHER INFORMATION: Synthesized

<400> SEQUENCE: 20

```
atggcctta cagtgaccgc cttgctcctg ccgctggcct tgctgctcca cgccgccagg       60
ccggacatcc agctcaccca gtccccgagc tcgctgtccg cctccgtggg agatcgggtc     120
accatcacgt gccgcgccag ccagtcgatt tcctcctacc tgaactggta ccaacagaag     180
cccggaaaag ccccgaagct tctcatctac gccgcctcga gcctgcagtc aggagtgccc    240
tcacggttct ccggctccgg ttccggtact gatttcaccc tgaccatttc ctccctgcaa    300
ccggaggact tcgctactta ctactgccag cagtcgtact ccacccccta cactttcgga    360
```

| | |
|---|---|
| caaggcacca aggtcgaaat caagggtggc ggtggctcgg gcggtggtgg gtcgggtggc | 420 |
| ggcggatctg aagtgcaatt ggtggaatca gggggaggac ttgtgcagcc tggaggatcg | 480 |
| ctgagactgt catgtgccgt gtccggcttt gccctgtcca accacgggat gtcctgggtc | 540 |
| cgccgcgcgc ctggaaaggg cctcgaatgg gtgtcgggta ttgtgtacag cggtagcacc | 600 |
| tactatgccg catccgtgaa ggggagattc accatcagcc gggacaactc caggaacact | 660 |
| ctgtacctcc aaatgaattc gctgaggcca gaggacactg ccatctacta ctgctccgcg | 720 |
| catggcggag agtccgacgt ctggggacag gggaccaccg tgaccgtgtc tagcaccacg | 780 |
| acgccagcgc cgcgaccacc aacaccggcg cccaccatcg cgtcgcagcc cctgtccctg | 840 |
| cgcccagagg cgtgccggcc agcggcgggg ggcgcagtgc acacgagggg gctggacttc | 900 |
| gcctgtgata tctacatctg ggcgcccttg gccgggactt gtgggtcct tctcctgtca | 960 |
| ctggttatca ccctttactg caaacggggc agaaagaaac tcctgtatat attcaaacaa | 1020 |
| ccatttatga accagtacaa actactcaa gaggaagatg gctgtagctg ccgatttcca | 1080 |
| gaagaagaag aaggaggatg tgaactgaga gtgaagttca gcaggagcgc agacgccccc | 1140 |
| gcgtacaagc agggccagaa ccagctctat aacgagctca atctaggacg aagagaggag | 1200 |
| tacgatgttt tggacaagag gcgtggccgg accctgaga tgggggggaaa gccgagaagg | 1260 |
| aagaaccctc aggaaggcct gtacaatgaa ctgcagaaag ataagatggc ggaggcctac | 1320 |
| agtgagattg ggatgaaagg cgagcgccgg aggggcaagg ggcacgatgg cctttaccag | 1380 |
| ggtctcagta cagccaccaa ggacacctac gacgcccttc acatgcaggc cctgccccct | 1440 |
| cgctaa | 1446 |

<210> SEQ ID NO 21
<211> LENGTH: 1467
<212> TYPE: DNA
<213> ORGANISM: Artificial Sequence
<220> FEATURE:
<223> OTHER INFORMATION: Synthesized

<400> SEQUENCE: 21

| | |
|---|---|
| atggccttac cagtgaccgc cttgctcctg ccgctggcct tgctgctcca cgccgccagg | 60 |
| ccggacatcg tgatgaccca gtcccctcc agcctgacag tgacagccgg cgagaaggtg | 120 |
| acaatgatct gtaagtccag ccagagcctg ctgaacagcg gcgaccagaa gaactacctg | 180 |
| acctggtacc agcagaagcc tggccagccc cccaagctgc tgatcttctg gccagcaca | 240 |
| agggagagcg gcgtgcccga cagattcaca ggcagcggca gcggcaccga cttcacactg | 300 |
| accatttcct ccgtgcaggc cgaggacctc gccgtgtact actgccagaa cgactactcc | 360 |
| tacccctga cattcggcgc cggcaccaaa ctggagctga agggtggcgg tggctcgggc | 420 |
| ggtggtgggt cgggtggcgg cggatctcag gtgcagctcc agcagtccga tgccgagctg | 480 |
| gtgaagcccg gaagcagcgt caagatcagc tgtaaggcct ccggctacac cttcacagac | 540 |
| cacgccatcc actgggtgaa gcagaagccc gagcagggcc tggagtggat cggccacttt | 600 |
| agccccggaa acaccgacat caagtacaac gacaagttca agggcaaggc caccctgacc | 660 |
| gtggacagga gcagcagcac cgcctacatg cagctgaaca gcctgacaag cgaggacagc | 720 |
| gccgtgtact tctgcaagac ctccaccttc ttcttcgact actggggcca gggaaccacc | 780 |
| ctgacagtgt ccagcaccac gacgccagcg ccgcgaccac caacaccggc gcccaccatc | 840 |
| gcgtcgcagc cctgtccct gcgcccagag gcgtgccggc cagcggcggg gggcgcagtg | 900 |
| cacacgaggg ggctggactt cgcctgtgat atctacatct gggcgccctt ggccgggact | 960 |

```
tgtggggtcc ttctcctgtc actggttatc acccttact gcaaacgggg cagaaagaaa    1020
ctcctgtata tattcaaaca accatttatg agaccagtac aaaactactca agaggaagat    1080 ggctgtagct gccgatttcc agaagaagaa gaaggaggat gtgaactgag agtgaagttc    1140
agcaggagcg cagacgcccc cgcgtacaag cagggccaga accagctcta taacgagctc    1200
aatctaggac gaagagagga gtacgatgtt ttggacaaga ggcgtggccg ggaccctgag    1260 atgggggaa agccgagaag gaagaaccct caggaaggcc tgtacaatga actgcagaaa    1320
gataagatgg cggaggccta cagtgagatt gggatgaaag gcgagcgccg gaggggcaag    1380
gggcacgatg gcctttacca gggtctcagt acagccacca aggacaccta cgacgccctt    1440
cacatgcagg ccctgccccc tcgctaa                                        1467
```

<210> SEQ ID NO 22
<211> LENGTH: 3533
<212> TYPE: DNA
<213> ORGANISM: Artificial Sequence
<220> FEATURE:
<223> OTHER INFORMATION: Synthesized

<400> SEQUENCE: 22

```
atggccttac cagtgaccgc cttgctcctg ccgctggcct tgctgctcca cgccgccagg     60
ccggacatcc agatgacaca gactacatcc tccctgtctg cctctctggg agacagagtc    120
accatcagtt gcagggcaag tcaggacatt agtaaatatt taaattggta tcagcagaaa    180
ccagatggaa ctgttaaact cctgatctac catacatcaa gattacactc aggagtccca    240
tcaaggttca gtggcagtgg gtctggaaca gattattctc tcaccattag caacctggag    300
caagaagata ttgccactta cttttgccaa caggtaata cgcttccgta cacgttcgga    360
ggggggacca agctggagat cacaggtggc ggtggctcgg gcggtggtgg gtcgggtggc    420
ggcggatctg aggtgaaact gcaggagtca ggacctggcc tggtggcgcc ctcacagagc    480
ctgtccgtca catgcactgt ctcagggtc tcattacccg actatggtgt aagctggatt    540
cgccagcctc cacgaaggg tctggagtgg ctgggagtaa tatggggtag tgaaaccaca    600
tactataatt cagctctcaa atccagactg accatcatca aggacaactc caagagccaa    660
gttttcttaa aaatgaacag tctgcaaact gatgacacag ccatttacta ctgtgccaaa    720
cattattact acggtggtag ctatgctatg gactactggg gccaaggaac ctcagtcacc    780
gtctcctcaa ccacgacgcc agcgccgcga ccaccaacac cggcgcccac catcgcgtcg    840 cagccctgt cctgcgccc agaggcgtgc cggccagcgg cggggggcgc agtgcacacg    900 aggggctgg acttcgcctg tgatatctac atctgggcgc ccttggccgg acttgtggg    960 gtccttctcc tgtcactggt tatcaccctt actgcaaac ggggcagaaa gaaactcctg    1020
tatatattca acaaccatt tatgagacca gtacaaacta ctcaagagga gatggctgt    1080 agctgccgat tccagaaga agaagaagga ggatgtgaac tgagagtgaa gttcagcagg    1140
agcgcagacg cccccgcgta caagcagggc cagaaccagc tctataacga gctcaatcta    1200
ggacgaagag aggagtacga tgttttggac aagaggcgtg gccgggaccc tgagatgggg    1260
ggaaagccga aggaagaa ccctcaggaa ggcctgtaca atgaactgca gaaagataag    1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc ccctcgcta atctagaggc gcgccctct ccctccccc ccctaacgt    1500
```

| | |
|---|---|
| tactggccga agccgcttgg aataaggccg gtgtgcgttt gtctatatgt tattttccac | 1560 |
| catattgccg tcttttggca atgtgagggc ccggaaacct ggccctgtct tcttgacgag | 1620 |
| cattcctagg ggtctttccc ctctcgccaa aggaatgcaa ggtctgttga atgtcgtgaa | 1680 |
| ggaagcagtt cctctggaag cttcttgaag acaaacaacg tctgtagcga ccctttgcag | 1740 |
| gcagcggaac cccccacctg gcgacaggtg cctctgcggc aaaagccac gtgtataaga | 1800 |
| tacacctgca aaggcggcac aaccccagtg ccacgttgtg agttggatag ttgtggaaag | 1860 |
| agtcaaatgg ctctcctcaa gcgtattcaa caaggggctg aaggatgccc agaaggtacc | 1920 |
| ccattgtatg ggatctgatc tggggcctcg gtacacatgc tttacatgtg tttagtcgag | 1980 |
| gttaaaaaaa cgtctaggcc ccccgaacca cggggacgtg gttttccttt gaaaaacacg | 2040 |
| atgataatat ggccacaacc catatgatgg ccttaccagt gaccgccttg ctcctgccgc | 2100 |
| tggccttgct gctccacgcc gccaggccgg acatcgtgat gacccagtcc ccctccagcc | 2160 |
| tgacagtgac agccggcgag aaggtgacaa tgatctgtaa gtccagccag agcctgctga | 2220 |
| acagcggcga ccagaagaac tacctgacct ggtaccagca gaagcctggc cagcccccca | 2280 |
| agctgctgat cttctgggcc agcacaaggg agagcggcgt gcccgacaga ttcacaggca | 2340 |
| gcggcagcgg caccgacttc acactgacca tttcctccgt gcaggccgag gacctcgccg | 2400 |
| tgtactactg ccagaacgac tactcctacc ccctgacatt cggcgccggc accaaactgg | 2460 |
| agctgaaggg tggcggtggc tcgggcggtg gtgggtcggg tggcggcgga tctcaggtgc | 2520 |
| agctccagca gtccgatgcc gagctggtga agcccggaag cagcgtcaag atcagctgta | 2580 |
| aggcctccgg ctacaccttc acagaccacg ccatccactg ggtgaagcag aagcccgagc | 2640 |
| agggcctgga gtggatcggc cactttagcc ccggaaacac cgacatcaag tacaacgaca | 2700 |
| agttcaaggg caaggccacc ctgaccgtgg acaggagcag cagcaccgcc tacatgcagc | 2760 |
| tgaacagcct gacaagcgag gacagcgccg tgtacttctg caagacctcc accttcttct | 2820 |
| cgactactg gggccaggga accaccctga cagtgtccag caccacgacg ccagcgccgc | 2880 |
| gaccaccaac accggcgccc accatcgcgt cgcagcccct gtccctgcgc ccagaggcgt | 2940 |
| gccggccagc ggcgggggc gcagtgcaca cgaggggct ggacttcgcc tgtgatatct | 3000 |
| acatctgggc gcccttggcc gggacttgtg gggtccttct cctgtcactg gttatcaccc | 3060 |
| tttactgcaa acggggcaga aagaaactcc tgtatatatt caaacaacca tttatgagac | 3120 |
| cagtacaaac tactcaagag gaagatggct gtagctgccg atttccagaa gaagaagaag | 3180 |
| gaggatgtga actgagagtg aagttcagca ggagcgcaga cgcccccgcg tacaagcagg | 3240 |
| gccagaacca gctctataac gagctcaatc taggacgaag agaggagtac gatgtttgg | 3300 |
| acaagaggcg tggccgggac cctgagatgg ggaaagcc gagaaggaag aaccctcagg | 3360 |
| aaggcctgta caatgaactg cagaaagata agatggcgga ggcctacagt gagattggga | 3420 |
| tgaaaggcga gcgccggagg ggcaaggggc acgatggcct ttaccagggt ctcagtacag | 3480 |
| ccaccaagga cacctacgac gcccttcaca tgcaggccct gccccctcgc taa | 3533 |

<210> SEQ ID NO 23
<211> LENGTH: 3533
<212> TYPE: DNA
<213> ORGANISM: Artificial Sequence
<220> FEATURE:
<223> OTHER INFORMATION: Synthesized

<400> SEQUENCE: 23

| | |
|---|---|
| atggccttac cagtgaccgc cttgctcctg ccgctggcct tgctgctcca cgccgccagg | 60 |

| | |
|---|---|
| ccggatatcc agatgaccca gagcccgagc agcctgagcg cgagcgtggg tgatcgcgtg | 120 |
| accattacct gcagggcaag tcaggacatt agtaaatatt taaattggta tcagcagaaa | 180 |
| ccgggtaaag cgccgaaact gttaatttat catacatcaa gattacactc aggcgtgccg | 240 |
| tcgcgtttta gcggctcggg ttcgggcacc gattttaccc tgaccatctc gagcttgcag | 300 |
| ccggaggact tcgccaccta ctattgccaa cagggtaata cgcttccgta cacgttcggt | 360 |
| cagggcacca aagtggagat caaaggtggc ggtggctcgg cggtggtggg tcgggtggc | 420 |
| ggcggatctg aggtgcagct ggtggagtct gggggaggct tggtacagcc tggggggtcc | 480 |
| ctgagactct cctgtgcagc ctctggagtg tccctgcctg attatggcgt gtcctgggtc | 540 |
| cgccaggctc cagggaaggg gctggagtgg gtttcagtga tctgggcag cgagacaacc | 600 |
| tactacaaca cgcccctgaa gtcccgattc accatctcca gagacaatgc caagaactca | 660 |
| ctgtatctgc aaatgaacag cctgagagcc gaggacacgg ctgtgtatta ctgtgcgaag | 720 |
| cactactact acgcggcag ctacgctatg gactactggg gccaaggaac cctggtcacc | 780 |
| gtgtcctcaa ccacgacgcc agcgccgcga ccaccaacac cggcgcccac catcgcgtcg | 840 |
| cagcccctgt ccctgcgccc agaggcgtgc cggccagcgg cggggggcgc agtgcacacg | 900 |
| aggggggctgg acttcgcctg tgatatctac atctgggcgc ccttggccgg gacttgtggg | 960 |
| gtccttctcc tgtcactggt tatcaccctt tactgcaaac ggggcagaaa gaaactcctg | 1020 |
| tatatattca acaaccatt tatgagacca gtacaaacta ctcaagagga gatggctgt | 1080 |
| agctgccgat ttccagaaga agaagaagga ggatgtgaac tgagagtgaa gttcagcagg | 1140 |
| agcgcagacg cccccgcgta caagcagggc cagaaccagc tctataacga gctcaatcta | 1200 |
| ggacgaagag aggagtacga tgttttggac aagaggcgtg gccggaccc tgagatgggg | 1260 |
| ggaaagccga aaggaagaa ccctcaggaa ggcctgtaca tgaactgca gaaagataag | 1320 |
| atggcggagg cctacagtga gattgggatg aaaggcgagc gccggagggg caaggggcac | 1380 |
| gatggccttt accagggtct cagtacagcc accaaggaca cctacgacgc ccttcacatg | 1440 |
| caggccctgc cccctcgcta atctagaggc gcgcccctct ccctcccccc ccctaacgt | 1500 |
| tactggccga agccgcttgg aataaggccg gtgtgcgttt gtctatatgt tattttccac | 1560 |
| catattgccg tcttttggca atgtgagggc ccggaaacct ggccctgtct tcttgacgag | 1620 |
| cattcctagg ggtcttcc ctctcgccaa aggaatgcaa ggtctgttga atgtcgtgaa | 1680 |
| ggaagcagtt cctctggaag cttcttgaag acaaacaacg tctgtagcga ccctttgcag | 1740 |
| gcagcggaac cccccacctg gcgacaggtg cctctgcggc caaaagccac gtgtataaga | 1800 |
| tacacctgca aaggcggcac aaccccagtg ccacgttgtg agttggatag ttgtggaaag | 1860 |
| agtcaaatgg ctctcctcaa gcgtattcaa caaggggctg aaggatgccc agaaggtacc | 1920 |
| ccattgtatg ggatctgatc tggggcctcg gtacacatgc tttacatgtg tttagtcgag | 1980 |
| gttaaaaaaa cgtctaggcc ccccgaacca cgggacgtg gttttccttt gaaaaacacg | 2040 |
| atgataatat ggccacaacc catatgatgg ccttaccagt gaccgccttg ctcctgccgc | 2100 |
| tggccttgct gctccacgcc gccaggccgg acatcgtgat gacccagtcc ccctccagcc | 2160 |
| tgacagtgac agcggcgag aaggtgacaa tgatctgtaa gtccagccag agcctgctga | 2220 |
| acagcggcga ccagaagaac tacctgacct ggtaccagca gaagcctggc cagcccccca | 2280 |
| agctgctgat cttctgggcc agcacaaggg agagcggcgt gcccgacaga ttcacaggca | 2340 |
| gcggcagcgg caccgacttc acactgacca tttcctccgt gcaggccgag gacctcgccg | 2400 |

```
tgtactactg ccagaacgac tactcctacc ccctgacatt cggcgccggc accaaactgg      2460
agctgaaggg tggcggtggc tcgggcggtg gtgggtcggg tggcggcgga tctcaggtgc      2520
agctccagca gtccgatgcc gagctggtga agcccggaag cagcgtcaag atcagctgta      2580
aggcctccgg ctacaccttc acagaccacg ccatccactg ggtgaagcag aagcccgagc      2640
agggcctgga gtggatcggc cactttagcc ccggaaacac cgacatcaag tacaacgaca      2700
agttcaaggg caaggccacc ctgaccgtgg acaggagcag cagcaccgcc tacatgcagc      2760
tgaacagcct gacaagcgag gacagcgccg tgtacttctg caagacctcc accttcttct      2820
tcgactactg gggccaggga accacccctga cagtgtccag caccacgacg ccagcgccgc      2880
gaccaccaac accggcgccc accatcgcgt cgcagcccct gtccctgcgc ccagaggcgt      2940
gccggccagc ggcgggggc gcagtgcaca cgagggggct ggacttcgcc tgtgatatct      3000
acatctgggc gcccttggcc gggacttgtg gggtccttct cctgtcactg gttatcaccc      3060
tttactgcaa acgggcaga aagaaactcc tgtatatatt caacaaccca tttatgagac      3120
cagtacaaac tactcaagag gaagatggct gtagctgccg atttccagaa gaagaagaag      3180
gaggatgtga actgagagtg aagttcagca ggagcgcaga cgcccccgcg tacaagcagg      3240
gccagaacca gctctataac gagctcaatc taggacgaag agaggagtac gatgttttgg      3300
acaagaggcg tggccgggac cctgagatgg ggggaaagcc gagaaggaag aaccctcagg      3360
aaggcctgta caatgaactg cagaaagata agatggcgga ggcctacagt gagattggga      3420
tgaaaggcga gcgccggagg ggcaagggc acgatggcct ttaccagggt ctcagtacag      3480
ccaccaagga cacctacgac gcccttcaca tgcaggccct gccccctcgc taa             3533
```

<210> SEQ ID NO 24
<211> LENGTH: 3545
<212> TYPE: DNA
<213> ORGANISM: Artificial Sequence
<220> FEATURE:
<223> OTHER INFORMATION: Synthesized

<400> SEQUENCE: 24

```
atggccttac cagtgaccgc cttgctcctg ccgctggcct tgctgctcca cgccgccagg        60
ccggatatcc agatgaccca gagcccaagc tccctgtccg cctctgtggg cgacagggtg       120
accatcacat gccgcgccag ccagacaatc tggtcctacc tgaactgta tcagcagaga       180 cccggcaagg cccctaatct gctgatctac gcagcatcta gcctgcagtc tggagtgccc       240
tcccggttct ctggaagagg atccggaacc gacttcaccc tgacaatctc ctctctgcag       300
gccgaggact tcgccacata ctattgccag cagagctatt ccatccctca gacctttggc       360
cagggcacaa agctggagat caagggcggc ggcggctctg gaggaggagg aagcggagga       420
ggaggatccc aggtgcagct gcagcagagc ggaccaggac tggtgaagcc ctcccagacc       480
ctgtctctga catgtgccat cagcggcgat tccgtgagct ccaacagcgc cgcctggaat       540
tggatccggc agtctcccag cagaggactg gagtggctgg aaggaccta ctatcgctcc       600 aagtggtaca cgattatgc cgtgtctgtg aagagccgga tcaccatcaa ccctgacaca       660
tctaagaatc agttcagcct gcagctgaat tccgtgaccc cagaggacac agccgtgtac       720
tattgtgcaa gggaggtgac cggcgacctg gaggatgcct ttgacatctg ggccagggc       780 accatggtga cagtgtctag caccacgacg ccagcgccgc gaccaccaac accggcgccc       840
accatcgcgt cgcagcccct gtccctgcgc ccagaggcgt gccggccagc ggcgggggc       900 gcagtgcaca cgagggggct ggacttcgcc tgtgatatct acatctgggc gcccttggcc       960
```

```
gggacttgtg gggtccttct cctgtcactg gttatcaccc tttactgcaa acggggcaga   1020
aagaaactcc tgtatatatt caaacaacca tttatgagac cagtacaaac tactcaagag   1080
gaagatggct gtagctgccg atttccagaa gaagaagaag gaggatgtga actgagagtg   1140
aagttcagca ggagcgcaga cgcccccgcg tacaagcagg ccagaaccag ctctataac   1200
gagctcaatc taggacgaag agaggagtac gatgttttgg acaagaggcg tggccgggac   1260
cctgagatgg ggggaaagcc gagaaggaag aaccctcagg aaggcctgta caatgaactg   1320
cagaaagata agatggcgga ggcctacagt gagattggga tgaaaggcga gcgccggagg   1380
ggcaaggggc acgatggcct ttaccagggt ctcagtacag ccaccaagga cacctacgac   1440
gcccttcaca tgcaggccct gcccctcgc taatctagag gcgcgcccct ctccctcccc   1500
ccccctaac gttactggcc gaagccgctt ggaataaggc cggtgtgcgt ttgtctatat   1560
gttattttcc accatattgc cgtcttttgg caatgtgagg gcccggaaac ctggccctgt   1620
cttcttgacg agcattccta ggggtctttc ccctctcgcc aaaggaatgc aaggtctgtt   1680
gaatgtcgtg aaggaagcag ttcctctgga agcttcttga agacaaacaa cgtctgtagc   1740
gacccttgc aggcagcgga accccccacc tggcgacagg tgcctctgcg gccaaaagcc   1800
acgtgtataa gatacacctg caaaggcggc acaacccag tgccacgttg tgagttggat   1860
agttgtggaa agagtcaaat ggctctcctc aagcgtattc aacaaggggc tgaaggatgc   1920
ccagaaggta ccccattgta tgggatctga tctggggcct cggtacacat gctttacatg   1980
tgtttagtcg aggttaaaaa aacgtctagg cccccccgaac cacggggacg tggttttcct   2040
ttgaaaaaca cgatgataat atggccacaa cccatatgat ggccttacca gtgaccgcct   2100
tgctcctgcc gctggccttg ctgctccacg ccgccaggcc ggacatcgtg atgacccagt   2160
ccccctccag cctgacagtg acagccggcg agaaggtgac aatgatctgt aagtccagcc   2220
agagcctgct gaacagcggc gaccagaaga ctacctgac ctggtaccag cagaagcctg   2280
gccagccccc caagctgctg atcttctggg ccagcacaag ggagagcggc gtgcccgaca   2340
gattcacagg cagcggcagc ggcaccgact tcacactgac catttcctcc gtgcaggccg   2400
aggacctcgc cgtgtactac tgccagaacg actactccta cccccctgaca ttcggcgccg   2460
gcaccaaact ggagctgaag ggtggcggtg gctcgggcgg tggtgggtcg ggtggcggcg   2520
gatctcaggt gcagctccag cagtccgatg ccgagctggt gaagcccgga agcagcgtca   2580
agatcagctg taaggcctcc ggctacacct tcacagacca cgccatccac tgggtgaagc   2640
agaagcccga gcagggcctg gagtggatcg gccactttag ccccggaaac accgacatca   2700
agtacaacga caagttcaag ggcaaggcca ccctgaccgt ggacaggagc agcagcaccg   2760
cctacatgca gctgaacagc ctgacaagcg aggacagcgc cgtgtacttc tgcaagacct   2820
ccaccttctt cttcgactac tggggccagg gaaccaccct gacagtgtcc agcaccacga   2880
cgccagcgcc gcgaccacca caccggcgcg ccaccatcgc gtcgcagccc ctgtccctgc   2940
gcccagaggc gtgccggcca cggcgggggg cgcagtgcac acgagggggg ctggacttcg   3000
cctgtgatat ctacatctgg gcgcccttgg ccgggacttg tggggtcctt ctcctgtcac   3060
tggttatcac cctttactgc aaacggggca gaaagaaact cctgtatata ttcaaacaac   3120
catttatgag accagtacaa actactcaag aggaagatgg ctgtagctgc cgatttccag   3180
aagaagaaga aggaggatgt gaactgagag tgaagttcag caggagcgca gacgcccccg   3240
cgtacaagca gggccagaac cagctctata acgagctcaa tctaggacga agagaggagt   3300
```

| | |
|---|---:|
| acgatgtttt ggacaagagg cgtggccggg accctgagat gggggaaaag ccgagaagga | 3360 |
| agaaccctca ggaaggcctg tacaatgaac tgcagaaaga taagatgcg gaggcctaca | 3420 |
| gtgagattgg gatgaaaggc gagcgccgga ggggcaaggg cacgatggc ctttaccagg | 3480 |
| gtctcagtac agccaccaag gacacctacg acgcccttca catgcaggcc ctgccccctc | 3540 |
| gctaa | 3545 |

<210> SEQ ID NO 25
<211> LENGTH: 3518
<212> TYPE: DNA
<213> ORGANISM: Artificial Sequence
<220> FEATURE:
<223> OTHER INFORMATION: Synthesized

<400> SEQUENCE: 25

| | |
|---|---:|
| atggccttac cagtgaccgc cttgctcctg ccgctggcct tgctgctcca cgccgccagg | 60 |
| ccggacatcc agctcaccca gtccccgagc tcgctgtccg cctccgtggg agatcgggtc | 120 |
| accatcacgt gccgcgccag ccagtcgatt cctcctacc tgaactggta ccaacagaag | 180 |
| cccggaaaag ccccgaagct tctcatctac gccgcctcga gctgcagtc aggagtgccc | 240 |
| tcacggttct ccggctccgg ttccggtact gatttcaccc tgaccatttc ctccctgcaa | 300 |
| ccggaggact cgctactta ctactgccag cagtcgtact ccaccccta cactttcgga | 360 |
| caaggcacca aggtcgaaat caagggtggc ggtggctcgg gcgtggtgg gtcgggtggc | 420 |
| ggcggatctg aagtgcaatt ggtggaatca ggggaggac ttgtgcagcc tggaggatcg | 480 |
| ctgagactgt catgtgccgt gtccggcttt gccctgtcca accacgggat gtcctgggtc | 540 |
| cgccgcgcgc ctggaaaggg cctcgaatgg gtgtcgggta ttgtgtacag cggtagcacc | 600 |
| tactatgccg catccgtgaa ggggagattc accatcagcc gggacaactc caggaacact | 660 |
| ctgtacctcc aaatgaattc gctgaggcca gaggacactg ccatctacta ctgctccgcg | 720 |
| catgcgggag agtccgacgt ctggggacag gggaccaccg tgaccgtgtc tagcaccacg | 780 |
| acgccagcgc cgcgaccacc aacaccggcg cccaccatcg cgtcgcagcc cctgtccctg | 840 |
| cgcccagagg cgtgccggcc agcggcgggg gcgcagtgc acacgagggg gctggacttc | 900 |
| gcctgtgata tctacatctg ggcgcccttg gccgggactt gtggggtcct tctcctgtca | 960 |
| ctggttatca ccctttactg caaacggggc agaaagaaac tcctgtatat attcaaacaa | 1020 |
| ccatttatga ccagtacaa actactcaa gaggaagatg gctgtagctg ccgatttcca | 1080 |
| gaagaagaag aaggaggatg tgaactgaga gtgaagttca gcaggagcgc agacgccccc | 1140 |
| gcgtacaagc agggccagaa ccagctctat aacgagctca atctaggacg aagagaggag | 1200 |
| tacgatgttt tggacaagag gcgtggccgg gaccctgaga tgggggaaa gccgagaagg | 1260 |
| aagaaccctc aggaaggcct gtacaatgaa ctgcagaaag ataagatggc ggaggcctac | 1320 |
| agtgagattg gatgaaagg cgagcgccgg agggcaagg gcacgatgg cctttaccag | 1380 |
| ggtctcagta cagccaccaa ggacacctac gacgcccttc acatgcaggc cctgccccct | 1440 |
| cgctaatcta gaggcgcgcc cctctccctc ccccccccct aacgttactg gccgaagccg | 1500 |
| cttggaataa ggccggtgtg cgtttgtcta tatgttattt tccaccatat tgccgtcttt | 1560 |
| tggcaatgtg agggcccgga aacctggccc tgtcttcttg acgagcattc ctaggggtct | 1620 |
| ttcccctctc gccaaaggaa tgcaaggtct gttgaatgtc gtgaaggaag cagttcctct | 1680 |
| ggaagcttct tgaagacaaa caacgtctgt agcgacccc tgcaggcagc ggaaccccc | 1740 |
| acctggcgac aggtgcctct gcggccaaaa gccacgtgta agatacac ctgcaaaggc | 1800 |

```
ggcacaaccc cagtgccacg ttgtgagttg gatagttgtg gaaagagtca aatggctctc    1860
ctcaagcgta ttcaacaagg ggctgaagga tgcccagaag gtaccccatt gtatgggatc    1920
tgatctgggg cctcggtaca catgctttac atgtgtttag tcgaggttaa aaaaacgtct    1980 aggcccccg aaccacgggg acgtggtttt cctttgaaaa acacgatgat aatatggcca    2040
caacccatat gatggcctta ccagtgaccg ccttgctcct gccgctggcc ttgctgctcc    2100
acgccgccag gccggacatc gtgatgaccc agtcccctc cagcctgaca gtgacagccg    2160
gcgagaaggt gacaatgatc tgtaagtcca gccagagcct gctgaacagc ggcgaccaga    2220
agaactacct gacctggtac cagcagaagc ctggccagcc ccccaagctg ctgatcttct    2280
gggccagcac aagggagagc ggcgtgcccg acagattcac aggcagcggc agcggcaccg    2340
acttcacact gaccatttcc tccgtgcagg ccgaggacct cgccgtgtac tactgccaga    2400
acgactactc ctaccccctg acattcggcg ccggcaccaa actggagctg aagggtggcg    2460
gtggctcggg cggtggtggg tcgggtggcg gcggatctca ggtgcagctc cagcagtccg    2520
atgccgagct ggtgaagccc ggaagcagcg tcaagatcag ctgtaaggcc tccggctaca    2580
ccttcacaga ccacgccatc cactgggtga agcagaagcc cgagcagggc ctggagtgga    2640
tcggccactt tagccccgga aacaccgaca tcaagtacaa cgacaagttc aagggcaagg    2700
ccaccctgac cgtggacagg agcagcagca ccgcctacat gcagctgaac agcctgacaa    2760
gcgaggacag cgccgtgtac ttctgcaaga cctccacctt cttcttcgac tactggggcc    2820
agggaaccac cctgacagtg tccagcacca cgacgccagc gccgcgacca ccaacaccgg    2880
cgcccaccat cgcgtcgcag cccctgtccc tgcgcccaga ggcgtgccgg ccagcggcgg    2940
ggggcgcagt gcacacgagg gggctggact tcgcctgtga tatctacatc tgggcgccct    3000
tggccgggac ttgtggggtc cttctcctgt cactggttat cacccttac tgcaaacggg    3060 gcagaaagaa actcctgtat atattcaaac aaccatttat gagaccagta caaactactc    3120
aagaggaaga tggctgtagc tgccgatttc cagaagaaga agaaggagga tgtgaactga    3180
gagtgaagtt cagcaggagc gcagacgccc ccgcgtacaa gcagggccag aaccagctct    3240
ataacgagct caatctagga cgaagagagg agtacgatgt tttggacaag aggcgtggcc    3300
gggaccctga tgggggga aagccgagaa ggaagaaccc tcaggaaggc ctgtacaatg    3360
aactgcagaa agataagatg gcggaggcct acagtgagat tgggatgaaa ggcgagcgcc    3420
ggaggggcaa ggggcacgat ggcctttacc agggtctcag tacagccacc aaggacacct    3480
acgacgcccT tcacatgcag gccctgcccc ctcgctaa                            3518
```

<210> SEQ ID NO 26
<211> LENGTH: 2994
<212> TYPE: DNA
<213> ORGANISM: Artificial Sequence
<220> FEATURE:
<223> OTHER INFORMATION: Synthesized

<400> SEQUENCE: 26

```
atggcctac cagtgaccgc cttgctcctg ccgctggcct tgctgctcca cgccgccagg      60
ccggacatcc agatgacaca gactacatcc tccctgtctg cctctctggg agacagagtc    120
accatcagtt gcagggcaag tcaggacatt agtaaatatt taaattggta tcagcagaaa    180
ccagatggaa ctgttaaact cctgatctac catacatcaa gattacactc aggagtccca    240
tcaaggttca gtggcagtgg gtctggaaca gattattctc tcaccattag caacctggag    300
```

```
caagaagata ttgccactta cttttgccaa cagggtaata cgcttccgta cacgttcgga    360
gggggggacca agctggagat cacaggtggc ggtggctcgg gcggtggtgg gtcgggtggc    420
ggcggatctg aggtgaaact gcaggagtca ggacctggcc tggtggcgcc ctcacagagc    480
ctgtccgtca catgcactgt ctcagggtc tcattacccg actatggtgt aagctggatt    540
cgccagcctc cacgaaaggg tctggagtgg ctgggagtaa tatggggtag tgaaaccaca    600
tactataatt cagctctcaa atccagactg accatcatca aggacaactc caagagccaa    660
gttttcttaa aaatgaacag tctgcaaact gatgacacag ccatttacta ctgtgccaaa    720
cattattact acggtggtag ctatgctatg gactactggg gccaaggaac ctcagtcacc    780
gtctcctcaa ccacgacgcc agcgccgcga ccaccaacac cggcgcccac catcgcgtcg    840
cagcccctgt ccctgcgccc agaggcgtgc cggccagcgg cgggggggcgc agtgcacacg    900
aggggggctgg acttcgcctg tgatatctac atctgggcgc ccttggccgg gacttgtggg    960
gtccttctcc tgtcactggt tatcacccttt tactgcaaac ggggcagaaa gaaactcctg   1020
tatatattca aacaaccatt tatgagacca gtacaaacta ctcaagagga agatggctgt   1080
agctgccgat ttccagaaga agaagaagga ggatgtgaac tgagagtgaa gttcagcagg   1140
agcgcagacg cccccgcgta caagcagggc cagaaccagc tctataacga gctcaatcta   1200
ggacgaagag aggagtacga tgttttggac aagaggcgtg gccgggaccc tgagatgggg   1260
ggaaagccga aaggaagaa ccctcaggaa ggcctgtaca tgaactgca gaaagataag   1320
atggcggagg cctacagtga gattgggatg aaaggcgagc gccggagggg caaggggcac   1380
gatggccttt accagggtct cagtacagcc accaaggaca cctacgacgc ccttcacatg   1440
caggccctgc cccctcgctc tagagccacg aacttctctc tgttaaagca agcaggagac   1500
gtggaagaaa accccggtcc tcatatgatg gccttaccag tgaccgcctt gctcctgccg   1560
ctggccttgc tgctccacgc cgccaggccg gacatcgtga tgacccagtc cccctccagc   1620
ctgacagtga cagccggcga aaggtgaca atgatctgta gtccagcca gagcctgctg   1680
aacagcggcg accagaagaa ctacctgacc tggtaccagc agaagcctgg ccagcccccc   1740
aagctgctga tcttctgggc cagcacaagg gagagcggcg tgcccgacag attcacaggc   1800
agcggcagcg gcaccgactt cacactgacc atttcctccg tgcaggccga ggacctcgcc   1860
gtgtactact gccagaacga ctactcctac cccctgacat cggcgccgg caccaaactg   1920
gagctgaagg gtggcggtgg ctcgggcggt ggtgggtcgg gtggcggcgg atctcaggtg   1980
cagctccagc agtccgatgc cgagctggtg aagcccggaa gcagcgtcaa gatcagctgt   2040
aaggcctccg gctacacctt cacagaccac gccatccact gggtgaagca gaagcccgag   2100
cagggcctgg agtggatcgg ccactttagc cccggaaaca ccgacatcaa gtacaacgac   2160
aagttcaagg gcaaggccac cctgaccgtg gacaggagca gcagcaccgc ctacatgcag   2220
ctgaacagcc tgacaagcga ggacagcgcc gtgtacttct gcaagacctc caccttcttc   2280
ttcgactact ggggccaggg aaccaccctg acagtgtcca gcaccacgac gccagcgccg   2340
cgaccaccaa caccggcgcc caccatcgcg tcgcagcccc tgtccctgcg cccagaggcg   2400
tgccggccag cggcgggggg cgcagtgcac acgagggggg ctggacttcg ctgtgatatc   2460
tacatctggg cgcccttggc cgggacttgt gggtccttc tcctgtcact ggttatcacc   2520
ctttactgca acggggcag aaagaaactc ctgtatatat tcaaacaacc atttatgaga   2580
ccagtacaaa ctactcaaga ggaagatggc tgtagctgcc gatttccaga agaagaagaa   2640
ggaggatgtg aactgagagt gaagttcagc aggagcgcag acgcccccgc gtacaagcag   2700
```

-continued

```
ggccagaacc agctctataa cgagctcaat ctaggacgaa gagaggagta cgatgttttg    2760
gacaagaggc gtggccggga ccctgagatg ggggaaagc cgagaaggaa gaaccctcag     2820
gaaggcctgt acaatgaact gcagaaagat aagatggcgg aggcctacag tgagattggg    2880
atgaaaggcg agcgccggag gggcaagggg cacgatggcc tttaccaggg tctcagtaca    2940
gccaccaagg acacctacga cgcccttcac atgcaggccc tgcccctcg ctaa           2994
```

<210> SEQ ID NO 27
<211> LENGTH: 2994
<212> TYPE: DNA
<213> ORGANISM: Artificial Sequence
<220> FEATURE:
<223> OTHER INFORMATION: Synthesized

<400> SEQUENCE: 27

```
atggccttac cagtgaccgc cttgctcctg ccgctggcct tgctgctcca cgccgccagg      60
ccggatatcc agatgaccca gagcccgagc agcctgagcg cgagcgtggg tgatcgcgtg     120
accattacct gcagggcaag tcaggacatt agtaaatatt taaattggta tcagcagaaa     180
ccgggtaaag cgccgaaact gttaatttat catacatcaa gattacactc aggcgtgccg     240
tcgcgtttta gcggctcggg ttcgggcacc gatttaccc tgaccatctc gagcttgcag      300
ccggaggact cgccaccta ctattgccaa cagggtaata cgcttccgta cacgttcggt      360
cagggcacca agtggagat caaaggtggc ggtggctcgg gcggtggtgg gtcgggtggc      420
ggcggatctg aggtgcagct ggtggagtct ggggaggct tggtacagcc tgggggtcc      480 ctgagactct cctgtgcagc ctctggagtg tccctgcctg attatggcgt gtcctgggtc      540
cgccaggctc cagggaaggg gctggagtgg gtttcagtga tctggggcag cgagacaacc      600
tactacaaca gcgccctgaa gtcccgattc accatctcca gagacaatgc caagaactca      660
ctgtatctgc aaatgaacag cctgagagcc gaggacacgg ctgtgtatta ctgtgcgaag      720
cactactact acggcggcag ctacgctatg gactactggg gccaaggaac cctggtcacc      780
gtgtcctcaa ccacgacgcc agcgccgcga ccaccaacac cggcgcccac catcgcgtcg      840
cagcccctgt ccctgcgccc agaggcgtgc cggcagcgcg gggggcgc agtgcacacg       900 agggggctgg acttcgcctg tgatatctac atctgggcgc ccttggccgg acttgtggg      960 gtccttctcc tgtcactggt tatcaccctt tactgcaaac gggggcagaa gaaactcctg     1020
tatatattca acaaccatt tatgagacca gtacaaacta ctcaagagga gatggctgt      1080 agctgccgat ttcagaaga agaagaagga ggatgtgaac tgagagtgaa gttcagcagg     1140
agcgcagacg cccccgcgta caagcagggc cagaaccagc tctataacga gctcaatcta     1200
ggacgaagag aggagtacga tgttttggac aagaggcgtg gccggaccc tgagatgggg     1260 ggaaagccga aggaagaa ccctcaggaa ggcctgtaca atgaactgca gaaagataag      1320
atggcggagg cctacagtga gattggatg aaaggcgagc gccggagggg caaggggcac     1380
gatggccttt accagggtct cagtacagcc accaaggaca cctacgacgc ccttcacatg     1440
caggccctgc ccctcgctc tagagccacg aacttctctc tgttaaagca agcaggagac     1500
gtggaagaaa accccggtcc tcatatgatg gccttaccag tgaccgcctt gctcctgccg     1560
ctggccttgc tgctccacgc cgccaggccg gacatcgtga tgacccagtc ccctccagc      1620 ctgacagtga cagccggcga aaggtgaca atgatctgta agtccagcca gagcctgctg     1680
aacagcggcg accagaagaa ctacctgacc tggtaccagc agaagcctgg ccagcccccc     1740
```

| | |
|---|---|
| aagctgctga tcttctgggc cagcacaagg gagagcggcg tgcccgacag attcacaggc | 1800 |
| agcggcagcg gcaccgactt cacactgacc atttcctccg tgcaggccga ggacctcgcc | 1860 |
| gtgtactact gccagaacga ctactcctac ccctgacat tcggcgccgg caccaaactg | 1920 |
| gagctgaagg gtggcggtgg ctcgggcggt ggtgggtcgg gtggcggcgg atctcaggtg | 1980 |
| cagctccagc agtccgatgc cgagctggtg aagcccggaa gcagcgtcaa gatcagctgt | 2040 |
| aaggcctccg gctacacctt cacagaccac gccatccact gggtgaagca gaagcccgag | 2100 |
| cagggcctgg agtggatcgg ccactttagc cccggaaaca ccgacatcaa gtacaacgac | 2160 |
| aagttcaagg gcaaggccac cctgaccgtg gacaggagca gcagcaccgc ctacatgcag | 2220 |
| ctgaacagcc tgacaagcga ggacagcgcc gtgtacttct gcaagacctc caccttcttc | 2280 |
| ttcgactact ggggccaggg aaccaccctg acagtgtcca gcaccacgac gccagcgccg | 2340 |
| cgaccaccaa caccggcgcc caccatcgcg tcgcagcccc tgtccctgcg cccagaggcg | 2400 |
| tgccggccag cggcgggggg cgcagtgcac acgagggggc tggacttcgc ctgtgatatc | 2460 |
| tacatctggg cgcccttggc cgggacttgt ggggtccttc tcctgtcact ggttatcacc | 2520 |
| ctttactgca aacggggcag aaagaaactc ctgtatatat tcaaacaacc atttatgaga | 2580 |
| ccagtacaaa ctactcaaga ggaagatggc tgtagctgcc gatttccaga agaagaagaa | 2640 |
| ggaggatgtg aactgagagt gaagttcagc aggagcgcag acgcccccgc gtacaagcag | 2700 |
| ggccagaacc agctctataa cgagctcaat ctaggacgaa gagaggagta cgatgttttg | 2760 |
| gacaagaggc gtggccggga ccctgagatg ggggggaaagc cgagaaggaa gaaccctcag | 2820 |
| gaaggcctgt acaatgaact gcagaaagat aagatggcgg aggcctacag tgagattggg | 2880 |
| atgaaaggcg agcgccggag gggcaagggg cacgatggcc tttaccaggg tctcagtaca | 2940 |
| gccaccaagg acacctacga cgcccttcac atgcaggccc tgccccctcg ctaa | 2994 |

<210> SEQ ID NO 28
<211> LENGTH: 3009
<212> TYPE: DNA
<213> ORGANISM: Artificial Sequence
<220> FEATURE:
<223> OTHER INFORMATION: Synthesized

<400> SEQUENCE: 28

| | |
|---|---|
| atggccttac cagtgaccgc cttgctcctg ccgctggcct tgctgctcca cgccgccagg | 60 |
| ccggatatcc agatgaccca gagcccaagc tccctgtccg cctctgtggg cgacagggtg | 120 |
| accatcacat gccgcgccag ccagacaatc tggtcctacc tgaactggta tcagcagaga | 180 |
| cccggcaagg cccctaatct gctgatctac gcagcatcta gcctgcagtc tggagtgccc | 240 |
| tcccggttct ctggaagagg atccggaacc gacttcaccc tgacaatctc ctctctgcag | 300 |
| gccgaggact tcgccacata ctattgccag cagagctatt ccatccctca gacctttggc | 360 |
| cagggcacaa gctggagat caagggcggc ggcggctctg gaggagggag aagcggagga | 420 |
| ggaggatccc aggtgcagct gcagcagagc ggaccaggac tggtgaagcc ctcccagacc | 480 |
| ctgtctctga catgtgccat cagcggcgat tccgtgagct ccaacagcgc cgcctggaat | 540 |
| tggatccggc agtctcccag cagaggactg gagtggctgg aaggaccta ctatcgctcc | 600 |
| aagtggtaca acgattatgc cgtgtctgtg aagagccgga tcaccatcaa ccctgacaca | 660 |
| tctaagaatc agttcagcct gcagctgaat tccgtgaccc cagaggacac agccgtgtac | 720 |
| tattgtgcaa gggaggtgac cggcgacctg gaggatgcct tgacatctg ggccagggc | 780 |
| accatggtga cagtgtctag caccacgacg ccagcgccgc gaccaccaac accggcgccc | 840 |

```
accatcgcgt cgcagcccct gtccctgcgc ccagaggcgt gccggccagc ggcgggggc      900
gcagtgcaca cgagggggct ggacttcgcc tgtgatatct acatctgggc gcccttggcc     960
gggacttgtg gggtccttct cctgtcactg gttatcaccc tttactgcaa acggggcaga   1020
aagaaactcc tgtatatatt caaacaacca tttatgagac cagtacaaac tactcaagag   1080
gaagatggct gtagctgccg atttccagaa gaagaagaag gaggatgtga actgagagtg   1140
aagttcagca ggagcgcaga cgcccccgcg tacaagcagg ccagaaccag ctctataac    1200
gagctcaatc taggacgaag agaggagtac gatgttttgg acaagaggcg tggccgggac   1260
cctgagatgg ggggaaagcc gagaaggaag aaccctcagg aaggcctgta caatgaactg   1320
cagaaagata gatggcgga ggcctacagt gagattggga tgaaaggcga gcgccggagg   1380
ggcaaggggc acgatggcct ttaccagggt ctcagtacag ccaccaagga cacctacgac   1440
gcccttcaca tgcaggccct gcccctcgc taatctagag ccacgaactt ctctctgtta   1500
aagcaagcag gagacgtgga agaaaacccc ggtcctcata tgatggcctt accagtgacc   1560
gccttgctcc tgccgctggc cttgctgctc cacgccgcca ggccggacat cgtgatgacc   1620
cagtcccct ccagcctgac agtgacagcc ggcgagaagg tgacaatgat ctgtaagtcc    1680
agccagagcc tgctgaacag cggcgaccag aagaactacc tgacctggta ccagcagaag   1740
cctggccagc cccccaagct gctgatcttc tgggccagca agggagag cggcgtgccc     1800
gacagattca caggcagcgg cagcggcacc gacttcacac tgaccatttc ctccgtgcag   1860
gccgaggacc tcgccgtgta ctactgccag aacgactact cctacccct gacattcggc   1920
gccggcacca aactggagct gaagggtggc ggtggctcgg gcggtggtgg gtcgggtggc   1980
ggcggatctc aggtgcagct ccagcagtcc gatgccgagc tggtgaagcc cggaagcagc   2040
gtcaagatca gctgtaaggc ctccggctac accttcacag accacgccat ccactgggtg   2100
aagcagaagc ccgagcaggg cctggagtgg atcggccact ttagccccgg aaacaccgac   2160
atcaagtaca cgacaagtt caagggcaag gccaccctga ccgtggacag gagcagcagc   2220
accgcctaca tgcagctgaa cagcctgaca agcgaggaca cgccgtgta cttctgcaag   2280
acctccacct tcttcttcga ctactgggc cagggaacca ccctgacagt gtccagcacc   2340
acgacgccag cgccgcgacc accaacaccg gcgcccacca tcgcgtcgca gccctgtcc    2400
ctgcgcccaa ggcgtgccg gccagcgcg gggggcgcag tgcacacgag ggggctggac    2460
ttcgcctgtg atatctacat ctgggcgccc ttggccggga cttgtggggt ccttctcctg   2520
tcactggtta tcacccttta ctgcaaacgg ggcagaaaga aactcctgta tatattcaaa   2580
caaccattta tgagaccagt acaaactact caagaggaag atggctgtag ctgccgattt   2640
ccagaagaag aagaaggagg atgtgaactg agagtgaagt tcagcaggag cgcagacgcc   2700
cccgcgtaca gcagggcca gaaccagctc tataacgagc tcaatctagg acgaagagag   2760
gagtacgatg ttttggacaa gaggcgtggc cgggacctg agatgggggg aaagccgaga   2820
aggaagaacc ctcaggaagg cctgtacaat gaactgcaga agataagat ggcggaggcc   2880
tacagtgaga ttgggatgaa aggcgagcgc cggaggggca aggggcacga tggcctttac   2940
cagggtctca gtacagccac caaggacacc tacgacgccc ttcacatgca ggccctgccc   3000
cctcgctaa                                                          3009
```

<210> SEQ ID NO 29
<211> LENGTH: 2982
<212> TYPE: DNA

<213> ORGANISM: Artificial Sequence
<220> FEATURE:
<223> OTHER INFORMATION: Synthesized

<400> SEQUENCE: 29

```
atggccttac cagtgaccgc cttgctcctg ccgctggcct tgctgctcca cgccgccagg      60
ccggacatcc agctcaccca gtccccgagc tcgctgtccg cctccgtggg agatcgggtc     120
accatcacgt gccgcgccag ccagtcgatt tcctcctacc tgaactggta ccaacagaag     180
cccggaaaag ccccgaagct tctcatctac gccgcctcga gcctgcagtc aggagtgccc     240
tcacggttct ccggctccgg ttccggtact gatttcaccc tgaccatttc tccctgcaa     300
ccggaggact cgctactta ctactgccag cagtcgtact ccaccccta cactttcgga     360
caaggcacca aggtcgaaat caaggtggc ggtggctcgg cggtggtgg gtcgggtggc     420
ggcggatctg aagtgcaatt ggtggaatca ggggaggac ttgtgcagcc tggaggatcg     480
ctgagactgt catgtgccgt gtccggcttt gccctgtcca accacgggat gtcctgggtc     540
cgccgcgcgc ctggaaaggg cctcgaatgg gtgtcgggta ttgtgtacag cggtagcacc     600
tactatgccg catccgtgaa ggggagattc accatcagcc gggacaactc caggaacact     660
ctgtacctcc aaatgaattc gctgaggcca gaggacactg ccatctacta ctgctccgcg     720
catggcggag agtccgacgt ctggggacag ggaccaccg tgaccgtgtc tagcaccacg     780
acgccagcgc cgcgaccacc aacaccggcg cccaccatcg cgtcgcagcc cctgtccctg     840
cgcccagagg cgtgccggcc agcggcgggg ggcgcagtgc acacgagggg gctggacttc     900
gcctgtgata tctacatctg gcgcccttg ccgggactt gtggggtcct tctcctgtca     960
ctggttatca ccctttactg caaacggggc agaaagaaac tcctgtatat attcaaacaa    1020
ccatttatga gaccagtaca aactactcaa gaggaagatg gctgtagctg ccgatttcca    1080
gaagaagaag aaggaggatg tgaactgaga gtgaagttca gcaggagcgc agacgccccc    1140
gcgtacaagc agggccagaa ccagctctat aacgagctca atctaggacg aagagaggag    1200
tacgatgttt tggacaagag gcgtggccgg gaccctgaga tggggggaaa gccgagaagg    1260
aagaaccctc aggaaggcct gtacaatgaa ctgcagaaag ataagatggc ggaggcctac    1320
agtgagattg ggatgaaagg cgagcgccgg aggggcaagg ggcacgatgg cctttaccag    1380
ggtctcagta cagccaccaa ggacacctac gacgcccttc acatgcaggc cctgccccct    1440
cgctaatcta gagccacgaa cttctctctg ttaaagcaag caggagacgt ggaagaaaac    1500
cccggtcctc atatgatggc cttaccagtg accgccttgc tcctgccgct ggccttgctg    1560
ctccacgccg ccaggccgga catcgtgatg acccagtccc cctccagcct gacagtgaca    1620
gccggcgaga aggtgacaat gatctgtaag tccagccaga gcctgctgaa cagcggcgac    1680
cagaagaact acctgacctg gtaccagcag aagcctggcc agccccccaa gctgctgatc    1740
ttctgggcca gcacaaggga gagcggcgtg cccgacagat tcacaggcag cggcagcggc    1800
accgacttca cactgaccat ttcctccgtg caggccgagg acctcgccgt gtactactgc    1860
cagaacgact actcctaccc cctgacattc ggcgccggca ccaaactgga gctgaagggt    1920
ggcggtggct cggcggtgg tgggtcgggt ggcggcggat ctcaggtgca gctccagcag    1980
tccgatgccg agctggtgaa gcccggaagc agcgtcaaga tcagctgtaa ggcctccggc    2040
tacaccttca cagaccacgc catccactgg gtgaagcaga gcccgagca gggcctggag    2100
tggatcggcc actttagccc cggaaacacc gacatcaagt acaacgacaa gttcaagggc    2160
aaggccaccc tgaccgtgga caggagcagc agcaccgcct acatgcagct gaacagcctg    2220
```

-continued

```
acaagcgagg acagcgccgt gtacttctgc aagacctcca ccttcttctt cgactactgg    2280
ggccagggaa ccaccctgac agtgtccagc accacgacgc cagcgccgcg accaccaaca    2340
ccggcgccca ccatcgcgtc gcagcccctg tccctgcgcc agaggcgtg ccggccagcg     2400 gcggggggcg cagtgcacac gagggggctg gacttcgcct gtgatatcta catctgggcg    2460
cccttggccg ggacttgtgg ggtccttctc ctgtcactgg ttatcaccct ttactgcaaa    2520
cggggcagaa agaaactcct gtatatattc aaacaaccat ttatgagacc agtacaaact    2580
actcaagagg aagatggctg tagctgccga tttccagaag aagaagaagg aggatgtgaa    2640
ctgagagtga agttcagcag gagcgcagac gccccgcgt acaagcaggg ccagaaccag      2700
ctctataacg agctcaatct aggacgaaga gaggagtacg atgttttgga caagaggcgt    2760
ggccgggacc ctgagatggg gggaaagccg agaaggaaga accctcagga aggcctgtac    2820
aatgaactgc agaaagataa gatggcggag gcctacagtg agattgggat gaaaggcgag    2880
cgccggaggg gcaaggggca cgatggcctt taccagggtc tcagtacagc caccaaggac    2940
acctacgacg cccttcacat gcaggccctg cccctcgct aa                        2982
```

<210> SEQ ID NO 30
<211> LENGTH: 244
<212> TYPE: PRT
<213> ORGANISM: Artificial Sequence
<220> FEATURE:
<223> OTHER INFORMATION: Synthesized

<400> SEQUENCE: 30

```
Asp Ile Val Met Thr Gln Ser Pro Ser Ser Leu Thr Val Thr Ala Gly
1               5                   10                  15

Glu Lys Val Thr Met Ile Cys Lys Ser Ser Gln Ser Leu Leu Asn Ser
            20                  25                  30

Gly Asp Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Gly Gly Gly Gly Ser Gly Gly Gly Gly Ser Gly Gly Gly Gly Ser
        115                 120                 125

Gln Val Gln Leu Gln Gln Ser Asp Ala Glu Leu Val Lys Pro Gly Ser
    130                 135                 140

Ser Val Lys Ile Ser Cys Lys Ala Ser Gly Tyr Thr Phe Thr Asp His
145                 150                 155                 160

Ala Ile His Trp Val Lys Gln Lys Pro Glu Gln Gly Leu Glu Trp Ile
                165                 170                 175

Gly His Phe Ser Pro Gly Asn Thr Asp Ile Lys Tyr Asn Asp Lys Phe
            180                 185                 190

Lys Gly Lys Ala Thr Leu Thr Val Asp Arg Ser Ser Ser Thr Ala Tyr
        195                 200                 205

Met Gln Leu Asn Ser Leu Thr Ser Glu Asp Ser Ala Val Tyr Phe Cys
    210                 215                 220
```

```
Lys Thr Ser Thr Phe Phe Asp Tyr Trp Gly Gln Gly Thr Thr Leu
225                 230                 235                 240

Thr Val Ser Ser
```

<210> SEQ ID NO 31
<211> LENGTH: 116
<212> TYPE: PRT
<213> ORGANISM: Artificial Sequence
<220> FEATURE:
<223> OTHER INFORMATION: Synthesized

<400> SEQUENCE: 31

```
Gln Val Gln Leu Gln Gln Ser Asp Ala Glu Leu Val Lys Pro Gly Ser
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly His Phe Ser Pro Gly Asn Thr Asp Ile Lys Tyr Asn Asp Lys Phe
    50                  55                  60

Lys Gly Lys Ala Thr Leu Thr Val Asp Arg Ser Ser Ser Thr Ala Tyr
65                  70                  75                  80

Met Gln Leu Asn Ser Leu Thr Ser Glu Asp Ser Ala Val Tyr Phe Cys
                85                  90                  95

Lys Thr Ser Thr Phe Phe Asp Tyr Trp Gly Gln Gly Thr Thr Leu
            100                 105                 110

Thr Val Ser Ser
        115
```

<210> SEQ ID NO 32
<211> LENGTH: 113
<212> TYPE: PRT
<213> ORGANISM: Artificial Sequence
<220> FEATURE:
<223> OTHER INFORMATION: Synthesized

<400> SEQUENCE: 32

```
Asp Ile Val Met Thr Gln Ser Pro Ser Ser Leu Thr Val Thr Ala Gly
1               5                   10                  15

Glu Lys Val Thr Met Ile Cys Lys Ser Ser Gln Ser Leu Leu Asn Ser
            20                  25                  30

Gly Asp Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys
```

<210> SEQ ID NO 33
<211> LENGTH: 246
<212> TYPE: PRT
<213> ORGANISM: Artificial Sequence
<220> FEATURE:
<223> OTHER INFORMATION: Synthesized

<400> SEQUENCE: 33

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Leu Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Leu Glu Ile Lys
            100                 105                 110

Arg Ala Gly Gly Gly Ser Gly Gly Gly Ser Gly Gly Gly
            115                 120                 125

Ser Glu Val Lys Leu Val Glu Ser Gly Gly Leu Val Gln Pro Gly
130                 135                 140

Gly Ser Met Lys Leu Ser Cys Val Ala Ser Gly Phe Thr Phe Ser Asn
145                 150                 155                 160

Tyr Trp Met Asn Trp Val Arg Gln Ser Pro Glu Lys Gly Leu Glu Trp
                165                 170                 175

Val Ala Glu Ile Arg Leu Lys Ser Asn Asn Tyr Thr Thr His Tyr Ala
                180                 185                 190

Glu Ser Val Lys Gly Arg Phe Thr Ile Ser Arg Asp Asp Ser Lys Ser
            195                 200                 205

Ser Val Ser Leu Gln Met Asn Asn Leu Arg Val Glu Asp Thr Gly Ile
    210                 215                 220

Tyr Tyr Cys Thr Arg His Tyr Tyr Phe Asp Tyr Trp Gly Gln Gly Thr
225                 230                 235                 240

Thr Leu Thr Val Ser Ser
                245

<210> SEQ ID NO 34
<211> LENGTH: 117
<212> TYPE: PRT
<213> ORGANISM: Artificial Sequence
<220> FEATURE:
<223> OTHER INFORMATION: Synthesized

<400> SEQUENCE: 34

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Ser Ser
65                  70                  75                  80

Val Ser Leu Gln Met Asn Asn Leu Arg Val Glu Asp Thr Gly Ile Tyr
                85                  90                  95

Tyr Cys Thr Arg His Tyr Tyr Phe Asp Tyr Trp Gly Gln Gly Thr Thr
                100                 105                 110

Leu Thr Val Ser Ser
        115

<210> SEQ ID NO 35
<211> LENGTH: 114
<212> TYPE: PRT
<213> ORGANISM: Artificial Sequence
<220> FEATURE:
<223> OTHER INFORMATION: Synthesized

<400> SEQUENCE: 35

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Leu Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Leu Glu Ile Lys
            100                 105                 110

Arg Ala

<210> SEQ ID NO 36
<211> LENGTH: 219
<212> TYPE: PRT
<213> ORGANISM: Homo sapiens

<400> SEQUENCE: 36

Glu Leu Cys Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

```
Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
            195                 200                 205

Met Glu Thr Ser Ile Phe Thr Thr Glu Tyr Gln
            210                 215

<210> SEQ ID NO 37
<211> LENGTH: 346
<212> TYPE: PRT
<213> ORGANISM: Homo sapiens

<400> SEQUENCE: 37

Leu Ala Pro Arg Arg Cys Pro Ala Gln Glu Val Ala Arg Gly Val Leu
1               5                   10                  15

Thr Ser Leu Pro Gly Asp Ser Val Thr Leu Thr Cys Pro Gly Val Glu
            20                  25                  30

Pro Glu Asp Asn Ala Thr Val His Trp Val Leu Arg Lys Pro Ala Ala
            35                  40                  45

Gly Ser His Pro Ser Arg Trp Ala Gly Met Gly Arg Arg Leu Leu Leu
50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
            85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
            115                 120                 125

Leu Leu Val Arg Lys Phe Gln Asn Ser Pro Ala Glu Asp Phe Gln Glu
130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
            165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
            195                 200                 205

Ala Arg Asn Pro Arg Trp Leu Ser Val Thr Trp Gln Asp Pro His Ser
210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
            245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
            275                 280                 285

Pro Glu Ala Met Gly Thr Pro Trp Thr Glu Ser Arg Ser Pro Pro Ala
            290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
```

```
                    325                 330                 335
Val Gln Asp Ser Ser Val Pro Leu Pro
            340                 345

<210> SEQ ID NO 38
<211> LENGTH: 219
<212> TYPE: PRT
<213> ORGANISM: Homo sapiens

<400> SEQUENCE: 38

Glu Ser Gly Tyr Ala Gln Asn Gly Asp Leu Glu Asp Ala Glu Leu Asp
1               5                   10                  15

Asp Tyr Ser Phe Ser Cys Tyr Ser Gln Leu Glu Val Asn Gly Ser Gln
            20                  25                  30

His Ser Leu Thr Cys Ala Phe Glu Asp Pro Asp Val Asn Ile Thr Asn
        35                  40                  45

Leu Glu Phe Glu Ile Cys Gly Ala Leu Val Glu Val Lys Cys Leu Asn
    50                  55                  60

Phe Arg Lys Leu Gln Glu Ile Tyr Phe Ile Glu Thr Lys Lys Phe Leu
65                  70                  75                  80

Leu Ile Gly Lys Ser Asn Ile Cys Val Lys Val Gly Glu Lys Ser Leu
                85                  90                  95

Thr Cys Lys Lys Ile Asp Leu Thr Thr Ile Val Lys Pro Glu Ala Pro
            100                 105                 110

Phe Asp Leu Ser Val Val Tyr Arg Glu Gly Ala Asn Asp Phe Val Val
        115                 120                 125

Thr Phe Asn Thr Ser His Leu Gln Lys Lys Tyr Val Lys Val Leu Met
    130                 135                 140

His Asp Val Ala Tyr Arg Gln Glu Lys Asp Glu Asn Lys Trp Thr His
145                 150                 155                 160

Val Asn Leu Ser Ser Thr Lys Leu Thr Leu Leu Gln Arg Lys Leu Gln
                165                 170                 175

Pro Ala Ala Met Tyr Glu Ile Lys Val Arg Ser Ile Pro Asp His Tyr
            180                 185                 190

Phe Lys Gly Phe Trp Ser Glu Trp Ser Pro Ser Tyr Tyr Phe Arg Thr
        195                 200                 205

Pro Glu Ile Asn Asn Ser Gly Glu Met Asp
    210                 215

<210> SEQ ID NO 39
<211> LENGTH: 522
<212> TYPE: PRT
<213> ORGANISM: Homo sapiens

<400> SEQUENCE: 39

Cys Arg Thr Ser Glu Cys Cys Phe Gln Asp Pro Pro Tyr Pro Asp Ala
1               5                   10                  15

Asp Ser Gly Ser Ala Ser Gly Pro Arg Asp Leu Arg Cys Tyr Arg Ile
            20                  25                  30

Ser Ser Asp Arg Tyr Glu Cys Ser Trp Gln Tyr Glu Gly Pro Thr Ala
        35                  40                  45

Gly Val Ser His Phe Leu Arg Cys Cys Leu Ser Ser Gly Arg Cys Cys
    50                  55                  60

Tyr Phe Ala Ala Gly Ser Ala Thr Arg Leu Gln Phe Ser Asp Gln Ala
65                  70                  75                  80

Gly Val Ser Val Leu Tyr Thr Val Thr Leu Trp Val Glu Ser Trp Ala
```

```
                   85                  90                  95
Arg Asn Gln Thr Glu Lys Ser Pro Glu Val Thr Leu Gln Leu Tyr Asn
                100                 105                 110

Ser Val Lys Tyr Glu Pro Pro Leu Gly Asp Ile Lys Val Ser Lys Leu
                115                 120                 125

Ala Gly Gln Leu Arg Met Glu Trp Glu Thr Pro Asp Asn Gln Val Gly
                130                 135                 140

Ala Glu Val Gln Phe Arg His Arg Thr Pro Ser Ser Pro Trp Lys Leu
145                 150                 155                 160

Gly Asp Cys Gly Pro Gln Asp Asp Thr Glu Ser Cys Leu Cys Pro
                165                 170                 175

Leu Glu Met Asn Val Ala Gln Glu Phe Gln Leu Arg Arg Gln Leu
                180                 185                 190

Gly Ser Gln Gly Ser Ser Trp Ser Lys Trp Ser Pro Val Cys Val
                195                 200                 205

Pro Pro Glu Asn Pro Pro Gln Pro Gln Val Arg Phe Ser Val Glu Gln
                210                 215                 220

Leu Gly Gln Asp Gly Arg Arg Leu Thr Leu Lys Glu Gln Pro Thr
225                 230                 235                 240

Gln Leu Glu Leu Pro Glu Gly Cys Gln Gly Leu Ala Pro Gly Thr Glu
                245                 250                 255

Val Thr Tyr Arg Leu Gln Leu His Met Leu Ser Cys Pro Cys Lys Ala
                260                 265                 270

Lys Ala Thr Arg Thr Leu His Leu Gly Lys Met Pro Tyr Leu Ser Gly
                275                 280                 285

Ala Ala Tyr Asn Val Ala Val Ile Ser Ser Asn Gln Phe Gly Pro Gly
                290                 295                 300

Leu Asn Gln Thr Trp His Ile Pro Ala Asp Thr His Thr Glu Pro Val
305                 310                 315                 320

Ala Leu Asn Ile Ser Val Gly Thr Asn Gly Thr Thr Met Tyr Trp Pro
                325                 330                 335

Ala Arg Ala Gln Ser Met Thr Tyr Cys Ile Glu Trp Gln Pro Val Gly
                340                 345                 350

Gln Asp Gly Gly Leu Ala Thr Cys Ser Leu Thr Ala Pro Gln Asp Pro
                355                 360                 365

Asp Pro Ala Gly Met Ala Thr Tyr Ser Trp Ser Arg Glu Ser Gly Ala
                370                 375                 380

Met Gly Gln Glu Lys Cys Tyr Tyr Ile Thr Ile Phe Ala Ser Ala His
385                 390                 395                 400

Pro Glu Lys Leu Thr Leu Trp Ser Thr Val Leu Ser Thr Tyr His Phe
                405                 410                 415

Gly Gly Asn Ala Ser Ala Ala Gly Thr Pro His His Val Ser Val Lys
                420                 425                 430

Asn His Ser Leu Asp Ser Val Ser Val Asp Trp Ala Pro Ser Leu Leu
                435                 440                 445

Ser Thr Cys Pro Gly Val Leu Lys Glu Tyr Val Val Arg Cys Arg Asp
                450                 455                 460

Glu Asp Ser Lys Gln Val Ser Glu His Pro Val Gln Pro Thr Glu Thr
465                 470                 475                 480

Gln Val Thr Leu Ser Gly Leu Arg Ala Gly Val Ala Tyr Thr Val Gln
                485                 490                 495

Val Arg Ala Asp Thr Ala Trp Leu Arg Gly Val Trp Ser Gln Pro Gln
                500                 505                 510
```

```
Arg Phe Ser Ile Glu Val Gln Val Ser Asp
        515                 520
```

<210> SEQ ID NO 40
<211> LENGTH: 175
<212> TYPE: PRT
<213> ORGANISM: Homo sapiens

<400> SEQUENCE: 40

```
Ile Thr Cys Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Ser Pro Ser Ser Asn Asn Thr Ala Ala Thr
            100                 105                 110

Thr Ala Ala Ile Val Pro Gly Ser Gln Leu Met Pro Ser Lys Ser Pro
        115                 120                 125

Ser Thr Gly Thr Thr Glu Ile Ser Ser His Glu Ser Ser His Gly Thr
    130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr
                165                 170                 175
```

<210> SEQ ID NO 41
<211> LENGTH: 213
<212> TYPE: PRT
<213> ORGANISM: Homo sapiens

<400> SEQUENCE: 41

```
Cys Pro Asp Leu Val Cys Tyr Thr Asp Tyr Leu Gln Thr Val Ile Cys
1               5                   10                  15

Ile Leu Glu Met Trp Asn Leu His Pro Ser Thr Leu Thr Leu Thr Trp
            20                  25                  30

Gln Asp Gln Tyr Glu Glu Leu Lys Asp Glu Ala Thr Ser Cys Ser Leu
        35                  40                  45

His Arg Ser Ala His Asn Ala Thr His Ala Thr Tyr Thr Cys His Met
    50                  55                  60

Asp Val Phe His Phe Met Ala Asp Asp Ile Phe Ser Val Asn Ile Thr
65                  70                  75                  80

Asp Gln Ser Gly Asn Tyr Ser Gln Glu Cys Gly Ser Phe Leu Leu Ala
                85                  90                  95

Glu Ser Ile Lys Pro Ala Pro Pro Phe Asn Val Thr Val Thr Phe Ser
            100                 105                 110

Gly Gln Tyr Asn Ile Ser Trp Arg Ser Asp Tyr Glu Asp Pro Ala Phe
        115                 120                 125

Tyr Met Leu Lys Gly Lys Leu Gln Tyr Glu Leu Gln Tyr Arg Asn Arg
    130                 135                 140
```

```
Gly Asp Pro Trp Ala Val Ser Pro Arg Arg Lys Leu Ile Ser Val Asp
145                 150                 155                 160

Ser Arg Ser Val Ser Leu Leu Pro Leu Glu Phe Arg Lys Asp Ser Ser
                165                 170                 175

Tyr Glu Leu Gln Val Arg Ala Gly Pro Met Pro Gly Ser Ser Tyr Gln
            180                 185                 190

Gly Thr Trp Ser Glu Trp Ser Asp Pro Val Ile Phe Gln Thr Gln Ser
        195                 200                 205

Glu Glu Leu Lys Glu
        210

<210> SEQ ID NO 42
<211> LENGTH: 332
<212> TYPE: PRT
<213> ORGANISM: Homo sapiens

<400> SEQUENCE: 42

Gly Ile Thr Asn Ile Asn Cys Ser Gly His Ile Trp Val Glu Pro Ala
1               5                   10                  15

Thr Ile Phe Lys Met Gly Met Asn Ile Ser Ile Tyr Cys Gln Ala Ala
            20                  25                  30

Ile Lys Asn Cys Gln Pro Arg Lys Leu His Phe Tyr Lys Asn Gly Ile
        35                  40                  45

Lys Glu Arg Phe Gln Ile Thr Arg Ile Asn Lys Thr Thr Ala Arg Leu
    50                  55                  60

Trp Tyr Lys Asn Phe Leu Glu Pro His Ala Ser Met Tyr Cys Thr Ala
65                  70                  75                  80

Glu Cys Pro Lys His Phe Gln Glu Thr Leu Ile Cys Gly Lys Asp Ile
                85                  90                  95

Ser Ser Gly Tyr Pro Pro Asp Ile Pro Asp Glu Val Thr Cys Val Ile
            100                 105                 110

Tyr Glu Tyr Ser Gly Asn Met Thr Cys Thr Trp Asn Ala Gly Lys Leu
        115                 120                 125

Thr Tyr Ile Asp Thr Lys Tyr Val Val His Val Lys Ser Leu Glu Thr
    130                 135                 140

Glu Glu Glu Gln Gln Tyr Leu Thr Ser Ser Tyr Ile Asn Ile Ser Thr
145                 150                 155                 160

Asp Ser Leu Gln Gly Gly Lys Lys Tyr Leu Val Trp Val Gln Ala Ala
                165                 170                 175

Asn Ala Leu Gly Met Glu Glu Ser Lys Gln Leu Gln Ile His Leu Asp
            180                 185                 190

Asp Ile Val Ile Pro Ser Ala Ala Val Ile Ser Arg Ala Glu Thr Ile
        195                 200                 205

Asn Ala Thr Val Pro Lys Thr Ile Ile Tyr Trp Asp Ser Gln Thr Thr
    210                 215                 220

Ile Glu Lys Val Ser Cys Glu Met Arg Tyr Lys Ala Thr Thr Asn Gln
225                 230                 235                 240

Thr Trp Asn Val Lys Glu Phe Asp Thr Asn Phe Thr Tyr Val Gln Gln
                245                 250                 255

Ser Glu Phe Tyr Leu Glu Pro Asn Ile Lys Tyr Val Phe Gln Val Arg
            260                 265                 270

Cys Gln Glu Thr Gly Lys Arg Tyr Trp Gln Pro Trp Ser Ser Leu Phe
        275                 280                 285

Phe His Lys Thr Pro Glu Thr Val Pro Gln Val Thr Ser Lys Ala Phe
```

```
                    290                 295                 300
Gln His Asp Thr Trp Asn Ser Gly Leu Thr Val Ala Ser Ile Ser Thr
305                 310                 315                 320

Gly His Leu Thr Ser Asp Asn Arg Gly Asp Ile Gly
                325                 330
```

<210> SEQ ID NO 43
<211> LENGTH: 19
<212> TYPE: PRT
<213> ORGANISM: Homo sapiens

<400> SEQUENCE: 43

```
Val Ala Val Ala Gly Cys Val Phe Leu Leu Ile Ser Val Leu Leu Leu
1               5                   10                  15

Ser Gly Leu
```

<210> SEQ ID NO 44
<211> LENGTH: 21
<212> TYPE: PRT
<213> ORGANISM: Homo sapiens

<400> SEQUENCE: 44

```
Thr Phe Leu Val Ala Gly Gly Ser Leu Ala Phe Gly Thr Leu Leu Cys
1               5                   10                  15

Ile Ala Ile Val Leu
                20
```

<210> SEQ ID NO 45
<211> LENGTH: 25
<212> TYPE: PRT
<213> ORGANISM: Homo sapiens

<400> SEQUENCE: 45

```
Pro Ile Leu Leu Thr Ile Ser Ile Leu Ser Phe Phe Ser Val Ala Leu
1               5                   10                  15

Leu Val Ile Leu Ala Cys Val Leu Trp
                20                  25
```

<210> SEQ ID NO 46
<211> LENGTH: 25
<212> TYPE: PRT
<213> ORGANISM: Homo sapiens

<400> SEQUENCE: 46

```
Trp Leu Ile Phe Phe Ala Ser Leu Gly Ser Phe Leu Ser Ile Leu Leu
1               5                   10                  15

Val Gly Val Leu Gly Tyr Leu Gly Leu
                20                  25
```

<210> SEQ ID NO 47
<211> LENGTH: 23
<212> TYPE: PRT
<213> ORGANISM: Homo sapiens

<400> SEQUENCE: 47

```
Val Ala Ile Ser Thr Ser Thr Val Leu Leu Cys Gly Leu Ser Ala Val
1               5                   10                  15

Ser Leu Leu Ala Cys Tyr Leu
                20
```

<210> SEQ ID NO 48

```
<211> LENGTH: 21
<212> TYPE: PRT
<213> ORGANISM: Homo sapiens

<400> SEQUENCE: 48

Gly Trp Asn Pro His Leu Leu Leu Leu Leu Leu Val Ile Val Phe
1               5                   10                  15

Ile Pro Ala Phe Trp
            20

<210> SEQ ID NO 49
<211> LENGTH: 21
<212> TYPE: PRT
<213> ORGANISM: Homo sapiens

<400> SEQUENCE: 49

Leu Leu Leu Gly Met Ile Val Phe Ala Val Met Leu Ser Ile Leu Ser
1               5                   10                  15

Leu Ile Gly Ile Phe
            20

<210> SEQ ID NO 50
<211> LENGTH: 13
<212> TYPE: PRT
<213> ORGANISM: Homo sapiens

<400> SEQUENCE: 50

Thr Trp Gln Arg Arg Gln Arg Lys Ser Arg Arg Thr Ile
1               5                   10

<210> SEQ ID NO 51
<211> LENGTH: 82
<212> TYPE: PRT
<213> ORGANISM: Homo sapiens

<400> SEQUENCE: 51

Arg Phe Lys Lys Thr Trp Lys Leu Arg Ala Leu Lys Glu Gly Lys Thr
1               5                   10                  15

Ser Met His Pro Pro Tyr Ser Leu Gly Gln Leu Val Pro Glu Arg Pro
            20                  25                  30

Arg Pro Thr Pro Val Leu Val Pro Leu Ile Ser Pro Pro Val Ser Pro
        35                  40                  45

Ser Ser Leu Gly Ser Asp Asn Thr Ser Ser His Asn Arg Pro Asp Ala
    50                  55                  60

Arg Asp Pro Arg Ser Pro Tyr Asp Ile Ser Asn Thr Asp Tyr Phe Phe
65                  70                  75                  80

Pro Arg

<210> SEQ ID NO 52
<211> LENGTH: 195
<212> TYPE: PRT
<213> ORGANISM: Homo sapiens

<400> SEQUENCE: 52

Lys Lys Arg Ile Lys Pro Ile Val Trp Pro Ser Leu Pro Asp His Lys
1               5                   10                  15

Lys Thr Leu Glu His Leu Cys Lys Lys Pro Arg Lys Asn Leu Asn Val
            20                  25                  30

Ser Phe Asn Pro Glu Ser Phe Leu Asp Cys Gln Ile His Arg Val Asp
        35                  40                  45
```

```
Asp Ile Gln Ala Arg Asp Glu Val Glu Gly Phe Leu Gln Asp Thr Phe
        50                  55                  60

Pro Gln Gln Leu Glu Glu Ser Glu Lys Gln Arg Leu Gly Gly Asp Val
65                  70                  75                  80

Gln Ser Pro Asn Cys Pro Ser Glu Asp Val Val Ile Thr Pro Glu Ser
                85                  90                  95

Phe Gly Arg Asp Ser Ser Leu Thr Cys Leu Ala Gly Asn Val Ser Ala
            100                 105                 110

Cys Asp Ala Pro Ile Leu Ser Ser Arg Ser Leu Asp Cys Arg Glu
            115                 120                 125

Ser Gly Lys Asn Gly Pro His Val Tyr Gln Asp Leu Leu Ser Leu
        130                 135                 140

Gly Thr Thr Asn Ser Thr Leu Pro Pro Phe Ser Leu Gln Ser Gly
145                 150                 155                 160

Ile Leu Thr Leu Asn Pro Val Ala Gln Gly Gln Pro Ile Leu Thr Ser
                165                 170                 175

Leu Gly Ser Asn Gln Glu Glu Ala Tyr Val Thr Met Ser Ser Phe Tyr
            180                 185                 190

Gln Asn Gln
        195

<210> SEQ ID NO 53
<211> LENGTH: 92
<212> TYPE: PRT
<213> ORGANISM: Homo sapiens

<400> SEQUENCE: 53

Asn Arg Ala Ala Arg His Leu Cys Pro Pro Leu Pro Thr Pro Cys Ala
1               5                   10                  15

Ser Ser Ala Ile Glu Phe Pro Gly Gly Lys Thr Trp Gln Trp Ile
            20                  25                  30

Asn Pro Val Asp Phe Gln Glu Glu Ala Ser Leu Gln Glu Ala Leu Val
                35                  40                  45

Val Glu Met Ser Trp Asp Lys Gly Glu Arg Thr Glu Pro Leu Glu Lys
        50                  55                  60

Thr Glu Leu Pro Glu Gly Ala Pro Glu Leu Ala Leu Asp Thr Glu Leu
65                  70                  75                  80

Ser Leu Glu Asp Gly Asp Arg Cys Lys Ala Lys Met
            85                  90

<210> SEQ ID NO 54
<211> LENGTH: 39
<212> TYPE: PRT
<213> ORGANISM: Homo sapiens

<400> SEQUENCE: 54

Lys Ser Arg Gln Thr Pro Pro Leu Ala Ser Val Glu Met Glu Ala Met
1               5                   10                  15

Glu Ala Leu Pro Val Thr Trp Gly Thr Ser Ser Arg Asp Glu Asp Leu
            20                  25                  30

Glu Asn Cys Ser His His Leu
        35

<210> SEQ ID NO 55
<211> LENGTH: 285
<212> TYPE: PRT
<213> ORGANISM: Homo sapiens
```

<400> SEQUENCE: 55

Ser Leu Lys Thr His Pro Leu Trp Arg Leu Trp Lys Lys Ile Trp Ala
1               5                   10                  15

Val Pro Ser Pro Glu Arg Phe Phe Met Pro Leu Tyr Lys Gly Cys Ser
            20                  25                  30

Gly Asp Phe Lys Lys Trp Val Gly Ala Pro Phe Thr Gly Ser Ser Leu
        35                  40                  45

Glu Leu Gly Pro Trp Ser Pro Glu Val Pro Ser Thr Leu Glu Val Tyr
    50                  55                  60

Ser Cys His Pro Pro Arg Ser Pro Ala Lys Arg Leu Gln Leu Thr Glu
65                  70                  75                  80

Leu Gln Glu Pro Ala Glu Leu Val Glu Ser Asp Gly Val Pro Lys Pro
                85                  90                  95

Ser Phe Trp Pro Thr Ala Gln Asn Ser Gly Ser Ala Tyr Ser Glu
            100                 105                 110

Glu Arg Asp Arg Pro Tyr Gly Leu Val Ser Ile Asp Thr Val Thr Val
            115                 120                 125

Leu Asp Ala Glu Gly Pro Cys Thr Trp Pro Cys Ser Cys Glu Asp Asp
130                 135                 140

Gly Tyr Pro Ala Leu Asp Leu Asp Ala Gly Leu Glu Pro Ser Pro Gly
145                 150                 155                 160

Leu Glu Asp Pro Leu Leu Asp Ala Gly Thr Thr Val Leu Ser Cys Gly
                165                 170                 175

Cys Val Ser Ala Gly Ser Pro Gly Leu Gly Pro Leu Gly Ser Leu
            180                 185                 190

Leu Asp Arg Leu Lys Pro Pro Leu Ala Asp Gly Glu Asp Trp Ala Gly
    195                 200                 205

Gly Leu Pro Trp Gly Gly Arg Ser Pro Gly Gly Val Ser Glu Ser Glu
    210                 215                 220

Ala Gly Ser Pro Leu Ala Gly Leu Asp Met Asp Thr Phe Asp Ser Gly
225                 230                 235                 240

Phe Val Gly Ser Asp Cys Ser Ser Pro Val Glu Cys Asp Phe Thr Ser
                245                 250                 255

Pro Gly Asp Glu Gly Pro Pro Arg Ser Tyr Leu Arg Gln Trp Val Val
            260                 265                 270

Ile Pro Pro Pro Leu Ser Ser Pro Gly Pro Gln Ala Ser
            275                 280                 285

<210> SEQ ID NO 56
<211> LENGTH: 253
<212> TYPE: PRT
<213> ORGANISM: Homo sapiens

<400> SEQUENCE: 56

Asn Arg Ser Phe Arg Thr Gly Ile Lys Arg Arg Ile Leu Leu Leu Ile
1               5                   10                  15

Pro Lys Trp Leu Tyr Glu Asp Ile Pro Asn Met Lys Asn Ser Asn Val
            20                  25                  30

Val Lys Met Leu Gln Glu Asn Ser Glu Leu Met Asn Asn Asn Ser Ser
        35                  40                  45

Glu Gln Val Leu Tyr Val Asp Pro Met Ile Thr Glu Ile Lys Glu Ile
    50                  55                  60

Phe Ile Pro Glu His Lys Pro Thr Asp Tyr Lys Lys Glu Asn Thr Gly
65                  70                  75                  80

```
Pro Leu Glu Thr Arg Asp Tyr Pro Gln Asn Ser Leu Phe Asp Asn Thr
                85                  90                  95

Thr Val Val Tyr Ile Pro Asp Leu Asn Thr Gly Tyr Lys Pro Gln Ile
            100                 105                 110

Ser Asn Phe Leu Pro Glu Gly Ser His Leu Ser Asn Asn Asn Glu Ile
        115                 120                 125

Thr Ser Leu Thr Leu Lys Pro Pro Val Asp Ser Leu Asp Ser Gly Asn
    130                 135                 140

Asn Pro Arg Leu Gln Lys His Pro Asn Phe Ala Phe Ser Val Ser Ser
145                 150                 155                 160

Val Asn Ser Leu Ser Asn Thr Ile Phe Leu Gly Glu Leu Ser Leu Ile
                165                 170                 175

Leu Asn Gln Gly Glu Cys Ser Ser Pro Asp Ile Gln Asn Ser Val Glu
            180                 185                 190

Glu Glu Thr Thr Met Leu Leu Glu Asn Asp Ser Pro Ser Glu Thr Ile
        195                 200                 205

Pro Glu Gln Thr Leu Leu Pro Asp Glu Phe Val Ser Cys Leu Gly Ile
    210                 215                 220

Val Asn Glu Glu Leu Pro Ser Ile Asn Thr Tyr Phe Pro Gln Asn Ile
225                 230                 235                 240

Leu Glu Ser His Phe Asn Arg Ile Ser Leu Leu Glu Lys
                245                 250

<210> SEQ ID NO 57
<211> LENGTH: 22
<212> TYPE: PRT
<213> ORGANISM: Homo sapiens

<400> SEQUENCE: 57

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 58
<211> LENGTH: 21
<212> TYPE: PRT
<213> ORGANISM: Homo sapiens

<400> SEQUENCE: 58

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 59
<211> LENGTH: 21
<212> TYPE: PRT
<213> ORGANISM: Homo sapiens

<400> SEQUENCE: 59

Ile Leu Val Ile Phe Ser Gly Met Phe Leu Val Phe Thr Leu Ala Gly
1               5                   10                  15

Ala Leu Phe Leu His
            20

<210> SEQ ID NO 60
<211> LENGTH: 27
<212> TYPE: PRT
```

<213> ORGANISM: Homo sapiens

<400> SEQUENCE: 60

Phe Trp Val Leu Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 61
<211> LENGTH: 27
<212> TYPE: PRT
<213> ORGANISM: Homo sapiens

<400> SEQUENCE: 61

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 62
<211> LENGTH: 21
<212> TYPE: PRT
<213> ORGANISM: Homo sapiens

<400> SEQUENCE: 62

Val Gly Val Val Gly Gly Leu Leu Gly Ser Leu Val Leu Leu Val Trp
1               5                   10                  15

Val Leu Ala Val Ile
            20

<210> SEQ ID NO 63
<211> LENGTH: 21
<212> TYPE: PRT
<213> ORGANISM: Homo sapiens

<400> SEQUENCE: 63

Thr His Leu Val Ile Leu Gly Ala Ile Leu Leu Cys Leu Gly Val Ala
1               5                   10                  15

Leu Thr Phe Ile Phe
            20

<210> SEQ ID NO 64
<211> LENGTH: 40
<212> TYPE: PRT
<213> ORGANISM: Homo sapiens

<400> SEQUENCE: 64

Cys Val Arg Cys Arg His Arg Arg Gln Ala Glu Arg Met Ser Gln
1               5                   10                  15

Ile Lys Arg Leu Leu Ser Glu Lys Lys Thr Cys Gln Cys Pro His Arg
            20                  25                  30

Phe Gln Lys Thr Cys Ser Pro Ile
            35                  40

<210> SEQ ID NO 65
<211> LENGTH: 32
<212> TYPE: PRT
<213> ORGANISM: Homo sapiens

<400> SEQUENCE: 65

Leu Tyr Cys Asn His Arg Asn Arg Arg Arg Val Cys Lys Cys Pro Arg
1               5                   10                  15

```
Pro Val Val Lys Ser Gly Asp Lys Pro Ser Leu Ser Ala Arg Tyr Val
            20                  25                  30
```

<210> SEQ ID NO 66
<211> LENGTH: 48
<212> TYPE: PRT
<213> ORGANISM: Homo sapiens

<400> SEQUENCE: 66

```
Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45
```

<210> SEQ ID NO 67
<211> LENGTH: 41
<212> TYPE: PRT
<213> ORGANISM: Homo sapiens

<400> SEQUENCE: 67

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 68
<211> LENGTH: 42
<212> TYPE: PRT
<213> ORGANISM: Homo sapiens

<400> SEQUENCE: 68

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 69
<211> LENGTH: 97
<212> TYPE: PRT
<213> ORGANISM: Homo sapiens

<400> SEQUENCE: 69

```
Cys Ser Arg Ala Ala Arg Gly Thr Ile Gly Ala Arg Arg Thr Gly Gln
1               5                   10                  15

Pro Leu Lys Glu Asp Pro Ser Ala Val Pro Val Phe Ser Val Asp Tyr
            20                  25                  30

Gly Glu Leu Asp Phe Gln Trp Arg Glu Lys Thr Pro Glu Pro Pro Val
        35                  40                  45

Pro Cys Val Pro Glu Gln Thr Glu Tyr Ala Thr Ile Val Phe Pro Ser
    50                  55                  60

Gly Met Gly Thr Ser Ser Pro Ala Arg Arg Gly Ser Ala Asp Gly Pro
65                  70                  75                  80

Arg Ser Ala Gln Pro Leu Arg Pro Glu Asp Gly His Cys Ser Trp Pro
```

```
                85                  90                  95

Leu

<210> SEQ ID NO 70
<211> LENGTH: 31
<212> TYPE: PRT
<213> ORGANISM: Homo sapiens

<400> SEQUENCE: 70

Arg Leu Arg Lys Gly Arg Met Met Asp Val Lys Lys Cys Gly Ile Gln
1               5                   10                  15

Asp Thr Asn Ser Lys Lys Gln Ser Asp Thr His Leu Glu Glu Thr
                20                  25                  30

<210> SEQ ID NO 71
<211> LENGTH: 153
<212> TYPE: PRT
<213> ORGANISM: Homo sapiens

<400> SEQUENCE: 71

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
        50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 72
<211> LENGTH: 212
<212> TYPE: PRT
<213> ORGANISM: Homo sapiens

<400> SEQUENCE: 72

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
        50                  55                  60

Ser Ala Leu Arg Lys Glu Thr Cys Asn Lys Ser Asn Met Cys Glu Ser
65                  70                  75                  80
```

```
Ser Lys Glu Ala Leu Ala Glu Asn Asn Leu Asn Leu Pro Lys Met Ala
             85                  90                  95

Glu Lys Asp Gly Cys Phe Gln Ser Gly Phe Asn Glu Glu Thr Cys Leu
        100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 73
<211> LENGTH: 177
<212> TYPE: PRT
<213> ORGANISM: Homo sapiens

<400> SEQUENCE: 73

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 74
<211> LENGTH: 219
<212> TYPE: PRT
<213> ORGANISM: Homo sapiens

<400> SEQUENCE: 74

Met Cys Pro Ala Arg Ser Leu Leu Leu Val Ala Thr Leu Val Leu Leu
```

-continued

```
1               5                   10                  15
Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
            35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
            115                 120                 125

Glu Asp Leu Lys Met Tyr Gln Val Glu Phe Lys Thr Met Asn Ala Lys
            130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190

Ile Lys Leu Cys Ile Leu Leu His Ala Phe Arg Ile Arg Ala Val Thr
            195                 200                 205

Ile Asp Arg Val Met Ser Tyr Leu Asn Ala Ser
            210                 215

<210> SEQ ID NO 75
<211> LENGTH: 162
<212> TYPE: PRT
<213> ORGANISM: Homo sapiens

<400> SEQUENCE: 75

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
            115                 120                 125

Thr Glu Ser Gly Cys Lys Glu Cys Glu Glu Leu Glu Glu Lys Asn Ile
            130                 135                 140

Lys Glu Phe Leu Gln Ser Phe Val His Ile Val Gln Met Phe Ile Asn
145                 150                 155                 160
```

Thr Ser

<210> SEQ ID NO 76
<211> LENGTH: 155
<212> TYPE: PRT
<213> ORGANISM: Homo sapiens

<400> SEQUENCE: 76

Met Glu Arg Ile Val Ile Cys Leu Met Val Ile Phe Leu Gly Thr Leu
1               5                   10                  15

Val His Lys Ser Ser Gln Gly Gln Asp Arg His Met Ile Arg Met
        20                  25                  30

Arg Gln Leu Ile Asp Ile Val Asp Gln Leu Lys Asn Tyr Val Asn Asp
            35                  40                  45

Leu Val Pro Glu Phe Leu Pro Ala Pro Glu Asp Val Glu Thr Asn Cys
    50                  55                  60

Glu Trp Ser Ala Phe Ser Cys Phe Gln Lys Ala Gln Leu Lys Ser Ala
65                  70                  75                  80

Asn Thr Gly Asn Asn Glu Arg Ile Ile Asn Val Ser Ile Lys Lys Leu
                85                  90                  95

Lys Arg Lys Pro Pro Ser Thr Asn Ala Gly Arg Arg Gln Lys His Arg
            100                 105                 110

Leu Thr Cys Pro Ser Cys Asp Ser Tyr Glu Lys Lys Pro Pro Lys Glu
        115                 120                 125

Phe Leu Glu Arg Phe Lys Ser Leu Leu Gln Lys Met Ile His Gln His
    130                 135                 140

Leu Ser Ser Arg Thr His Gly Ser Glu Asp Ser
145                 150                 155

<210> SEQ ID NO 77
<211> LENGTH: 189
<212> TYPE: PRT
<213> ORGANISM: Homo sapiens

<400> SEQUENCE: 77

Met Leu Gly Ser Arg Ala Val Met Leu Leu Leu Leu Leu Pro Trp Thr
1               5                   10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His
        35                  40                  45

Pro Leu Val Gly His Met Asp Leu Arg Glu Glu Gly Asp Glu Glu Thr
    50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala 165                 170                 175

Ala Arg Val Phe Ala His Gly Ala Ala Thr Leu Ser Pro
            180                 185

<210> SEQ ID NO 78
<211> LENGTH: 270
<212> TYPE: PRT
<213> ORGANISM: Homo sapiens

<400> SEQUENCE: 78

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270

<210> SEQ ID NO 79
<211> LENGTH: 177
<212> TYPE: PRT
<213> ORGANISM: Homo sapiens

<400> SEQUENCE: 79

Gly Pro Gln Arg Glu Glu Phe Pro Arg Asp Leu Ser Leu Ile Ser Pro
1               5                   10                  15

Leu Ala Gln Ala Val Arg Ser Ser Ser Arg Thr Pro Ser Asp Lys Pro
            20                  25                  30

Val Ala His Val Val Ala Asn Pro Gln Ala Glu Gly Gln Leu Gln Trp

```
            35                  40                  45
Leu Asn Arg Arg Ala Asn Ala Leu Leu Ala Asn Gly Val Glu Leu Arg
 50                  55                  60

Asp Asn Gln Leu Val Val Pro Ser Glu Gly Leu Tyr Leu Ile Tyr Ser
 65                  70                  75                  80

Gln Val Leu Phe Lys Gly Gln Gly Cys Pro Ser Thr His Val Leu Leu
                 85                  90                  95

Thr His Thr Ile Ser Arg Ile Ala Val Ser Tyr Gln Thr Lys Val Asn
                100                 105                 110

Leu Leu Ser Ala Ile Lys Ser Pro Cys Gln Arg Glu Thr Pro Glu Gly
            115                 120                 125

Ala Glu Ala Lys Pro Trp Tyr Glu Pro Ile Tyr Leu Gly Gly Val Phe
        130                 135                 140

Gln Leu Glu Lys Gly Asp Arg Leu Ser Ala Glu Ile Asn Arg Pro Asp
    145                 150                 155                 160

Tyr Leu Asp Phe Ala Glu Ser Gly Gln Val Tyr Phe Gly Ile Ile Ala
                165                 170                 175

Leu
```

<210> SEQ ID NO 80
<211> LENGTH: 205
<212> TYPE: PRT
<213> ORGANISM: Homo sapiens

<400> SEQUENCE: 80

```
Met Thr Pro Pro Glu Arg Leu Phe Leu Pro Arg Val Cys Gly Thr Thr
  1               5                  10                  15

Leu His Leu Leu Leu Leu Gly Leu Leu Leu Val Leu Leu Pro Gly Ala
                 20                  25                  30

Gln Gly Leu Pro Gly Val Gly Leu Thr Pro Ser Ala Ala Gln Thr Ala
             35                  40                  45

Arg Gln His Pro Lys Met His Leu Ala His Ser Thr Leu Lys Pro Ala
 50                  55                  60

Ala His Leu Ile Gly Asp Pro Ser Lys Gln Asn Ser Leu Leu Trp Arg
 65                  70                  75                  80

Ala Asn Thr Asp Arg Ala Phe Leu Gln Asp Gly Phe Ser Leu Ser Asn
                 85                  90                  95

Asn Ser Leu Leu Val Pro Thr Ser Gly Ile Tyr Phe Val Tyr Ser Gln
                100                 105                 110

Val Val Phe Ser Gly Lys Ala Tyr Ser Pro Lys Ala Thr Ser Ser Pro
            115                 120                 125

Leu Tyr Leu Ala His Glu Val Gln Leu Phe Ser Ser Gln Tyr Pro Phe
        130                 135                 140

His Val Pro Leu Leu Ser Ser Gln Lys Met Val Tyr Pro Gly Leu Gln
    145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
                180                 185                 190

Leu Ser Pro Ser Thr Val Phe Phe Gly Ala Phe Ala Leu
            195                 200                 205
```

<210> SEQ ID NO 81
<211> LENGTH: 74
<212> TYPE: PRT

<213> ORGANISM: Homo sapiens

<400> SEQUENCE: 81

```
Gly Ile Ile Gln His Asp Leu Ile Phe Ser Leu Gln Gln Thr Glu Cys
1               5                   10                  15

Val Leu Lys Pro Val Glu Ser Ser Asp Met Lys Met Thr Gln Leu Phe
            20                  25                  30

Thr Lys Val Glu Ser Glu Asp Thr Ser Ser Leu Phe Asp Lys Leu Lys
        35                  40                  45

Lys Glu Pro Asp Ala Leu Thr Leu Leu Ala Pro Ala Ala Gly Asp Thr
    50                  55                  60

Ile Ile Ser Leu Asp Phe Gly Ser Asn Asp
65                  70
```

<210> SEQ ID NO 82
<211> LENGTH: 224
<212> TYPE: PRT
<213> ORGANISM: Homo sapiens

<400> SEQUENCE: 82

```
Ser Glu Asp Thr Ser Ser Leu Phe Asp Lys Leu Lys Lys Glu Pro Asp
1               5                   10                  15

Ala Leu Thr Leu Leu Ala Pro Ala Ala Gly Asp Thr Ile Ile Ser Leu
            20                  25                  30

Asp Phe Gly Ser Asn Asp Thr Glu Thr Asp Asp Gln Gln Leu Glu Glu
        35                  40                  45

Val Pro Leu Tyr Asn Asp Val Met Leu Pro Ser Pro Asn Glu Lys Leu
    50                  55                  60

Gln Asn Ile Asn Leu Ala Met Ser Pro Leu Pro Thr Ala Glu Thr Pro
65                  70                  75                  80

Lys Pro Leu Arg Ser Ser Ala Asp Pro Ala Leu Asn Gln Glu Val Ala
                85                  90                  95

Leu Lys Leu Glu Pro Asn Pro Glu Ser Leu Glu Leu Ser Phe Thr Met
            100                 105                 110

Pro Gln Ile Gln Asp Gln Thr Pro Ser Pro Ser Asp Gly Ser Thr Arg
        115                 120                 125

Gln Ser Ser Pro Glu Pro Asn Ser Pro Ser Glu Tyr Cys Phe Tyr Val
    130                 135                 140

Asp Ser Asp Met Val Asn Glu Phe Lys Leu Glu Leu Val Glu Lys Leu
145                 150                 155                 160

Phe Ala Glu Asp Thr Glu Ala Lys Asn Pro Phe Ser Thr Gln Asp Thr
                165                 170                 175

Asp Leu Asp Leu Glu Met Leu Ala Pro Tyr Ile Pro Met Asp Asp Asp
            180                 185                 190

Phe Gln Leu Arg Ser Phe Asp Gln Leu Ser Pro Leu Glu Ser Ser Ser
        195                 200                 205

Ala Ser Pro Glu Ser Ala Ser Pro Gln Ser Thr Val Thr Val Phe Gln
    210                 215                 220
```

<210> SEQ ID NO 83
<211> LENGTH: 10
<212> TYPE: PRT
<213> ORGANISM: Artificial Sequence
<220> FEATURE:
<223> OTHER INFORMATION: Syntheized

<400> SEQUENCE: 83

-continued

Gly Gly Gly Gly Ser Gly Gly Gly Gly Ser
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Syntheized

<400> SEQUENCE: 84

Glu Ala Ala Ala Arg Glu Ala Ala Ala Arg
1               5                   10

<210> SEQ ID NO 85
<211> LENGTH: 705
<212> TYPE: DNA
<213> ORGANISM: Homo sapiens

<400> SEQUENCE: 85

```
atgacagtgc tggcgccagc ctggagccca acaacctatc tcctcctgct gctgctgctg    60
agctcgggac tcagtgggac ccaggactgc tccttccaac acagccccat ctcctccgac   120
ttcgctgtca aaatccgtga gctgtctgac tacctgcttc aagattaccc agtcaccgtg   180
gcctccaacc tgcaggacga ggagctctgc gggggcctct ggcggctggt cctggcacag   240
cgctggatgg agcggctcaa gactgtcgct gggtccaaga tgcaaggctt gctggagcgc   300
gtgaacacgg agatacactt tgtcaccaaa tgtgcctttc agcccccccc cagctgtctt   360
cgcttcgtcc agaccaacat ctcccgcctc ctgcaggaga cctccgagca gctggtggcg   420
ctgaagccct ggatcactcg ccagaacttc tcccggtgcc tggagctgca gtgtcagccc   480
gactcctcaa ccctgccacc cccatggagt ccccggcccc tggaggccac agccccgaca   540
gccccgcagc cccctctgct cctcctactg ctgctgcccg tgggcctcct gctgctggcc   600
gctgctggt gcctgcactg gcagaggacg cggcggagga caccccgccc tggggagcag   660
gtgccccccg tccccagtcc ccaggacctg ctgcttgtgg agcac                   705
```

<210> SEQ ID NO 86
<211> LENGTH: 534
<212> TYPE: DNA
<213> ORGANISM: Homo sapiens

<400> SEQUENCE: 86

```
atgacagtgc tggcgccagc ctggagccca acaacctatc tcctcctgct gctgctgctg    60
agctcgggac tcagtgggac ccaggactgc tccttccaac acagccccat ctcctccgac   120
ttcgctgtca aaatccgtga gctgtctgac tacctgcttc aagattaccc agtcaccgtg   180
gcctccaacc tgcaggacga ggagctctgc gggggcctct ggcggctggt cctggcacag   240
cgctggatgg agcggctcaa gactgtcgct gggtccaaga tgcaaggctt gctggagcgc   300
gtgaacacgg agatacactt tgtcaccaaa tgtgcctttc agcccccccc cagctgtctt   360
cgcttcgtcc agaccaacat ctcccgcctc ctgcaggaga cctccgagca gctggtggcg   420
ctgaagccct ggatcactcg ccagaacttc tcccggtgcc tggagctgca gtgtcagccc   480
gtagagacgg tgtttcaccg tgtcagccag gatggtctcg atctcctgac ctcg         534
```

<210> SEQ ID NO 87
<211> LENGTH: 552
<212> TYPE: DNA
<213> ORGANISM: Homo sapiens

<400> SEQUENCE: 87

```
atgacagtgc tggcgccagc ctggagccca acaacctatc tcctcctgct gctgctgctg      60
agctcgggac tcagtgggac ccaggactgc tccttccaac acagcccccat ctcctccgac    120 ttcgctgtca aaatccgtga gctgtctgac tacctgcttc aagattaccc agtcaccgtg    180
gcctccaacc tgcaggacga ggagctctgc ggggggcctct ggcggctggt cctggcacag    240
cgctggatgg agcggctcaa gactgtcgct gggtccaaga tgcaaggctt gctggagcgc    300
gtgaacacgg agatacactt tgtcaccaaa tgtgcctttc agcccccccc cagctgtctt    360
cgcttcgtcc agaccaacat ctcccgcctc ctgcaggaga cctccgagca gctggtggcg    420
ctgaagccct ggatcactcg ccagaacttc tcccggtgcc tggagctgca gtgtcagccc    480
gactcctcaa ccctgccacc cccatggagt cccggcccc tggaggccac agccccgaca    540
gccccgcagc cc                                                       552
```

<210> SEQ ID NO 88
<211> LENGTH: 207
<212> TYPE: DNA
<213> ORGANISM: Homo sapiens

<400> SEQUENCE: 88

```
accacgacgc cagcgccgcg accaccaaca ccggcgccca ccatcgcgtc gcagcccctg     60
tccctgcgcc cagaggcgtg ccggccagcg gcgggggggcg cagtgcacac gaggggggctg  120 gacttcgcct gtgatatcta catctgggcg cccttggccg ggacttgtgg ggtccttctc    180
ctgtcactgg ttatcaccct ttactgc                                        207
```

<210> SEQ ID NO 89
<211> LENGTH: 432
<212> TYPE: DNA
<213> ORGANISM: Homo sapiens

<400> SEQUENCE: 89

```
atgtggctgc agagcctgct gctcttgggc actgtggcct gcagcatctc tgcacccgcc      60
cgctcgccca gccccagcac gcagccctgg gagcatgtga atgccatcca ggaggcccgg    120
cgtctcctga acctgagtag agacactgct gctgagatga atgaaacagt agaagtcatc    180
tcagaaatgt ttgacctcca ggagccgacc tgcctacaga cccgcctgga gctgtacaag    240
cagggcctgc ggggcagcct caccaagctc aagggcccct tgaccatgat ggccagccac    300
tacaagcagc actgccctcc aaccccggaa acttcctgtg caacccagat tatcaccttt    360
gaaagtttca agagaaacct gaaggacttt ctgcttgtca tccccttgta ctgctgggag    420
ccagtccagg ag                                                       432
```

<210> SEQ ID NO 90
<211> LENGTH: 471
<212> TYPE: DNA
<213> ORGANISM: Homo sapiens

<400> SEQUENCE: 90

```
atgggcacct ctctgctgtg ctggatggct ctgtgtctgc tgggagctga ccacgccgat      60
gcttgcccct actccaaccc ttctctgtgt agcggaggcg gaggaagcga actgcctacc    120
caaggcacct tctccaacgt gtccaccaac gtgtcccccg ccaagcctac cacaaccgct    180
tgcccttaca gcaaccccctc tctgtgcagc ggaggaggag gatccccgc cccagaccc     240
```

```
cctacacccg cccccaccat cgccagccag cctctgtctc tgagacccga ggcttgcaga    300
cccgctgctg gcggagctgt gcacaccaga ggactggact tcgcttgcga tatctacatc    360
tgggcccctc tggccggaac atgtggagtg ctgctgctgt ctctggtgat cacactgtac    420
tgcaaccata ggaatagaag gagggtgtgt aagtgcccta gacccgtggt g             471
```

<210> SEQ ID NO 91
<211> LENGTH: 1071
<212> TYPE: DNA
<213> ORGANISM: Homo sapiens

<400> SEQUENCE: 91

```
atgcttctcc tggtgacaag ccttctgctc tgtgagttac cacacccagc attcctcctg    60
atcccacgca aagtgtgtaa cggaataggt attggtgaat ttaaagactc actctccata    120
aatgctacga atattaaaca cttcaaaaac tgcacctcca tcagtggcga tctccacatc    180
ctgccggtgg catttagggg tgactccttc acacatactc ctcctctgga tccacaggaa    240
ctggatattc tgaaaaccgt aaaggaaatc acagggtttt tgctgattca ggcttggcct    300
gaaaacagga cggacctcca tgcctttgag aacctagaaa tcatacgcgg caggaccaag    360
caacatggtc agttttctct tgcagtcgtc agcctgaaca taacatcctt gggattacgc    420
tccctcaagg agataagtga tggagatgtg ataatttcag gaaacaaaaa tttgtgctat    480
gcaaatacaa taaactggaa aaaactgttt gggacctccg gtcagaaaac caaaattata    540
agcaacagag gtgaaaacag ctgcaaggcc acaggccagg tctgccatgc cttgtgctcc    600
cccgagggct gctggggccc ggagcccagg gactgcgtct cttgccggaa tgtcagccga    660
ggcagggaat gcgtggacaa gtgcaaccct ctggagggtg agccaaggga gtttgtggag    720
aactctgagt gcatacagtg ccacccagag tgcctgcctc aggccatgaa catcacctgc    780
acaggacggg gaccagacaa ctgtatccag tgtgcccact acattgacgg ccccactgc    840 gtcaagacct gccccggcagg agtcatggga gaaaacaaca ccctggtctg aagtacgca    900 gacgccggcc atgtgtgcca cctgtgccat ccaaactgca cctacggatg cactgggcca    960
ggtcttgaag ctgtccaac gaatgggcct aagatcccgt ccatcgccac tgggatggtg    1020
ggggccctcc tcttgctgct ggtggtggcc ctggggatcg gcctcttcat g             1071
```

<210> SEQ ID NO 92
<211> LENGTH: 45
<212> TYPE: DNA
<213> ORGANISM: Artificial Sequence
<220> FEATURE:
<223> OTHER INFORMATION: Synthesized

<400> SEQUENCE: 92

```
ggtggcggtg gctcgggcgg tggtgggtcg ggtggcggcg gatct                     45
```

<210> SEQ ID NO 93
<211> LENGTH: 390
<212> TYPE: DNA
<213> ORGANISM: Homo sapiens

<400> SEQUENCE: 93

```
tcgaggtcga cggtatcgat aagcttgata tcgaattagg aggaaaaact gtttcataca    60
gaaggcgtca attaggagga aaaactgttt catacagaag gcgtcaatta ggaggaaaaa    120
ctgtttcata cagaaggcgt caattggtcc catcgaatta ggaggaaaaa ctgtttcata    180
cagaaggcgt caattaggag gaaaaactgt ttcatacaga aggcgtcaat taggaggaaa    240
```

```
aactgtttca tacagaaggc gtcaattggt cccgggacat tttgacaccc ccataatatt    300
tttccagaat taacagtata aattgcatct cttgttcaag agttccctat cactctcttt    360
aatcactact cacagtaacc tcaactcctg                                     390
```

<210> SEQ ID NO 94
<211> LENGTH: 235
<212> TYPE: PRT
<213> ORGANISM: Homo sapiens

<400> SEQUENCE: 94

```
Met Thr Val Leu Ala Pro Ala Trp Ser Pro Thr Thr Tyr Leu Leu Leu
1               5                   10                  15

Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
        35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
    130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro Pro Leu Leu Leu Leu Leu Leu Leu
            180                 185                 190

Pro Val Gly Leu Leu Leu Leu Ala Ala Ala Trp Cys Leu His Trp Gln
        195                 200                 205

Arg Thr Arg Arg Arg Thr Pro Arg Pro Gly Glu Gln Val Pro Pro Val
    210                 215                 220

Pro Ser Pro Gln Asp Leu Leu Leu Val Glu His
225                 230                 235
```

<210> SEQ ID NO 95
<211> LENGTH: 178
<212> TYPE: PRT
<213> ORGANISM: Homo sapiens

<400> SEQUENCE: 95

```
Met Thr Val Leu Ala Pro Ala Trp Ser Pro Thr Thr Tyr Leu Leu Leu
1               5                   10                  15

Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
        35                  40                  45

Ser Asp Tyr Leu Leu Gln Asp Tyr Pro Val Thr Val Ala Ser Asn Leu
    50                  55                  60
```

-continued

```
Gln Asp Glu Glu Leu Cys Gly Gly Leu Trp Arg Leu Val Leu Ala Gln
 65                  70                  75                  80

Arg Trp Met Glu Arg Leu Lys Thr Val Ala Gly Ser Lys Met Gln Gly
                 85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
130                 135                 140

Ile Thr Arg Gln Asn Phe Ser Arg Cys Leu Glu Leu Gln Cys Gln Pro
145                 150                 155                 160

Val Glu Thr Val Phe His Arg Val Ser Gln Asp Gly Leu Asp Leu Leu
                165                 170                 175

Thr Ser

<210> SEQ ID NO 96
<211> LENGTH: 184
<212> TYPE: PRT
<213> ORGANISM: Homo sapiens

<400> SEQUENCE: 96

Met Thr Val Leu Ala Pro Ala Trp Ser Pro Thr Thr Tyr Leu Leu Leu
 1               5                  10                  15

Leu Leu Leu Leu Ser Ser Gly Leu Ser Gly Thr Gln Asp Cys Ser Phe
                20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
        50                  55                  60

Gln Asp Glu Glu Leu Cys Gly Gly Leu Trp Arg Leu Val Leu Ala Gln
 65                  70                  75                  80

Arg Trp Met Glu Arg Leu Lys Thr Val Ala Gly Ser Lys Met Gln Gly
                 85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
        115                 120                 125

Arg Leu Leu Gln Glu Thr Ser Glu Gln Leu Val Ala Leu Lys Pro Trp
130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro
            180

<210> SEQ ID NO 97
<211> LENGTH: 69
<212> TYPE: PRT
<213> ORGANISM: Homo sapiens

<400> SEQUENCE: 97

Thr Thr Thr Pro Ala Pro Arg Pro Pro Thr Pro Ala Pro Thr Ile Ala
 1               5                  10                  15
```

```
Ser Gln Pro Leu Ser Leu Arg Pro Glu Ala Cys Arg Pro Ala Ala Gly
             20                  25                  30

Gly Ala Val His Thr Arg Gly Leu Asp Phe Ala Cys Asp Ile Tyr Ile
         35                  40                  45

Trp Ala Pro Leu Ala Gly Thr Cys Gly Val Leu Leu Leu Ser Leu Val
 50                  55                  60

Ile Thr Leu Tyr Cys
 65

<210> SEQ ID NO 98
<211> LENGTH: 144
<212> TYPE: PRT
<213> ORGANISM: Homo sapiens

<400> SEQUENCE: 98

Met Trp Leu Gln Ser Leu Leu Leu Leu Gly Thr Val Ala Cys Ser Ile
 1               5                  10                  15

Ser Ala Pro Ala Arg Ser Pro Ser Pro Ser Thr Gln Pro Trp Glu His
             20                  25                  30

Val Asn Ala Ile Gln Glu Ala Arg Arg Leu Leu Asn Leu Ser Arg Asp
         35                  40                  45

Thr Ala Ala Glu Met Asn Glu Thr Val Glu Val Ile Ser Glu Met Phe
 50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 99
<211> LENGTH: 157
<212> TYPE: PRT
<213> ORGANISM: Homo sapiens

<400> SEQUENCE: 99

Met Gly Thr Ser Leu Leu Cys Trp Met Ala Leu Cys Leu Leu Gly Ala
 1               5                  10                  15

Asp His Ala Asp Ala Cys Pro Tyr Ser Asn Pro Ser Leu Cys Ser Gly
             20                  25                  30

Gly Gly Gly Ser Glu Leu Pro Thr Gln Gly Thr Phe Ser Asn Val Ser
         35                  40                  45

Thr Asn Val Ser Pro Ala Lys Pro Thr Thr Thr Ala Cys Pro Tyr Ser
 50                  55                  60

Asn Pro Ser Leu Cys Ser Gly Gly Gly Gly Ser Pro Ala Pro Arg Pro
 65                  70                  75                  80

Pro Thr Pro Ala Pro Thr Ile Ala Ser Gln Pro Leu Ser Leu Arg Pro
                 85                  90                  95

Glu Ala Cys Arg Pro Ala Ala Gly Gly Ala Val His Thr Arg Gly Leu
            100                 105                 110

Asp Phe Ala Cys Asp Ile Tyr Ile Trp Ala Pro Leu Ala Gly Thr Cys
        115                 120                 125
```

```
Gly Val Leu Leu Ser Leu Val Ile Thr Leu Tyr Cys Asn His Arg
130                 135                 140

Asn Arg Arg Arg Val Cys Lys Cys Pro Arg Pro Val Val
145                 150                 155
```

<210> SEQ ID NO 100
<211> LENGTH: 357
<212> TYPE: PRT
<213> ORGANISM: Homo sapiens

<400> SEQUENCE: 100

```
Met Leu Leu Leu Val Thr Ser Leu Leu Cys Glu Leu Pro His Pro
1               5                   10                  15

Ala Phe Leu Leu Ile Pro Arg Lys Val Cys Asn Gly Ile Gly Ile
                20                  25                  30

Glu Phe Lys Asp Ser Leu Ser Ile Asn Ala Thr Asn Ile Lys His Phe
            35                  40                  45

Lys Asn Cys Thr Ser Ile Ser Gly Asp Leu His Ile Leu Pro Val Ala
        50                  55                  60

Phe Arg Gly Asp Ser Phe Thr His Thr Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
                100                 105                 110

Glu Ile Ile Arg Gly Arg Thr Lys Gln His Gly Gln Phe Ser Leu Ala
                115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
                180                 185                 190

Gln Val Cys His Ala Leu Cys Ser Pro Glu Gly Cys Trp Gly Pro Glu
                195                 200                 205

Pro Arg Asp Cys Val Ser Cys Arg Asn Val Ser Arg Gly Arg Glu Cys
210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
                260                 265                 270

His Tyr Ile Asp Gly Pro His Cys Val Lys Thr Cys Pro Ala Gly Val
                275                 280                 285

Met Gly Glu Asn Asn Thr Leu Val Trp Lys Tyr Ala Asp Ala Gly His
                290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
                340                 345                 350
```

```
Ile Gly Leu Phe Met
        355
```

<210> SEQ ID NO 101
<211> LENGTH: 15
<212> TYPE: PRT
<213> ORGANISM: Artificial Sequence
<220> FEATURE:
<223> OTHER INFORMATION: Synthesized

<400> SEQUENCE: 101

```
Gly Gly Gly Gly Ser Gly Gly Gly Gly Ser Gly Gly Gly Gly Ser
1               5                   10                  15
```

<210> SEQ ID NO 102
<211> LENGTH: 21
<212> TYPE: RNA
<213> ORGANISM: Artificial Sequence
<220> FEATURE:
<223> OTHER INFORMATION: Synthesized

<400> SEQUENCE: 102
ggaaaaugga gaagaauuau u           21

<210> SEQ ID NO 103
<211> LENGTH: 21
<212> TYPE: RNA
<213> ORGANISM: Artificial Sequence
<220> FEATURE:
<223> OTHER INFORMATION: Synthesized

<400> SEQUENCE: 103
uaauucuucu ccauuuuccu u           21

<210> SEQ ID NO 104
<211> LENGTH: 21
<212> TYPE: RNA
<213> ORGANISM: Artificial Sequence
<220> FEATURE:
<223> OTHER INFORMATION: Synthesized

<400> SEQUENCE: 104
caucaaguau ggacauuuau u           21

<210> SEQ ID NO 105
<211> LENGTH: 21
<212> TYPE: RNA
<213> ORGANISM: Artificial Sequence
<220> FEATURE:
<223> OTHER INFORMATION: Synthesized

<400> SEQUENCE: 105
uaaaugucca uacuugaugu u           21

<210> SEQ ID NO 106
<211> LENGTH: 21
<212> TYPE: RNA
<213> ORGANISM: Artificial Sequence
<220> FEATURE:
<223> OTHER INFORMATION: Synthesized

<400> SEQUENCE: 106
auauauggcc cgaguacaau u           21

<210> SEQ ID NO 107

```
<211> LENGTH: 21
<212> TYPE: RNA
<213> ORGANISM: Artificial Sequence
<220> FEATURE:
<223> OTHER INFORMATION: Synthesized

<400> SEQUENCE: 107
uuguacucgg gccauauauu u                                              21

<210> SEQ ID NO 108
<211> LENGTH: 21
<212> TYPE: RNA
<213> ORGANISM: Artificial Sequence
<220> FEATURE:
<223> OTHER INFORMATION: Synthesized

<400> SEQUENCE: 108
gagaagaauu aaaugccauu u                                              21

<210> SEQ ID NO 109
<211> LENGTH: 21
<212> TYPE: RNA
<213> ORGANISM: Artificial Sequence
<220> FEATURE:
<223> OTHER INFORMATION: Synthesized

<400> SEQUENCE: 109
auggcauuua auucuucucu u                                              21

<210> SEQ ID NO 110
<211> LENGTH: 21
<212> TYPE: RNA
<213> ORGANISM: Artificial Sequence
<220> FEATURE:
<223> OTHER INFORMATION: Synthesized

<400> SEQUENCE: 110
guuggaaaau ggagaagaau u                                              21

<210> SEQ ID NO 111
<211> LENGTH: 21
<212> TYPE: RNA
<213> ORGANISM: Artificial Sequence
<220> FEATURE:
<223> OTHER INFORMATION: Synthesized

<400> SEQUENCE: 111
uucuucucca uuuuccaacu u                                              21

<210> SEQ ID NO 112
<211> LENGTH: 21
<212> TYPE: RNA
<213> ORGANISM: Artificial Sequence
<220> FEATURE:
<223> OTHER INFORMATION: Synthesized

<400> SEQUENCE: 112
uucuucucca uuuuccaacu u                                              21

<210> SEQ ID NO 113
<211> LENGTH: 288
<212> TYPE: PRT
<213> ORGANISM: Homo sapiens

<400> SEQUENCE: 113

Met Gly His Thr Arg Arg Gln Gly Thr Ser Pro Ser Lys Cys Pro Tyr
```

```
  1               5                  10                 15
Leu Asn Phe Phe Gln Leu Leu Val Leu Ala Gly Leu Ser His Phe Cys
             20                  25                 30

Ser Gly Val Ile His Val Thr Lys Glu Val Lys Glu Val Ala Thr Leu
             35                  40                 45

Ser Cys Gly His Asn Val Ser Val Glu Glu Leu Ala Gln Thr Arg Ile
 50                  55                  60

Tyr Trp Gln Lys Glu Lys Lys Met Val Leu Thr Met Met Ser Gly Asp
 65                  70                  75                 80

Met Asn Ile Trp Pro Glu Tyr Lys Asn Arg Thr Ile Phe Asp Ile Thr
             85                  90                 95

Asn Asn Leu Ser Ile Val Ile Leu Ala Leu Arg Pro Ser Asp Glu Gly
             100                 105                110

Thr Tyr Glu Cys Val Val Leu Lys Tyr Glu Lys Asp Ala Phe Lys Arg
             115                 120                125

Glu His Leu Ala Glu Val Thr Leu Ser Val Lys Ala Asp Phe Pro Thr
 130                 135                 140

Pro Ser Ile Ser Asp Phe Glu Ile Pro Thr Ser Asn Ile Arg Arg Ile
145                 150                 155                160

Ile Cys Ser Thr Ser Gly Gly Phe Pro Glu Pro His Leu Ser Trp Leu
             165                 170                175

Glu Asn Gly Glu Glu Leu Asn Ala Ile Asn Thr Thr Val Ser Gln Asp
             180                 185                190

Pro Glu Thr Glu Leu Tyr Ala Val Ser Ser Lys Leu Asp Phe Asn Met
             195                 200                205

Thr Thr Asn His Ser Phe Met Cys Leu Ile Lys Tyr Gly His Leu Arg
 210                 215                 220

Val Asn Gln Thr Phe Asn Trp Asn Thr Thr Lys Gln Glu His Phe Pro
225                 230                 235                240

Asp Asn Leu Leu Pro Ser Trp Ala Ile Thr Leu Ile Ser Val Asn Gly
             245                 250                255

Ile Phe Val Ile Cys Cys Leu Thr Tyr Cys Phe Ala Pro Arg Cys Arg
             260                 265                270

Glu Arg Arg Arg Asn Glu Arg Leu Arg Arg Glu Ser Val Arg Pro Val
             275                 280                285

<210> SEQ ID NO 114
<211> LENGTH: 242
<212> TYPE: PRT
<213> ORGANISM: Homo sapiens

<400> SEQUENCE: 114

Met Gly His Thr Arg Arg Gln Gly Thr Ser Pro Ser Lys Cys Pro Tyr
 1               5                  10                 15

Leu Asn Phe Phe Gln Leu Leu Val Leu Ala Gly Leu Ser His Phe Cys
             20                  25                 30

Ser Gly Val Ile His Val Thr Lys Glu Val Lys Glu Val Ala Thr Leu
             35                  40                 45

Ser Cys Gly His Asn Val Ser Val Glu Glu Leu Ala Gln Thr Arg Ile
 50                  55                  60

Tyr Trp Gln Lys Glu Lys Lys Met Val Leu Thr Met Met Ser Gly Asp
 65                  70                  75                 80

Met Asn Ile Trp Pro Glu Tyr Lys Asn Arg Thr Ile Phe Asp Ile Thr
             85                  90                 95
```

```
Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
        130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
210                 215                 220

Val Asn Gln Thr Phe Asn Trp Asn Thr Thr Lys Gln Glu His Phe Pro
225                 230                 235                 240

Asp Asn

<210> SEQ ID NO 115
<211> LENGTH: 69
<212> TYPE: PRT
<213> ORGANISM: Homo sapiens

<400> SEQUENCE: 115

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 116
<211> LENGTH: 263
<212> TYPE: PRT
<213> ORGANISM: Homo sapiens

<400> SEQUENCE: 116

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
```

```
                    100                 105                 110
Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
                195                 200                 205

Thr Thr Asn His Ser Phe Met Cys Leu Ile Lys Tyr Gly His Leu Arg
                210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu
                260

<210> SEQ ID NO 117
<211> LENGTH: 23
<212> TYPE: DNA
<213> ORGANISM: Artificial Sequence
<220> FEATURE:
<223> OTHER INFORMATION: Synthesized

<400> SEQUENCE: 117
aagccatggg ccacacacgg agg                                           23

<210> SEQ ID NO 118
<211> LENGTH: 23
<212> TYPE: DNA
<213> ORGANISM: Artificial Sequence
<220> FEATURE:
<223> OTHER INFORMATION: Synthesized

<400> SEQUENCE: 118
cgtggataac acctatggag agg                                           23

<210> SEQ ID NO 119
<211> LENGTH: 23
<212> TYPE: DNA
<213> ORGANISM: Artificial Sequence
<220> FEATURE:
<223> OTHER INFORMATION: Synthesized

<400> SEQUENCE: 119
acagtgtccg cagaagcaag ggg                                           23

<210> SEQ ID NO 120
<211> LENGTH: 23
<212> TYPE: DNA
<213> ORGANISM: Artificial Sequence
<220> FEATURE:
<223> OTHER INFORMATION: Synthesized

<400> SEQUENCE: 120
gaccaaggaa gtgaaagaag tgg                                           23
```

<210> SEQ ID NO 121
<211> LENGTH: 23
<212> TYPE: DNA
<213> ORGANISM: Artificial Sequence
<220> FEATURE:
<223> OTHER INFORMATION: Synthesized

<400> SEQUENCE: 121
gctctgcgcc catctgacga ggg                                           23

<210> SEQ ID NO 122
<211> LENGTH: 867
<212> TYPE: DNA
<213> ORGANISM: Artificial Sequence
<220> FEATURE:
<223> OTHER INFORMATION: Synthesized

<400> SEQUENCE: 122
atgcagatcc cacaggcgcc ctggccagtc gtctgggcgg tgctacaact gggctggcgg    60
ccaggatggt tcttagactc cccagacagg ccctggaacc cccccacctt ctccccagcc   120
ctgctcgtgg tgaccgaagg ggacaacgcc accttcacct gcagcttctc caacacatcg   180
gagagcttcg tgctaaactg gtaccgcatg agccccagca accagacgga caagctggcc   240
gccttccccg aggaccgcag ccagcccggc caggactgcc gcttccgtgt cacacaactg   300
cccaacgggc gtgacttcca catgagcgtg gtcagggccc ggcgcaatga cagcggcacc   360
tacctctgtg gggccatctc cctggccccc aaggcgcaga tcaaagagag cctgcgggca   420
gagctcaggg tgacagagag aagggcagaa gtgcccacag cccaccccag cccctcaccc   480
aggccagccg gccagttcca aaccctggtg gttggtgtcg tgggcggcct gctgggcagc   540
ctggtgctgc tagtctgggt cctggccgtc atctgctccc gggccgcacg agggacaata   600
ggagccaggc gcaccggcca gcccctgaag gaggaccctc agccgtgcc tgtgttctct    660 gtggacgccg gggagctgga tttccagtgg cgagagaaga cccccggagcc ccccgtgccc   720 tgtgtccctg agcagacgga ggccgccacc attgtctttc ctagcggaat gggcacctca   780
tcccccgccc gcaggggctc agctgacggc cctcggagtg cccagccact gaggcctgag   840
gatggacact gctcttggcc cctctga                                       867

<210> SEQ ID NO 123
<211> LENGTH: 621
<212> TYPE: DNA
<213> ORGANISM: Artificial Sequence
<220> FEATURE:
<223> OTHER INFORMATION: Synthesized

<400> SEQUENCE: 123
atgcagatcc cacaggcgcc ctggccagtc gtctgggcgg tgctacaact gggctggcgg    60
ccaggatggt tcttagactc cccagacagg ccctggaacc cccccacctt ctccccagcc   120
ctgctcgtgg tgaccgaagg ggacaacgcc accttcacct gcagcttctc caacacatcg   180
gagagcttcg tgctaaactg gtaccgcatg agccccagca accagacgga caagctggcc   240
gccttccccg aggaccgcag ccagcccggc caggactgcc gcttccgtgt cacacaactg   300
cccaacgggc gtgacttcca catgagcgtg gtcagggccc ggcgcaatga cagcggcacc   360
tacctctgtg gggccatctc cctggccccc aaggcgcaga tcaaagagag cctgcgggca   420
gagctcaggg tgacagagag aagggcagaa gtgcccacag cccaccccag cccctcaccc   480

| | |
|---|---|
| aggccagccg gccagttcca aaccctggtg atcatctcct tctttcttgc gctgacgtcg | 540 |
| actgcgttgc tcttcctgct gttcttcctc acgctccgtt tctctgttgt ttgctcccgg | 600 |
| gccgcacgag ggacaatata a | 621 |

<210> SEQ ID NO 124
<211> LENGTH: 1117
<212> TYPE: DNA
<213> ORGANISM: Homo sapiens

<400> SEQUENCE: 124

| | |
|---|---|
| aatgctttgt cctggagagc tatcttaagg gacaaaatcg ttttcccagc gtcatctgtg | 60 |
| acacatcctg acagtagaga gctgcttcca agaagcaatt tgaagtgcca ttatcaggca | 120 |
| gggacggggg ctctagggga tttcggggtc agcagatatg aaatgaatga tttcataggg | 180 |
| ctgtcacaga gctgtggtgg gaatttccca tgagaccccg cccctggctg agtcaccgca | 240 |
| ctcctgtgtt tgacctgaag tcctctcgag ctgcagaagc ctgaagacca aggagtggaa | 300 |
| agttctccgg cagccctgag atctcaaggt ctgtccatct gggggagtgg gtgggggcac | 360 |
| tgagaagggg tgagattgga acttttgctc cctttgccca tttctagact ttttctccta | 420 |
| atatgtaata acttctcttc aatagccctt taaataaaca tcaataactt agcctgaaga | 480 |
| gttttttcact ccttagtttt gttaccatac aaacttcaca tctcaaaaca tgtctctgtt | 540 |
| taagaaaatg tgttagtgag ttgaacaggg aggtctttcc acatgttagt agttaggtgt | 600 |
| tcagctaaag ggggaagagt gattatgtga tagcttcttc ttgaactgaa ttgtctgatg | 660 |
| cccctgacag attctctttg taaggagttt atttcagggg caataagtaa ttggcattat | 720 |
| tgctggttgg tactgcaaag tacctatgaa agtccccaaa agttcttgct attgttatttt | 780 |
| ctgcattttg gcagaacatg atggaaaatg caccctcaaa cttggcaaa ccggcacaaa | 840 |
| gctgtgtgtt taatcacgcc tgccttgtcc tagtggtttc tatgaatctg ctacttttcc | 900 |
| gtaatattgc atcattaatt gttcctgaaa aaccctgagt tatcctctta tagaattgta | 960 |
| taagtaatga ttgcaatata gataattttg aaaggagaaa ccacctttcc ttggaaatgt | 1020 |
| ttatcttttg cagagtgaca tttgtgagac cagctaattt gattaaaatt ctcttggaat | 1080 |
| cagctttgct agtatcatac ctgtgccaga tttcatc | 1117 |

<210> SEQ ID NO 125
<211> LENGTH: 590
<212> TYPE: DNA
<213> ORGANISM: Artificial Sequence
<220> FEATURE:
<223> OTHER INFORMATION: Synthesized

<400> SEQUENCE: 125

| | |
|---|---|
| agtgaggcgg tacccacaga gccgcgtggc actcctcaac ctgctagagc agccggcctc | 60 |
| ctgcaggatg gcttaaggac cacctggtcc ttggggtctg ggttctccgg gtcctgctgt | 120 |
| tccctgcagc cttccttcta cccccagagc agcttggggg catctttaga gaaagcggca | 180 |
| gtgtcgcacc tgccccagca gccacaaaac agaggaaatt ctgagcacct ccgggcgtga | 240 |
| gtcaccatac cacattcagg aattgccacc tctgcccaca gaatcaccca ctcttttctg | 300 |
| tttgggacca aaatagatac ctccttcaga agccgctgct ttctgtactc tcagcaataa | 360 |
| aaaaacaaag gctaggatag gtgtgtgcct ctgaggcgtg aggggggcg cgttttctcc | 420 |
| cctgggaagg ttttcagaga gaagttgttg ctacagcagt acaggcagct gatgggttga | 480 |
| gggtacagga ggaagaggga tggcctcggc ggccaagctt agacactaga gggtatataa | 540 | tggaagctcg acttccagct tggcaatccg gtactgttgg taaagccacc    590

<210> SEQ ID NO 126
<211> LENGTH: 687
<212> TYPE: DNA
<213> ORGANISM: Artificial Sequence
<220> FEATURE:
<223> OTHER INFORMATION: Synthesized

<400> SEQUENCE: 126
tgagagagga tgatgtattc taaattgaag ttttgattca caagaagatt aaaagccatt    60
cagaaaccta attcacccac tgaaaggaaa aaaaaaaaag agagatgagc agtttgtctc    120
cggaaattgt cttaggtcgg aagtctgtgg tccctgttca catgtaccca aaagcatcct    180
gctgctgcag ctgtctgata agcacagagt accccacctt ctctgcacac tttgcatcta    240
gctcatatta cctcatcttt acttcctttc tgacgtctca ccctggattc tacatataag    300
gtcacacagg aaggaaagct gcattgagtt ttggtgtcct gaaagacttt tgccaacctt    360
gtccccgcac taatttctct aagcctcggc tatactattt tctcagctac acgatgaaat    420
gtgaatgata atttctgccc taaaaatatc acttaatttt ttaacatatc atttatgaaa    480
gaagacacat aaaatgtctc cctaaaatgg aaagttacat attattgcca tctgtgtttt    540
ataaagaggt tgaaagggt ggtacctgag ctcgctagcc tcgaggatat caagatctgg    600
cctcggcggc caagcttaga cactagaggg tatataatgg aagctcgact tccagcttgg    660
caatccggta ctgttggtaa agccacc    687

<210> SEQ ID NO 127
<211> LENGTH: 688
<212> TYPE: DNA
<213> ORGANISM: Artificial Sequence
<220> FEATURE:
<223> OTHER INFORMATION: Synthesized

<400> SEQUENCE: 127
tttctactgg gcagtgctga tctagagcaa tttgaaactt gtggtagata ttttactaac    60
caactctgat gaaggacttc ctcaccaaat tgttctttta accgcattct ttccttgctt    120
tctggtcatt tgcaagaaaa attttaaaag gctgcccctt tgtaaaggtt tgagaggccc    180
tagaatttcg ttttcactt gttcccaacc acaagcaaat gatcaatgtg ctttgtgaat    240
gaagagtcaa cattttacca gggcgaagtg gggaggtaca aaaaaatttc cagtccttga    300
atggtgtgaa gtaaaagtgc cttcaaagaa tcccaccaga atggcacagg tgggcataat    360
gggtctgtct catcgtcaaa ggacccaagg agtctaaagg aaactctaac tacaacaccc    420
aaatgccaca aaaccttagt tattaataca aactatcatc cctgcctatc tgtcaccatc    480
tcatcttaaa aaacttgtga aaatacgtaa tcctcaggag acttcaatta ggtataaata    540
ccagcagcca gaggaggtgc agcacattgt tctgatcatc tgaagatcag ctattagaag    600
agaaagatca gttaagtcct ttggacctga tcagcttgat acaagaacta ctgatttcaa    660
cttctttggc ttaattctct cggaaacg    688

<210> SEQ ID NO 128
<211> LENGTH: 277
<212> TYPE: DNA
<213> ORGANISM: Artificial Sequence
<220> FEATURE:
<223> OTHER INFORMATION: Synthesized

<400> SEQUENCE: 128

| | | | | |
|---|---|---|---|---|
| tcgaggtcga | cggtatcgat | aagcttgata | tcgaattagg | aggaaaaact | gtttcataca | 60 |
| gaaggcgtca | attaggagga | aaaactgttt | catacagaag | gcgtcaatta | ggaggaaaaa | 120 |
| ctgtttcata | cagaaggcgt | caattggtcc | catcgaatta | ggaggaaaaa | ctgtttcata | 180 |
| cagaaggcgt | caattaggag | gaaaaactgt | ttcatacaga | aggcgtcaat | taggaggaaa | 240 |
| aactgtttca | tacagaaggc | gtcaattggt | cccggga | | | 277 |

<210> SEQ ID NO 129
<211> LENGTH: 90
<212> TYPE: DNA
<213> ORGANISM: Artificial Sequence
<220> FEATURE:
<223> OTHER INFORMATION: Synthesized

<400> SEQUENCE: 129

| | | | | | | |
|---|---|---|---|---|---|---|
| acgccttctg | tatgaaacag | ttttcctcc | acgccttctg | tatgaaacag | ttttcctcc | 60 |
| acgccttctg | tatgaaacag | ttttcctcc | | | | 90 |

<210> SEQ ID NO 130
<211> LENGTH: 113
<212> TYPE: DNA
<213> ORGANISM: Artificial Sequence
<220> FEATURE:
<223> OTHER INFORMATION: Synthesized

<400> SEQUENCE: 130

| | | | | | | |
|---|---|---|---|---|---|---|
| cattttgaca | cccccataat | attttttccag | aattaacagt | ataaattgca | tctcttgttc | 60 |
| aagagttccc | tatcactctc | tttaatcact | actcacagta | acctcaactc | ctg | 113 |

<210> SEQ ID NO 131
<211> LENGTH: 322
<212> TYPE: DNA
<213> ORGANISM: Artificial Sequence
<220> FEATURE:
<223> OTHER INFORMATION: Synthesized

<400> SEQUENCE: 131

| | | | | | | |
|---|---|---|---|---|---|---|
| ctttcaggta | ggcctgtgcc | ttttcagcg | ggctgcagtt | ctcctgcttg | gcttgagtca | 60 |
| ttcgcatttc | ctgagagctg | ggtagagggg | gagttgtgga | ggagcccatt | ctgaaactga | 120 |
| tctgatattg | caaacccata | cacggaaagg | aagaactgcc | catacgtatt | cgagtcttcc | 180 |
| aatctgactc | cgagcccgca | tcccctcaa | tcgtctcttt | tccccactcc | ccagatcacg | 240 |
| gtgctgcttg | gtccccctca | gagccataga | gaagcagggg | gtgtggccat | ggaggggaaa | 300 |
| cctctgtcac | cagagactttt | ac | | | | 322 |

<210> SEQ ID NO 132
<211> LENGTH: 7849
<212> TYPE: DNA
<213> ORGANISM: Artificial Sequence
<220> FEATURE:
<223> OTHER INFORMATION: Synthesizd

<400> SEQUENCE: 132

| | | | | | | |
|---|---|---|---|---|---|---|
| cggctccggt | gcccgtcagt | gggcagagcg | cacatcgccc | acagtccccg | agaagttggg | 60 |
| gggaggggtc | ggcaattgaa | ccggtgccta | gagaaggtgg | cgcggggtaa | actgggaaag | 120 |
| tgatgtcgtg | tactggctcc | gccttttcc | cgagggtggg | ggagaaccgt | atataagtgc | 180 |
| agtagtcgcc | gtgaacgttc | ttttttcgcaa | cgggtttgcc | gccagaacac | aggatccgcc | 240 |

-continued

```
accatggcct taccagtgac cgccttgctc ctgccgctgg ccttgctgct ccacgccgcc    300
aggccggata tccagatgac ccagagcccg agcagcctga gcgcgagcgt gggtgatcgc    360
gtgaccatta cctgcagggc aagtcaggac attagtaaat atttaaattg gtatcagcag    420
aaaccgggta aagcgccgaa actgttaatt tatcatacat caagattaca ctcaggcgtg    480
ccgtcgcgtt ttagcggctc gggttcgggc accgatttta ccctgaccat ctcgagcttg    540
cagccggagg acttcgccac ctactattgc caacagggta atacgcttcc gtacacgttc    600
ggtcagggca ccaaagtgga gatcaaaggt ggcggtggct cgggcggtgg tgggtcgggt    660
ggcggcggat ctgaggtgca gctggtggag tctgggggag gcttggtaca gcctgggggg    720
tccctgagac tctcctgtgc agcctctgga gtgtccctgc ctgattatgg cgtgtcctgg    780
gtccgccagg ctccagggaa ggggctggag tgggtttcag tgatctgggg cagcgagaca    840
acctactaca cagcgccct gaagtcccga ttcaccatct ccagagacaa tgccaagaac    900
tcactgtatc tgcaaatgaa cagcctgaga gccgaggaca cggctgtgta ttactgtgcg    960
aagcactact actacggcgg cagctacgct atggactact ggggccaagg aaccctggtc    1020
accgtgtcct caaccacgac gccagcgccg cgaccaccaa caccggcgcc caccatcgcg    1080
tcgcagcccc tgtccctgcg cccagaggcg tgccggccag cggcgggggg cgcagtgcac    1140
acgagggggc tggacttcgc ctgtgatatc tacatctggg cgcccttggc cgggacttgt    1200
ggggtccttc tcctgtcact ggttatcacc ctttactgca acggggcag aaagaaactc    1260 ctgtatatat tcaaacaacc atttatgaga ccagtacaaa ctactcaaga ggaagatggc    1320
tgtagctgcc gatttccaga agaagaagaa ggaggatgtg aactgagagt gaagttcagc    1380
aggagcgcag acgccccgc gtaccagcag ggccagaacc agctctataa cgagctcaat    1440
ctaggacgaa gagaggagta cgatgttttg acaagaggc gtggccggga ccctgagatg    1500
gggggaaagc cgagaaggaa gaaccctcag gaaggcctgt acaatgaact gcagaaagat    1560
aagatggcgg aggcctacag tgagattggg atgaaaggcg agcgccggag gggcaagggg    1620
cacgatggcc tttaccaggg tctcagtaca gccaccaagg acacctacga cgcccttcac    1680
atgcaggccc tgccccctcg ctaagtcgac tctagaacta gtaatcaacc tctggattac    1740
aaaatttgtg aaagattgac tggtattctt aactatgttg ctccttttac gctatgtgga    1800
tacgctgctt taatgccttt gtatcatgct attgcttccc gtatggcttt cattttctcc    1860
tccttgtata atcctggtt gctgtctctt tatgaggagt tgtggcccgt tgtcaggcaa    1920
cgtggcgtgg tgtgcactgt gtttgctgac gcaaccccca ctggttgggg cattgccacc    1980
acctgtcagc tcctttccgg gactttcgct ttccccctcc ctattgccac ggcggaactc    2040
atcgccgcct gccttgcccg ctgctggaca ggggctcggc tgttgggcac tgacaattcc    2100
gtggtgttgt cggggaaatc atcgtccttt ccttggctgc tcgcctgtgt tgccacctgg    2160
attctgcgcg gacgtccctt ctgctacgtc ccttcggccc tcaatccagc ggaccttcct    2220
tcccgcggcc tgctgccggc tctgcggcct cttccgcgtc ttcgccttcg ccctcagacg    2280
agtcggatct ccctttgggc cgcctccccg cctgccgcgg aattcgagct cggtaccttt    2340
aagaccaatg acttacaagg cagctgtaga tcttagccac tttttaaaag aaaagggggg    2400
actggaaggg ctaattcact cccaacgaag acaagatctg cttttttgctt gtactgggtc    2460 tctctggtta gaccagatct gagcctggga gctctctggc taactaggga acccactgct    2520
taagcctcaa taaagcttgc cttgagtgct tcaagtagtg tgtgcccgtc tgttgtgtga    2580
```

-continued

| | | | | |
|---|---|---|---|---|
| ctctggtaac | tagagatccc | tcagaccctt | ttagtcagtg | tggaaaatct ctagcagtag | 2640 |
| tagttcatgt | catcttatta | ttcagtattt | ataacttgca | aagaaatgaa tatcagagag | 2700 |
| tgagaggaac | ttgtttattg | cagcttataa | tggttacaaa | taaagcaata gcatcacaaa | 2760 |
| tttcacaaat | aaagcatttt | tttcactgca | ttctagttgt | ggtttgtcca aactcatcaa | 2820 |
| tgtatcttat | catgtctggc | tctagctatc | ccgcccctaa | ctccgcccat cccgccccta | 2880 |
| actccgccca | gttccgccca | ttctccgccc | atggctgac | taatttttttt tatttatgca | 2940 |
| gaggccgagg | ccgcctcggc | ctctgagcta | ttccagaagt | agtgaggagg ctttttttgga | 3000 |
| ggcctaggga | cgtacccaat | tcgccctata | gtgagtcgta | ttacgcgcgc tcactggccg | 3060 |
| tcgttttaca | acgtcgtgac | tgggaaaacc | ctggcgttac | ccaacttaat cgccttgcag | 3120 |
| cacatccccc | tttcgccagc | tggcgtaata | gcgaagaggc | ccgcaccgat cgcccttccc | 3180 |
| aacagttgcg | cagcctgaat | ggcgaatggg | acgcgccctg | tagcggcgca ttaagcgcgg | 3240 |
| cgggtgtggt | ggttacgcgc | agcgtgaccg | ctacacttgc | cagcgcccta gcgcccgctc | 3300 |
| ctttcgcttt | cttcccttcc | tttctcgcca | cgttcgccgg | ctttccccgt caagctctaa | 3360 |
| atcgggggct | ccctttaggg | ttccgattta | gtgctttacg | gcacctcgac cccaaaaaac | 3420 |
| ttgattaggg | tgatggttca | cgtagtgggc | catcgccctg | atagacggtt tttcgccctt | 3480 |
| tgacgttgga | gtccacgttc | tttaatagtg | gactcttgtt | ccaaactgga acaacactca | 3540 |
| accctatctc | ggtctattct | tttgatttat | aagggatttt | gccgatttcg gcctattggt | 3600 |
| taaaaatga | gctgatttaa | caaaaattta | acgcgaattt | taacaaaata ttaacgctta | 3660 |
| caatttaggt | ggcactttc | ggggaaatgt | gcgcggaacc | cctatttgtt tattttcta | 3720 |
| aatacattca | aatatgtatc | cgctcatgag | acaataaccc | tgataaatgc ttcaataata | 3780 |
| ttgaaaagg | aagagtatga | gccatattca | acgggaaacg | tcttgctcta ggccgcgatt | 3840 |
| aaattccaac | atggatgctg | atttatatgg | gtataaatgg | gctcgcgata atgtcgggca | 3900 |
| atcaggtgcg | acaatctatc | gattgtatgg | gaagcccgat | gcgccagagt tgtttctgaa | 3960 |
| acatggcaaa | ggtagcgttg | ccaatgatgt | tacagatgag | atggtcagac taaactggct | 4020 |
| gacggaattt | atgcctcttc | cgaccatcaa | gcatttttatc | cgtactcctg atgatgcatg | 4080 |
| gttactcacc | actgcgatcc | ccgggaaaac | agcattccag | gtattagaag aatatcctga | 4140 |
| ttcaggtgaa | aatattgttg | atgcgctggc | agtgttcctg | cgccggttgc attcgattcc | 4200 |
| tgtttgtaat | tgtcctttta | acagcgatcg | cgtatttcgt | ctggctcagg cgcaatcacg | 4260 |
| aatgaataac | ggtttggttg | atgcgagtga | ttttgatgac | gagcgtaatg gctggcctgt | 4320 |
| tgaacaagtc | tggaaagaaa | tgcataaact | tttgccattc | tcaccggatt cagtcgtcac | 4380 |
| tcatggtgat | ttctcacttg | ataaccttat | ttttgacgag | gggaaattaa taggttgtat | 4440 |
| tgatgttgga | cgagtcggaa | tcgcagaccg | ataccaggat | cttgccatcc tatggaactg | 4500 |
| cctcggtgag | ttttctcctt | cattacagaa | acgctttttt | caaaaatatg gtattgataa | 4560 |
| tcctgatatg | aataaattgc | agtttcattt | gatgctcgat | gagttttttct aactgtcaga | 4620 |
| ccaagtttac | tcatatatac | tttagattga | tttaaaactt | catttttaat ttaaaaggat | 4680 |
| ctaggtgaag | atcctttttg | ataatctcat | gaccaaaatc | ccttaacgtg agttttcgtt | 4740 |
| ccactgagcg | tcagaccccg | tagaaaagat | caaaggatct | tcttgagatc ctttttttct | 4800 |
| gcgcgtaatc | tgctgcttgc | aaacaaaaaa | accaccgcta | ccagcggtgg tttgtttgcc | 4860 |
| ggatcaagag | ctaccaactc | tttttccgaa | ggtaactggc | ttcagcagag cgcagatacc | 4920 |
| aaatactgtt | cttctagtgt | agccgtagtt | aggccaccac | ttcaagaact ctgtagcacc | 4980 |

```
gcctacatac ctcgctctgc taatcctgtt accagtggct gctgccagtg gcgataagtc    5040
gtgtcttacc gggttggact caagacgata gttaccggat aaggcgcagc ggtcgggctg    5100
aacggggggt tcgtgcacac agcccagctt ggagcgaacg acctacaccg aactgagata    5160
cctacagcgt gagctatgag aaagcgccac gcttcccgaa gggagaaagg cggacaggta    5220
tccggtaagc ggcagggtcg aacaggaga gcgcacgagg gagcttccag ggggaaacgc     5280
ctggtatctt tatagtcctg tcgggtttcg ccacctctga cttgagcgtc gattttgtg     5340 atgctcgtca ggggggcgga gcctatggaa aaacgccagc aacgcggcct ttttacggtt    5400
cctggccttt tgctggcctt tgctcacat gttctttcct gcgttatccc ctgattctgt     5460
ggataaccgt attaccgcct ttgagtgagc tgataccgct cgccgcagcc gaacgaccga    5520
gcgcagcgag tcagtgagcg aggaagcgga agagcgccca atacgcaaac cgcctctccc    5580
cgcgcgttgg ccgattcatt aatgcagctg gcacgacagg tttcccgact ggaaagcggg    5640
cagtgagcgc aacgcaatta atgtgagtta gctcactcat taggcacccc aggctttaca    5700
ctttatgctt ccggctcgta tgttgtgtgg aattgtgagc ggataacaat ttcacacagg    5760
aaacagctat gaccatgatt acgccaagcg cgcaattaac cctcactaaa gggaacaaaa    5820
gctggagctg caagcttaat gtagtcttat gcaatactct tgtagtcttg caacatggta    5880
acgatgagtt agcaacatgc cttcaaagga gagaaaagc accgtgcatg ccgattggtg     5940
gaagtaaggt ggtacgatcg tgccttatta ggaaggcaac agacgggtct gacatggatt    6000
ggacgaacca ctgaattgcc gcattgcaga gatattgtat ttaagtgcct agctcgatac    6060
ataaacgggt ctctctggtt agaccagatc tgagcctggg agctctctgg ctaactaggg    6120
aacccactgc ttaagcctca ataaagcttg ccttgagtgc ttcaagtagt gtgtgcccgt    6180
ctgttgtgtg actctggtaa ctagagatcc ctcagaccct tttagtcagt gtggaaaatc    6240
tctagcagtg gcgcccgaac agggacttga aagcgaaagg gaaaccagag gagctctctc    6300
gacgcaggac tcggcttgct gaagcgcgca cggcaagagg cgaggggcgg cgactggtga    6360
gtacgccaaa aatttttgact agcggaggct agaaggagag agatgggtgc gagagcgtca    6420
gtattaagcg ggggagaatt agatcgcgat gggaaaaaat tcggttaagg ccaggggga     6480 agaaaaaata taattaaaa catatagtat gggcaagcag ggagctagaa cgattcgcag    6540
ttaatcctgg cctgttagaa acatcagaag gctgtagaca aatactggga cagctacaac    6600
catcccttca gacaggatca gaagaactta gatcattata taatacagta gcaaccctct    6660
attgtgtgca tcaaaggata gagataaaag acaccaagga agctttagac aagatagagg    6720
aagagcaaaa caaaagtaag accaccgcac agcaagcggc cgctgatctt cagacctgga    6780
ggaggagata tgagggacaa ttggagaagt gaattatata aatataaagt agtaaaaatt    6840
gaaccattag gagtagcacc caccaaggca aagagaagag tggtgcagag agaaaaaaga    6900
gcagtgggaa taggagcttt gttccttggg ttcttgggag cagcaggaag cactatgggc    6960
gcagcgtcaa tgacgctgac ggtacaggcc agacaattat tgtctggtat agtgcagcag    7020
cagaacaatt tgctgagggc tattgaggcg caacagcatc tgttgcaact cacagtctgg    7080
ggcatcaagc agctccaggc aagaatcctg gctgtggaaa gatacctaaa ggatcaacag    7140
ctcctgggga tttggggttg ctctggaaaa ctcatttgca ccactgctgt gccttggaat    7200
gctagttgga gtaataaatc tctgaacag atttggaatc acacgacctg gatggagtgg    7260
gacagagaaa ttaacaatta cacaagctta atacactcct taattgaaga atcgcaaaac    7320
```

| | |
|---|---:|
| cagcaagaaa agaatgaaca agaattattg gaattagata aatgggcaag tttgtggaat | 7380 |
| tggtttaaca taacaaattg gctgtggtat ataaaattat tcataatgat agtaggaggc | 7440 |
| ttggtaggtt taagaatagt ttttgctgta ctttctatag tgaatagagt taggcaggga | 7500 |
| tattcaccat tatcgtttca gacccacctc ccaaccccga ggggacccga caggcccgaa | 7560 |
| ggaatagaag aagaaggtgg agagagagac agagacagat ccattcgatt agtgaacgga | 7620 |
| tctcgacggt atcgatcacg agactagcct cgacacaaat ggcagtattc atccacaatt | 7680 |
| ttaaaagaaa agggggatt gggggtaca gtgcaggga aagaatagta gacataatag | 7740 |
| caacagacat acaaactaaa gaattacaaa aacaaattac aaaaattcaa aattttcggg | 7800 |
| tttattacag ggacagcaga aatccacttt ggctcgagaa gcttgatat | 7849 |

<210> SEQ ID NO 133
<211> LENGTH: 9111
<212> TYPE: DNA
<213> ORGANISM: Artificial Sequence
<220> FEATURE:
<223> OTHER INFORMATION: Synthesizd

<400> SEQUENCE: 133

| | |
|---|---:|
| atatcaagct tctcgagcca aagtggattt gctagcgaat tcatcgaggt cgacggtatc | 60 |
| gataagcttg atatcgaatt aggaggaaaa actgtttcat acagaaggcg tcaattagga | 120 |
| ggaaaaactg tttcatacag aaggcgtcaa ttaggaggaa aaactgtttc atacagaagg | 180 |
| cgtcaattgg tcccatcgaa ttaggaggaa aaactgtttc atacagaagg cgtcaattag | 240 |
| gaggaaaaac tgtttcatac agaaggcgtc aattaggagg aaaaactgtt tcatacagaa | 300 |
| ggcgtcaatt ggtcccggga cattttgaca cccccataat attttttccag aattaacagt | 360 |
| ataaattgca tctcttgttc aagagttccc tatcactctc tttaatcact actcacagta | 420 |
| acctcaactc ctggccacca tgacagtgct ggcgccagcc tggagcccaa caacctatct | 480 |
| cctcctgctg ctgctgctga gctcgggact cagtgggacc caggactgct ccttccaaca | 540 |
| cagccccatc tcctccgact tcgctgtcaa aatccgtgag ctgtctgact acctgcttca | 600 |
| agattaccca gtcaccgtgg cctccaacct gcaggacgag gagctctgcg ggggcctctg | 660 |
| gcggctggtc ctggcacagc gctggatgga gcggctcaag actgtcgctg gtccaagat | 720 |
| gcaaggcttg ctggagcgcg tgaacacgga gatacacttt gtcaccaaat gtgccttca | 780 |
| gccccccccc agctgtcttc gcttcgtcca gaccaacatc tcccgcctcc tgcaggagac | 840 |
| ctccgagcag ctggtggcgc tgaagccctg gatcactcgc cagaacttct cccggtgcct | 900 |
| ggagctgcag tgtcagcccg tagagacggt gtttcaccgt gtcagccagg atggtctcga | 960 |
| tctcctgacc tcgtgaagac cacctccct gcgagctaag ctggacagcc aatgacgggt | 1020 |
| aagagagtga cattttcac taacctaaga caggagggcc gtcagagcta ctgcctaatc | 1080 |
| caaagacggg taaagtgat aaaaatgtat cactccaacc taagacaggc gcagcttccg | 1140 |
| agggatttga gatccagaca tgataagata cattgatgag tttggacaaa ccaaaactag | 1200 |
| aatgcagtga aaaaatgcc ttatttgtga aatttgtgat gctattgcct tatttgtaac | 1260 |
| cattataagc tgcaataaac aagttaagtc gataaactgg atctctgctg tccctgtaat | 1320 |
| aaacccgaaa attttgaatt tttgtaattt gttttttgtaa ttctttagtt tgtatgtctg | 1380 |
| ttgctattat gtctactatt cttccccctg cactgtaccc cccaatcccc ccttttcttt | 1440 |
| taaaattgtg gatgaatact gccatttgtg tcgaggctag tctcgtgatc gataccgtcg | 1500 |
| agatccgttc actaatcgaa tggatctgtc tctgtctctc tctccacctt cttcttctat | 1560 |

```
tccttcgggc ctgtcgggtc ccctcggggt tgggaggtgg gtctgaaacg ataatggtga    1620
atatccctgc ctaactctat tcactataga aagtacagca aaaactattc ttaaacctac    1680
caagcctcct actatcatta tgaataattt tatataccac agccaatttg ttatgttaaa    1740
ccaattccac aaacttgccc atttatctaa ttccaataat tcttgttcat tcttttcttg    1800
ctggttttgc gattcttcaa ttaaggagtg tattaagctt gtgtaattgt taatttctct    1860
gtcccactcc atccaggtcg tgtgattcca aatctgttcc agagatttat tactccaact    1920
agcattccaa ggcacagcag tggtgcaaat gagttttcca gagcaacccc aaatccccag    1980
gagctgttga tcctttaggt atcttttccac agccaggatt cttgcctgga gctgcttgat    2040
gccccagact gtgagttgca acagatgctg ttgcgcctca atagccctca gcaaattgtt    2100
ctgctgctgc actataccag acaataattg tctggcctgt accgtcagcg tcattgacgc    2160
tgcgcccata gtgcttcctg ctgctcccaa gaacccaagg aacaaagctc ctattcccac    2220
tgctcttttt tctctctgca ccactcttct ctttgcttg gtgggtgcta ctcctaatgg    2280
ttcaattttt actactttat atttatataa ttcacttctc caattgtccc tcatatctcc    2340
tcctccaggt ctgaagatca gcggccgctt gctgtgcggt ggtcttactt ttgttttgct    2400
cttcctctat cttgtctaaa gcttccttgg tgtcttttat ctctatcctt tgatgcacac    2460
aatagagggt tgctactgta ttatataatg atctaagttc ttctgatcct gtctgaaggg    2520
atggttgtag ctgtcccagt atttgtctac agccttctga tgtttctaac aggccaggat    2580
taactgcgaa tcgttctagc tccctgcttg cccatactat atgttttaat ttatattttt    2640
tctttccccc tggccttaac cgaattttttt cccatcgcga tctaattctc ccccgcttaa    2700
tactgacgct ctcgcaccca tctctctcct tctagcctcc gctagtcaaa atttttggcg    2760
tactcaccag tcgccgcccc tcgcctcttg ccgtgcgcgc ttcagcaagc cgagtcctgc    2820
gtcgagagag ctcctctggt ttcccttttcg ctttcaagtc cctgttcggg cgccactgct    2880
agagattttc cacactgact aaaagggtct gagggatctc tagttaccag agtcacacaa    2940
cagacgggca cacactactt gaagcactca aggcaagctt tattgaggct taagcagtgg    3000
gttccctagt tagccagaga gctcccaggc tcagatctgg tctaaccaga gagacccgtt    3060
tatgtatcga gctaggcact taaatacaat atctctgcaa tgcggcaatt cagtggttcg    3120
tccaatccat gtcagacccg tctgttgcct tcctaataag gcacgatcgt accaccttac    3180
ttccaccaat cggcatgcac ggtgcttttt ctctccttgt aaggcatgtt gctaactcat    3240
cgttaccatg ttgcaagact acaagagtat tgcataagac tacattaagc ttgcagctcc    3300
agcttttgtt cccttagtg agggttaatt gcgcgcttgg cgtaatcatg gtcatagctg    3360
tttcctgtgt gaaattgtta tccgctcaca attccacaca acatcgagc cggaagcata    3420 aagtgtaaag cctggggtgc ctaatgagtg agctaactca cattaattgc gttgcgctca    3480
ctgcccgctt tccagtcggg aaacctgtcg tgccagctgc attaatgaat cggccaacgc    3540
gcggggagag gcggtttgcg tattgggcgc tcttccgctt cctcgctcac tgactcgctg    3600
cgctcggtcg ttcggctgcg gcgagcggta tcagctcact caaaggcggt aatacggtta    3660
tccacagaat caggggataa cgcaggaaag aacatgtgag caaaaggcca gcaaaaggcc    3720
aggaaccgta aaaaggccgc gttgctggcg ttttttccata ggctccgccc cctgacgag    3780 catcacaaaa atcgacgctc aagtcagagg tggcgaaacc cgacaggact ataaagatac    3840
caggcgtttc ccctggaag ctccctcgtg cgctctcctg ttccgaccct gccgcttacc    3900
```

```
ggatacctgt ccgcctttct cccttcggga agcgtggcgc tttctcatag ctcacgctgt    3960
aggtatctca gttcggtgta ggtcgttcgc tccaagctgg gctgtgtgca cgaaccccc     4020 gttcagcccg accgctgcgc cttatccggt aactatcgtc ttgagtccaa cccggtaaga    4080
cacgacttat cgccactggc agcagccact ggtaacagga ttagcagagc gaggtatgta    4140
ggcggtgcta cagagttctt gaagtggtgg cctaactacg gctacactag aagaacagta    4200
tttggtatct gcgctctgct gaagccagtt accttcggaa aaagagttgg tagctcttga    4260
tccggcaaac aaaccaccgc tggtagcggt ggtttttttg tttgcaagca gcagattacg    4320
cgcagaaaaa aaggatctca agaagatcct ttgatctttt ctacgggtc tgacgctcag    4380 tggaacgaaa actcacgtta agggattttg gtcatgagat tatcaaaaag gatcttcacc    4440
tagatccttt taaattaaaa atgaagtttt aaatcaatct aaagtatata tgagtaaact    4500
tggtctgaca gttagaaaaa ctcatcgagc atcaaatgaa actgcaattt attcatatca    4560
ggattatcaa taccatattt ttgaaaaagc cgtttctgta atgaaggaga aaactcaccg    4620
aggcagttcc ataggatggc aagatcctgg tatcggtctg cgattccgac tcgtccaaca    4680
tcaatacaac ctattaattt cccctcgtca aaaataaggt tatcaagtga gaaatcacca    4740
tgagtgacga ctgaatccgg tgagaatggc aaaagtttat gcatttcttt ccagacttgt    4800
tcaacaggcc agccattacg ctcgtcatca aaatcactcg catcaaccaa accgttattc    4860
attcgtgatt gcgcctgagc cagacgaaat acgcgatcgc tgttaaaagg acaattacaa    4920
acaggaatcg aatgcaaccg gcgcaggaac actgccagcg catcaacaat attttcacct    4980
gaatcaggat attcttctaa tacctggaat gctgttttcc cggggatcgc agtggtgagt    5040
aaccatgcat catcaggagt acggataaaa tgcttgatgg tcggaagagg cataaattcc    5100
gtcagccagt ttagtctgac catctcatct gtaacatcat tggcaacgct acctttgcca    5160
tgtttcagaa acaactctgg cgcatcgggc ttcccataca atcgatagat tgtcgcacct    5220
gattgcccga cattatcgcg agcccattta tacccatata aatcagcatc catgttggaa    5280
tttaatcgcg gcctagagca agacgtttcc cgttgaatat ggctcataac accccttgta    5340
ttactgttta tgtaagcaga cagttttatt gttcatgacc aaaatccctt aacgtgagtt    5400
ttcgttccac tgagcgtcag accccgtaga aaagatcaaa ggatcttcaa attgtaagcg    5460
ttaatatttt gttaaaattc gcgttaaatt tttgttaaat cagctcattt tttaaccaat    5520
aggccgaaat cggcaaaatc ccttataaat caaaagaata gaccgagata gggttgagtg    5580
ttgttccagt ttggaacaag agtccactat taaagaacgt ggactccaac gtcaaagggc    5640
gaaaaaccgt ctatcagggc gatggcccac tacgtgaacc atcaccctaa tcaagttttt    5700
tggggtcgag gtgccgtaaa gcactaaatc ggaaccctaa agggagcccc cgatttagag    5760
cttgacgggg aaagccggcg aacgtggcga gaaaggaagg gaagaaagcg aaaggagcgg    5820
gcgctagggc gctggcaagt gtagcggtca cgctgcgcgt aaccaccaca cccgccgcgc    5880
ttaatgcgcc gctacagggc gcgtcccatt cgccattcag gctgcgcaac tgttgggaag    5940 ggcgatcgt gcgggcctct tcgctattac gccagctggc gaaaggggga tgtgctgcaa    6000
ggcgattaag ttgggtaacg ccagggtttt cccagtcacg acgttgtaaa acgacggcca    6060
gtgagcgcgc gtaatacgac tcactatagg gcgaattggg tacgtcccta ggcctccaaa    6120
aaagcctcct cactacttct ggaatagctc agaggccgag gcggcctcgg cctctgcata    6180
aataaaaaaa attagtcagc catggggcgg agaatgggcg gaactgggcg gagttagggg    6240
cgggatgggc ggagttaggg gcgggatagc tagagccaga catgataaga tacattgatg    6300
```

```
agtttggaca aaccacaact agaatgcagt gaaaaaaatg ctttatttgt gaaatttgtg    6360
atgctattgc tttatttgta accattataa gctgcaataa acaagttcct ctcactctct    6420
gatattcatt tctttgcaag ttataaatac tgaataataa gatgacatga actactactg    6480
ctagagattt tccacactga ctaaaagggt ctgagggatc tctagttacc agagtcacac    6540
aacagacggg cacacactac ttgaagcact caaggcaagc tttattgagg cttaagcagt    6600
gggttcccta gttagccaga gagctcccag gctcagatct ggtctaacca gagagaccca    6660
gtacaagcaa aaagcagatc ttgtcttcgt tgggagtgaa ttagcccttc cagtcccccc    6720
ttttctttta aaaagtggct aagatctaca gctgccttgt aagtcattgg tcttaaaggt    6780
accgagctcg aattccgcgg caggcgggga ggcggcccaa agggagatcc gactcgtctg    6840
agggcgaagg cgaagacgcg gaagaggccg cagagccggc agcaggccgc gggaaggaag    6900
gtccgctgga ttgagggccg aagggacgta gcagaaggac gtcccgcgca gaatccaggt    6960
ggcaacacag gcgagcagcc aaggaaagga cgatgatttc cccgacaaca ccacggaatt    7020
gtcagtgccc aacagccgag cccctgtcca gcagcgggca aggcaggcgg cgatgagttc    7080
cgccgtggca atagggaggg ggaaagcgaa agtcccggaa aggagctgac aggtggtggc    7140
aatgccccaa ccagtggggg ttgcgtcagc aaacacagtg cacaccacgc cacgttgcct    7200
gacaacgggc cacaactcct cataaagaga cagcaaccag gatttataca aggaggagaa    7260
aatgaaagcc atacgggaag caatagcatg atacaaaggc attaaagcag cgtatccaca    7320
tagcgtaaaa ggagcaacat agttaagaat accagtcaat cttttcacaaa ttttgtaatc    7380 cagaggttga ttactagttc tagagtcgac ttagcgaggg ggcagggcct gcatgtgaag    7440
ggcgtcgtag gtgtccttgg tggctgtact gagaccctgg taaaggccat cgtgccccctt   7500 gcccctccgg cgctcgcctt tcatcccaat ctcactgtag gcctccgcca tcttatcttt    7560
ctgcagttca ttgtacaggc cttcctgagg gttcttcctt tcggcttttc ccccatctc    7620 agggtcccgg ccacgcctct tgtccaaaac atcgtactcc tctcttcgtc ctagattgag    7680
ctcgttatag agctggttct ggccctgctg gtacgcgggg gcgtctgcgc tcctgctgaa    7740
cttcactctg gagcgatagg ctgcgaagtc gcgtggtggg gcatagggct ggtaatgctt    7800
gcgggtgggc ccggggcggc ggggagtcat gttcatgtag tcactgtgca ggagcctgct    7860
cctcttactc ctcacccaga aaataataaa ggccactgtt actagcaagc tatagcaagc    7920
caggactcca ccaaccacca ccagcaccca aagggcttaa gaaggtccgg gaaatagggg    7980
acttggacaa aggtgtttcc cttttcacatg gataatggtt ccattgctct tctcattgtc    8040
taggtaagga ggaggataca taacttcaat tgcggccgct gaggacacgg tgaccagggt    8100
tccttggccc cagtagtcca tagcgtagct gccgccgtag tagtagtgct tcgcacagta    8160
atacacagcc gtgtcctcgg ctctcaggct gttcatttgc agatacagtg agttcttggc    8220
attgtctctg gagatggtga atcgggactt cagggcgctg ttgtagtagg ttgtctcgct    8280
gccccagatc actgaaaccc actccagccc cttccctgga gcctggcgga cccaggacac    8340
gccataatca ggcagggaca ctccagaggc tgcacaggag agtctcaggg acccccagg    8400 ctgtaccaag cctcccccag actccaccag ctgcacctca gatccgccgc cacccgaccc    8460
accaccgccc gagccaccgc caccttttgat ctccactttg gtgccctgac cgaacgtgta    8520
cggaagcgta ttaccctgtt ggcaatagta ggtggcgaag tcctccggct gcaagctcga    8580
gatggtcagg gtaaaatcgg tgcccgaacc cgagccgcta aaacgcgacg gcacgcctga    8640
```

| | |
|---|---|
| gtgtaatctt gatgtatgat aaattaacag tttcggcgct ttacccggtt tctgctgata | 8700 |
| ccaatttaaa tatttactaa tgtcctgact tgccctgcag gtaatggtca cgcgatcacc | 8760 |
| cacgctcgcg ctcaggctgc tcgggctctg gtcatctgg atatccggcc tggcggcgtg | 8820 |
| gagcagcaag gccagcggca ggagcaaggc ggtcactgg aaggccatgg tggcggatcc | 8880 |
| tgtgttctgg cggcaaaccc gttgcgaaaa agaacgttca cggcgactac tgcacttata | 8940 |
| tacggttctc ccccaccctc gggaaaaagg cggagccagt acacgacatc actttcccag | 9000 |
| tttaccccgc gccaccttct ctaggcaccg gttcaattgc cgacccctcc ccccaacttc | 9060 |
| tcggggactg tgggcgatgt gcgctctgcc cactgacggg caccggagcc g | 9111 |

<210> SEQ ID NO 134
<211> LENGTH: 8449
<212> TYPE: DNA
<213> ORGANISM: Artificial Sequence
<220> FEATURE:
<223> OTHER INFORMATION: Synthesizd

<400> SEQUENCE: 134

| | |
|---|---|
| cggctccggt gcccgtcagt gggcagagcg cacatcgccc acagtccccg agaagttggg | 60 |
| gggagggggtc ggcaattgaa ccggtgccta gagaaggtgg cgcggggtaa actgggaaag | 120 |
| tgatgtcgtg tactggctcc gccttttttcc cgagggtggg ggagaaccgt atataagtgc | 180 |
| agtagtcgcc gtgaacgttc ttttttcgcaa cgggtttgcc gccagaacac aggatccgcc | 240 |
| accatggcct taccagtgac cgccttgctc ctgccgctgg ccttgctgct ccacgccgcc | 300 |
| aggccggata tccagatgac ccagagcccg agcagcctga gcgcgagcgt gggtgatcgc | 360 |
| gtgaccatta cctgcagggc aagtcaggac attagtaaat atttaaattg gtatcagcag | 420 |
| aaaccgggta aagcgccgaa actgttaatt tatcatacat caagattaca ctcaggcgtg | 480 |
| ccgtcgcgtt ttagcggctc gggttcgggc accgatttta ccctgaccat ctcgagcttg | 540 |
| cagccggagg acttcgccac ctactattgc caacaggta atacgcttcc gtacacgttc | 600 |
| ggtcagggca ccaaagtgga gatcaaaggt ggcggtggct cgggcggtgg tgggtcgggt | 660 |
| ggcggcggat ctgaggtgca gctggtgag tctggggga gcttggtaca gcctgggggg | 720 |
| tccctgagac tctcctgtgc agcctctgga gtgtccctgc ctgattatgg cgtgtcctgg | 780 |
| gtccgccagg ctccagggaa ggggctgag tgggtttcag tgatctgggg cagcgagaca | 840 |
| acctactaca cagcgccct gaagtcccga ttcaccatct ccagagacaa tgccaagaac | 900 |
| tcactgtatc tgcaaatgaa cagcctgaga gccgaggaca cggctgtgta ttactgtgcg | 960 |
| aagcactact actacggcgg cagctacgct atggactact ggggccaagg aaccctggtc | 1020 |
| accgtgtcct caaccacgac gccagcgccg cgaccaccaa caccggcgcc caccatcgcg | 1080 |
| tcgcagcccc tgtccctgcg cccagaggcg tgccggccag cggcgggggg cgcagtgcac | 1140 |
| acgagggggc tggacttcgc ctgtgatatc tacatctggg cgcccttggc cgggacttgt | 1200 |
| ggggtccttc tcctgtcact ggttatcacc ctttactgca acggggcag aaagaaactc | 1260 |
| ctgtatatat tcaaacaacc atttatgaga ccagtacaaa ctactcaaga ggaagatggc | 1320 |
| tgtagctgcc gatttccaga agaagaagaa ggaggatgtg aactgagagt gaagttcagc | 1380 |
| aggagcgcag acgccccgc gtaccagcag gccagaacc agctctataa cgagctcaat | 1440 |
| ctaggacgaa gagaggagta cgatgttttg gacaagaggc gtggccggga ccctgagatg | 1500 |
| gggggaaagc cgaagggaa gaaccctcag gaaggcctgt acaatgaact gcagaaagat | 1560 |
| aagatggcgg aggcctacag tgagattggg atgaaaggcg agcgccggag gggcaagggg | 1620 |

```
cacgatggcc tttaccaggg tctcagtaca gccaccaagg acacctacga cgcccttcac   1680
atgcaggccc tgcccctcg cggttccgga gccacgaact tctctctgtt aaagcaagca    1740
ggagacgtgg aagaaaaccc cggtcctatg acagtgctgg cgccagcctg agcccaaca    1800 acctatctcc tcctgctgct gctgctgagc tcgggactca gtgggaccca ggactgctcc   1860
ttccaacaca gccccatctc ctccgacttc gctgtcaaaa tccgtgagct gtctgactac   1920
ctgcttcaag attcccagt caccgtggcc tccaacctgc aggacgagga gctctgcggg    1980
ggcctctggc ggctggtcct ggcacagcgc tggatggagc ggctcaagac tgtcgctggg   2040
tccaagatgc aaggcttgct ggagcgcgtg aacacgagga tacactttgt caccaaatgt   2100
gcctttcagc ccccccccag ctgtcttcgc ttcgtccaga ccaacatctc ccgcctcctg   2160
caggagacct ccgagcagct ggtggcgctg aagccctgga tcactcgcca gaacttctcc   2220
cggtgcctgg agctgcagtg tcagcccgta gagacggtgt tcaccgtgt cagccaggat   2280 ggtctcgatc tcctgacctc gtgagtcgac tctagaacta gtaatcaacc tctggattac   2340
aaaatttgtg aaagattgac tggtattctt aactatgttg ctcctttac gctatgtgga    2400 tacgctgctt taatgccttt gtatcatgct attgcttccc gtatggcttt cattttctcc   2460
tccttgtata atcctggtt gctgtctctt tatgaggagt tgtggcccgt tgtcaggcaa    2520
cgtggcgtgg tgtgcactgt gtttgctgac gcaaccccca ctggttgggg cattgccacc   2580
acctgtcagc tcctttccgg gactttcgct ttccccctcc ctattgccac ggcggaactc   2640
atcgccgcct gccttgcccg ctgctggaca ggggctcggc tgttgggcac tgacaattcc   2700
gtggtgttgt cggggaaatc atcgtccttt ccttggctgc tcgcctgtgt tgccacctgg   2760
attctgcgcg ggacgtcctt ctgctacgtc ccttcggccc tcaatccagc ggaccttcct   2820
tcccgcggcc tgctgccggc tctgcggcct cttccgcgtc ttcgccttcg ccctcagacg   2880
agtcggatct ccctttgggc cgcctccccg cctgccgcgg aattcgagct cggtacctt    2940 aagaccaatg acttacaagg cagctgtaga tcttagccac ttttttaaaag aaagggggg   3000 actggaaggg ctaattcact cccaacgaag acaagatctg cttttttgctt gtactgggtc   3060 tctctggtta gaccagatct gagcctggga gctctctggc taactaggga acccactgct   3120
taagcctcaa taaagcttgc cttgagtgct tcaagtagtg tgtgcccgtc tgttgtgtga   3180
ctctggtaac tagagatccc tcagacccctt tagtcagtg tggaaaatct ctagcagtag   3240
tagttcatgt catcttatta ttcagtattt ataacttgca aagaaatgaa tatcagagag   3300
tgagaggaac ttgtttattg cagcttataa tggttacaaa taaagcaata gcatcacaaa   3360
tttcacaaat aaagcatttt tttcactgca ttctagttgt ggtttgtcca aactcatcaa   3420
tgtatcttat catgtctggc tctagctatc ccgcccctaa ctccgcccat cccgccccta   3480
actccgccca gttccgccca ttctccgccc catggctgac taatttttt tatttatgca   3540 gaggccgagg ccgcctcggc ctctgagcta ttccagaagt agtgaggagg cttttttgga   3600
ggcctaggga cgtacccaat tcgccctata gtgagtcgta ttacgcgcgc tcactggccg   3660
tcgttttaca acgtcgtgac tgggaaaacc ctggcgttac ccaacttaat cgccttgcag   3720
cacatccccc tttcgccagc tggcgtaata gcgaagaggc ccgcaccgat cgcccttccc   3780
aacagttgcg cagcctgaat ggcgaatggg acgcgccctg tagcggcgca ttaagcgcgg   3840
cgggtgtggt ggttacgcgc agcgtgaccg ctacacttgc cagcgcccta gcgcccgctc   3900
ctttcgcttt cttcccttcc tttctcgcca cgttcgccgg ctttccccgt caagctctaa   3960
```

```
atcgggggct cccctttaggg ttccgattta gtgctttacg gcacctcgac cccaaaaaac    4020
ttgattaggg tgatggttca cgtagtgggc catcgccctg atagacggtt tttcgccctt    4080
tgacgttgga gtccacgttc tttaatagtg gactcttgtt ccaaactgga acaacactca    4140
accctatctc ggtctattct tttgatttat aagggatttt gccgatttcg gcctattggt    4200
taaaaatga gctgatttaa caaaaattta acgcgaattt taacaaaata ttaacgctta    4260
caatttaggt ggcacttttc ggggaaatgt gcgcggaacc cctatttgtt tatttttcta    4320
aatacattca aatatgtatc cgctcatgag acaataaccc tgataaatgc ttcaataata    4380
ttgaaaaagg aagagtatga gccatattca acgggaaacg tcttgctcta ggccgcgatt    4440
aaattccaac atggatgctg atttatatgg gtataaatgg gctcgcgata atgtcgggca    4500
atcaggtgcg acaatctatc gattgtatgg gaagcccgat gcgccagagt tgtttctgaa    4560
acatggcaaa ggtagcgttg ccaatgatgt tacagatgag atggtcagac taaactggct    4620
gacgaatttt atgcctcttc cgaccatcaa gcattttatc cgtactcctg atgatgcatg    4680
gttactcacc actgcgatcc ccgggaaaac agcattccag gtattagaag aatatcctga    4740
ttcaggtgaa aatattgttg atgcgctggc agtgttcctg cgccggttgc attcgattcc    4800
tgtttgtaat tgtcctttta acagcgatcg cgtatttcgt ctggctcagg cgcaatcacg    4860
aatgaataac ggtttggttg atgcgagtga ttttgatgac gagcgtaatg gctggcctgt    4920
tgaacaagtc tggaaagaaa tgcataaact tttgccattc tcaccggatt cagtcgtcac    4980
tcatggtgat ttctcacttg ataaccttat ttttgacgag gggaaattaa taggttgtat    5040
tgatgttgga cgagtcggaa tcgcagaccg ataccaggat cttgccatcc tatggaactg    5100
cctcggtgag ttttctcctt cattacagaa acggcttttt caaaaatatg gtattgataa    5160
tcctgatatg aataaattgc agtttcattt gatgctcgat gagttttttct aactgtcaga    5220
ccaagtttac tcatatatac tttagattga tttaaaactt catttttaat ttaaaaggat    5280
ctaggtgaag atccttttg ataatctcat gaccaaaatc ccttaacgtg agttttcgtt    5340
ccactgagcg tcagaccccg tagaaaagat caaaggatct tcttgagatc ctttttttct    5400
gcgcgtaatc tgctgcttgc aaacaaaaaa accaccgcta ccagcggtgg tttgtttgcc    5460
ggatcaagag ctaccaactc tttttccgaa ggtaactggc ttcagcagag cgcagatacc    5520
aaatactgtt cttctagtgt agccgtagtt aggccaccac ttcaagaact ctgtagcacc    5580
gcctacatac ctcgctctgc taatcctgtt accagtggct gctgccagtg gcgataagtc    5640
gtgtcttacc gggttggact caagacgata gttaccggat aaggcgcagc ggtcgggctg    5700
aacggggggt tcgtgcacac agcccagctt ggagcgaacg acctacaccg aactgagata    5760
cctacagcgt gagctatgag aaagcgccac gcttcccgaa gggagaaagg cggacaggta    5820
tccggtaagc ggcagggtcg gaacaggaga gcgcacgagg gagcttccag ggggaaacgc    5880
ctggtatctt tatagtcctg tcgggtttcg ccacctctga cttgagcgtc gatttttgtg    5940
atgctcgtca ggggggcgga gcctatggaa aaacgccagc aacgcggcct ttttacggtt    6000
cctggccttt tgctggcctt tgctcacat gttctttcct gcgttatccc ctgattctgt    6060
ggataaccgt attaccgcct ttgagtgagc tgataccgct cgccgcagcc gaacgaccga    6120
gcgcagcgag tcagtgagcg aggaagcgga agagcgccca atacgcaaac cgcctctccc    6180
cgcgcgttgg ccgattcatt aatgcagctg gcacgacagg tttcccgact ggaaagcggg    6240
cagtgagcgc aacgcaatta atgtgagtta gctcactcat taggcacccc aggctttaca    6300
ctttatgctt ccggctcgta tgttgtgtgg aattgtgagc ggataacaat ttcacacagg    6360
```

-continued

```
aaacagctat gaccatgatt acgccaagcg cgcaattaac cctcactaaa gggaacaaaa    6420
gctggagctg caagcttaat gtagtcttat gcaatactct tgtagtcttg caacatggta    6480
acgatgagtt agcaacatgc cttacaagga gagaaaaagc accgtgcatg ccgattggtg    6540
gaagtaaggt ggtacgatcg tgccttatta ggaaggcaac agacgggtct gacatggatt    6600
ggacgaacca ctgaattgcc gcattgcaga gatattgtat ttaagtgcct agctcgatac    6660
ataaacgggt ctctctggtt agaccagatc tgagcctggg agctctctgg ctaactaggg    6720
aacccactgc ttaagcctca ataaagcttg ccttgagtgc ttcaagtagt gtgtgcccgt    6780
ctgttgtgtg actctggtaa ctagagatcc ctcagaccct tttagtcagt gtggaaaatc    6840
tctagcagtg gcgcccgaac agggacttga agcgaaagg gaaaccagag gagctctctc     6900
gacgcaggac tcggcttgct gaagcgcgca cggcaagagg cgaggggcgg cgactggtga    6960
gtacgccaaa aattttgact agcggaggct agaaggagag atgggtgc gagagcgtca      7020 gtattaagcg ggggagaatt agatcgcgat gggaaaaaat tcggttaagg ccaggggga     7080 agaaaaaata taaattaaaa catatagtat gggcaagcag ggagctagaa cgattcgcag    7140
ttaatcctgg cctgttagaa acatcagaag gctgtagaca aatactggga cagctacaac   7200
catcccttca gacaggatca gaagaactta gatcattata taatacagta gcaaccctct   7260
attgtgtgca tcaaggata gagataaaag acaccaagga agctttagac aagatagagg    7320
aagagcaaaa caaaagtaag accaccgcac agcaagcggc cgctgatctt cagacctgga    7380
ggaggagata tgagggacaa ttggagaagt gaattatata aatataaagt agtaaaaatt    7440
gaaccattag gagtagcacc caccaaggca agagaagag tggtgcagag agaaaaaaga    7500
gcagtgggaa taggagcttt gttccttggg ttcttgggag cagcaggaag cactatgggc    7560
gcagcgtcaa tgacgctgac ggtacaggcc agacaattat tgtctggtat agtgcagcag    7620
cagaacaatt tgctgagggc tattgaggcg caacagcatc tgttgcaact cacagtctgg    7680
ggcatcaagc agctccaggc aagaatcctg gctgtggaaa gatacctaaa ggatcaacag    7740
ctcctgggga tttggggttg ctctggaaaa ctcatttgca ccactgctgt gccttggaat    7800
gctagttgga gtaataaatc tctggaacag atttggaatc acacgacctg gatggagtgg    7860
gacagagaaa ttaacaatta cacaagctta atacactcct taattgaaga atcgcaaaac    7920
cagcaagaaa agaatgaaca agaattattg gaattagata atgggcaag tttgtggaat     7980 tggtttaaca taacaaattg gctgtggtat ataaaattat tcataatgat agtaggaggc    8040
ttggtaggtt taagaatagt ttttgctgta ctttctatag tgaatagagt taggcaggga    8100
tattcaccat tatcgtttca gacccacctc ccaaccccga ggggacccga caggcccgaa    8160
ggaatagaag aagaaggtgg agagagagac agagacagat ccattcgatt agtgaacgga    8220
tctcgacggt atcgatcacg agactagcct cgacacaaat ggcagtattc atccacaatt    8280
ttaaaagaaa aggggggatt ggggggtaca gtgcaggga aagaatagta gacataatag      8340
caacagacat acaaactaaa gaattacaaa aacaaattac aaaaattcaa aattttcggg    8400
tttattacag ggacagcaga atccactttt ggctcgagaa gcttgatat                 8449
```

ACTIVATION OF APC IN IMMUNOTHERAPY

CROSS REFERENCE TO RELATED PATENT APPLICATIONS

This application claims the benefit of U.S. Provisional Application 62/840,985, filed Apr. 30, 2019, U.S. Provisional Application 62/878,067, Jul. 24, 2019, and U.S. Provisional Application 62/880,298, filed Jul. 30, 2019, which are hereby incorporated by reference in their entirety.

SEQUENCE LISTING INFORMATION

A computer readable text file, entitled "Sequence Listing_ST25.txt," created on or about Apr. 24, 2020, with a file size of about 151 KB, contains the sequence listing for this application and is hereby incorporated by reference in its entirety.

TECHNICAL FIELD

The present disclosure relates to compositions of activating and/or recruiting APC in immunotherapy in the treatment of diseases, including cancer.

BACKGROUND

Adoptive transfer of T cells engineered to express a chimeric antigen receptor (CAR) has been showing outstanding responses for treating blood tumors. Unlike the blood tumor environment of blood malignancies, CAR T cells show little progress in treating solid tumors. For example, recent progress in genome editing technologies allows scientists to disrupt gene expression in T-cells appeared to enhance effector functions or to bypass tumor immune suppression and metabolically hostile tumor microenvironment. Thus, there is a need to modulate T cell to address problems associated with solid tumors.

SUMMARY

Conventional CAR-T therapy is not effective in the treatment of solid tumors. One reason is that there is no significant activation of the inflammatory response in the tumor microenvironment, and insufficient antigen-presenting cells (APCs) are recruited or activated at the tumor site. The clinical trial of FLT3L protein showed some progress for treating tumors, but a one-time dose of injected protein may cause side effects, and the site of injection needs to match the location of the tumor.

Embodiments relate to an isolated nucleic acid comprising a nucleic acid sequence and an additional nucleic acid sequence, the nucleic acid sequence encoding a binding molecule, the additional nucleic acid sequence encoding a therapeutic agent that is or comprises an inflammatory cytokine or a fusion protein associated with the inflammatory cytokine. In embodiments, the binding molecule is a chimeric antigen receptor (CAR) or a modified TCR. Embodiments further relate to a population of CAR cells comprising the nucleic acid sequence and the additional nucleic acid sequence, wherein the CAR cells comprise lymphocytes, leukocytes, PBMCs, NK cells, or dendritic cells. Embodiments relate to a population of CAR cells comprising the nucleic acid sequence and the additional nucleic acid sequence, wherein the CAR cells are T cells, NK cells, or dendritic cells. Embodiments relate to a method to increase proliferative and/or reconstitutive capacities of T cells, the method comprising: providing a T cell, and modulating the expression of one or more genes of T cells. Embodiments further relate to a method to enhance inhibitory capacities of T cells on tumor cells, the method comprising: providing a T cell; and modulating the expression of one or more genes of T cells, which are provided in Table 1. In embodiments, the T cells comprise an antigen recognizing receptor, such as a T cell receptor (TCR) or chimeric antigen receptor (CAR). Embodiments relate to compositions and methods of modulating activities and functions of lymphocytes (e.g., T cells). Embodiments relate to a modified cell comprising an antigen binding molecule, and the disruption of an endogenous gene associated with T cell apoptosis. In embodiments, the gene comprises at least one of CD80, Fas, Bcl-2, Bax, PI3K, AKT, C-jun, C-fos, C-myc, Gata3, Tox, Mt2, and/or Pdcd4.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

DETAILED DESCRIPTION

Figure 1:
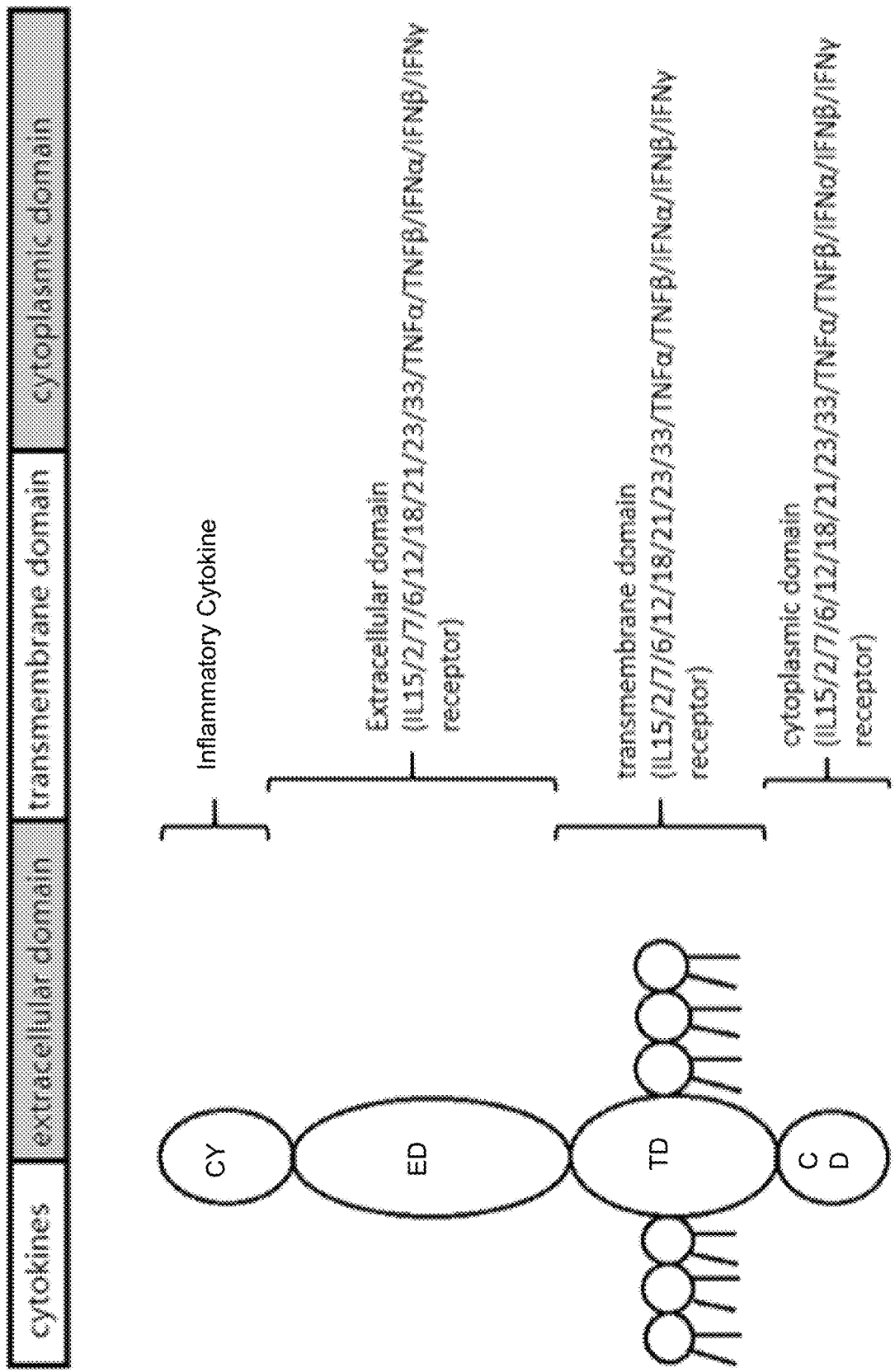
FIG. 1 shows a schematic diagram of an exemplary fusion protein.
Figure 2:
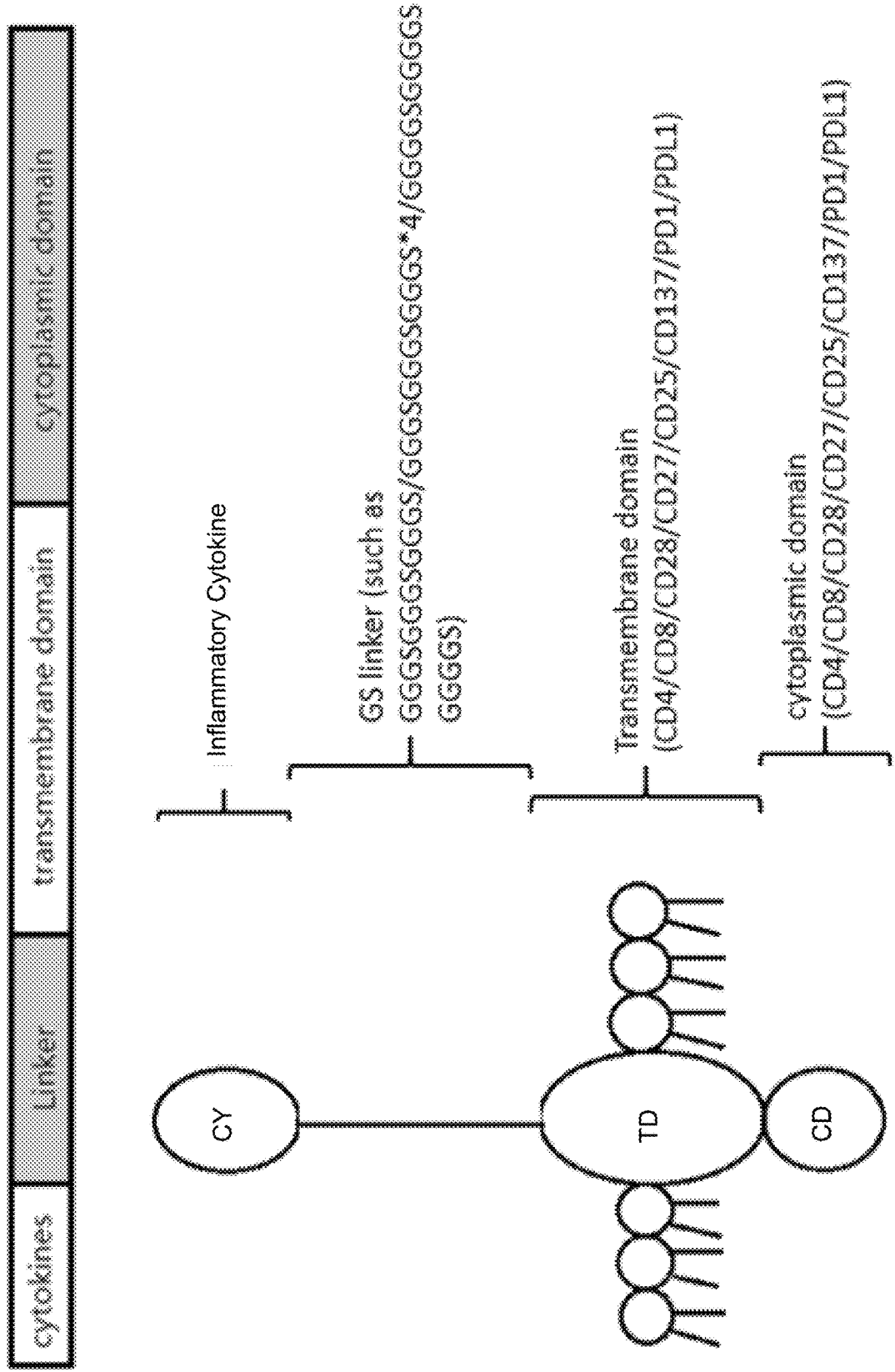
FIG. 2 shows a schematic diagram of another exemplary fusion protein.
Figure 3:
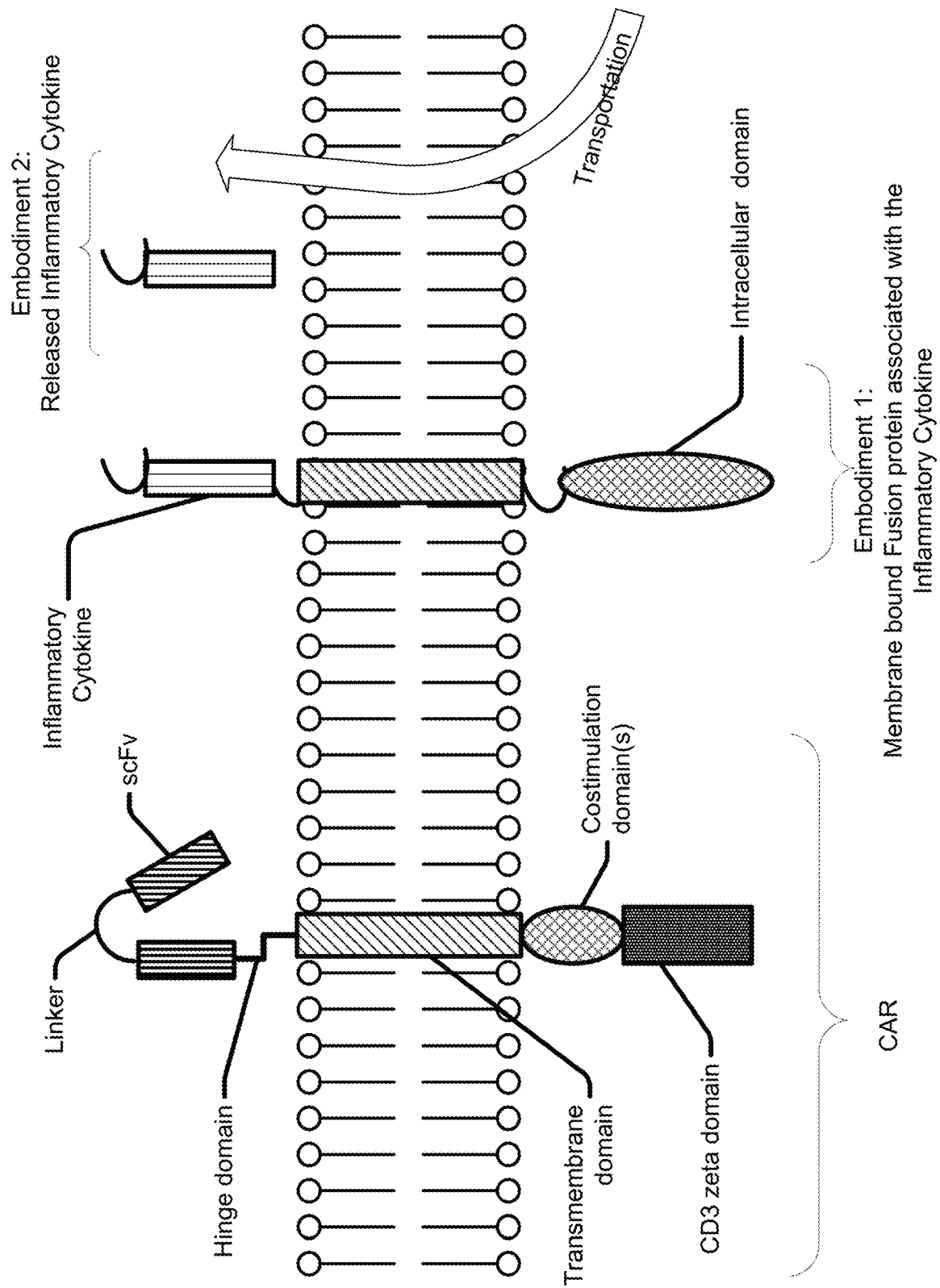
FIG. 3 shows a schematic diagram of an exemplary CAR molecule and a fusion protein.
Figure 4:
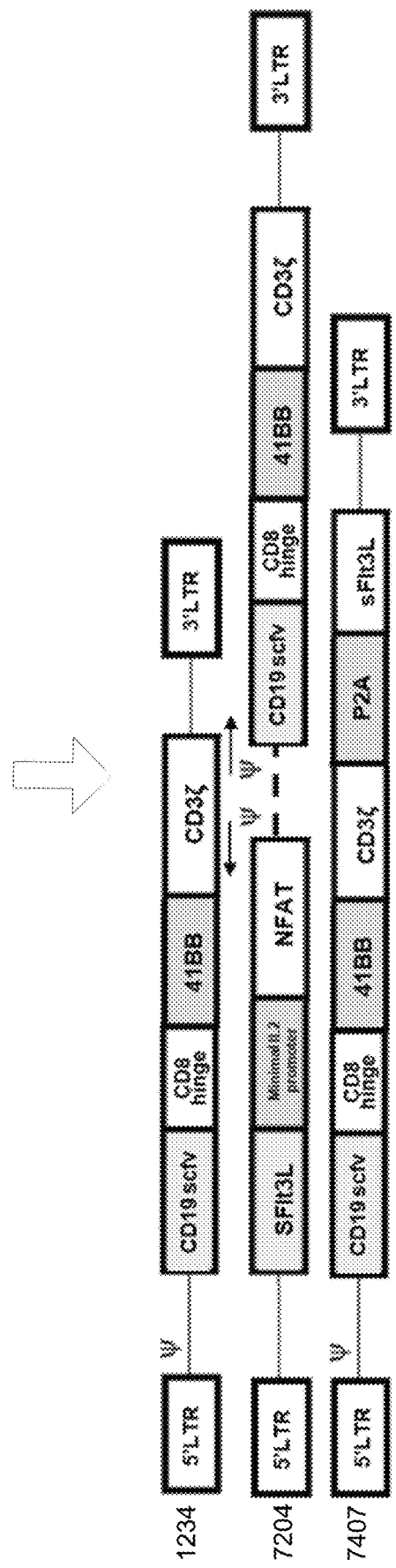
FIG. 4 shows schematic diagrams of various constructs.

Unless defined otherwise, all technical and scientific terms used herein have the same meaning as commonly understood by those of ordinary skill in the art to which the disclosure belongs. Although any method and material similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies; monoclonal antibodies; Fv, Fab, Fab', and F(ab')$_2$ fragments; as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragments" refers to a portion of a full-length antibody, for example, the antigen binding or variable region of the antibody. Other examples of antibody fragments include Fab, Fab', F(ab')$_2$, and Fv fragments; diabodies; linear antibodies; single-chain antibody molecules; and multi-specific antibodies formed from antibody fragments.

The term "Fv" refers to the minimum antibody fragment which contains a complete antigen-recognition and -binding site. This fragment consists of a dimer of one heavy- and one light-chain variable region domain in tight, non-covalent association. From the folding of these two domains emanates six hypervariable loops (3 loops each from the H and L chain) that contribute amino acid residues for antigen binding and confer antigen binding specificity to the antibody. However, even a single variable domain (or half of an Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. κ and λ light chains refer to the two major antibody light chain isotypes.

The term "synthetic antibody" refers to an antibody which is generated using recombinant DNA technology, such as, for example, an antibody expressed by a bacteriophage. The term also includes an antibody which has been generated by the synthesis of a DNA molecule encoding the antibody and the expression of the DNA molecule to obtain the antibody or to obtain an amino acid encoding the antibody. The synthetic DNA is obtained using technology that is available and well known in the art.

The term "antigen" refers to a molecule that provokes an immune response, which may involve either antibody production, or the activation of specific immunologically-competent cells, or both. Antigens include any macromolecule, including all proteins or peptides, or molecules derived from recombinant or genomic DNA. For example, DNA including a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized, or derived from a biological sample including a tissue sample, a tumor sample, a cell, or a biological fluid.

The term "anti-tumor effect" as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumors in the first place.

The term "auto-antigen" refers to an endogenous antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from a subject that is subsequently re-introduced into the same subject.

The term "allogeneic" is used to describe a graft derived from a different subject of the same species. As an example, a donor subject may be related or unrelated to the recipient subject, but the donor subject has immune system markers that are similar to the recipient subject.

The term "xenogeneic" is used to describe a graft derived from a subject of a different species. As an example, the donor subject is from a different species than a recipient subject, and the donor subject and the recipient subject can be genetically and immunologically incompatible.

The term "cancer" is used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes" and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any element listed after the phrase and can include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base-pairing rules, or there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein, or (b) a peptide or polypeptide having an amino acid sequence that is substantially identical to a sequence of amino acids in a reference peptide or protein.

The term "co-stimulatory ligand," refers to a molecule on an antigen presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor, and a ligand that binds explicitly with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T cell proliferation and/or upregulation or downregulation of key molecules.

The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as a template for synthesis of other polymers and macromolecules in biological processes having either a defined sequence of nucleotides (i.e., rRNA, tRNA and mRNA) or a defined sequence of amino acids and the biological properties resulting from there. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression" refers to the transcription and/or translation of a particular nucleotide sequence driven by its promoter.

The term "expression vector" refers to a vector including a recombinant polynucleotide including expression control (regulatory) sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous, then the two sequences are 60% homologous. By way of example, the DNA sequences ATTGCC and TATGGC share 50% homology. A comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

The term "substantially purified" refers to a material that is substantially free from components that are normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. Moreover, the use of lentiviruses enables integration of the genetic information into the host chromosome resulting in stably transduced genetic information. HIV, SIV, and FIV are all examples of lentiviruses. Vectors derived from lentiviruses offer the means to achieve significant levels of gene transfer in vivo.

The term "modulating," refers to mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

The term "under transcriptional control" refers to a promoter being operably linked to and in the correct location and orientation in relation to a polynucleotide to control (regulate) the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having solid tumor or a hematological malignancy characterized by overexpression of the tumor antigen can be determined by standard assays known in the art.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme), astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma, and brain metastases).

A solid tumor antigen is an antigen expressed on a solid tumor. In embodiments, solid tumor antigens are also expressed at low levels on healthy tissue. Examples of solid tumor antigens and their related disease tumors are provided in Table 1.

TABLE 1

| Solid Tumor antigen | Disease tumor |
|---|---|
| PRLR | Breast Cancer |
| CLCA1 | colorectal cancer |

TABLE 1-continued

| Solid Tumor antigen | Disease tumor |
| --- | --- |
| MUC12 | colorectal cancer |
| GUCY2C | colorectal cancer |
| GPR35 | colorectal cancer |
| CR1L | Gastric Cancer |
| MUC 17 | Gastric Cancer |
| TMPRSS11B | esophageal cancer |
| MUC21 | esophageal cancer |
| TMPRSS11E | esophageal cancer |
| CD207 | bladder Cancer |
| SLC30A8 | pancreatic Cancer |
| CFC1 | pancreatic Cancer |
| SLC12A3 | Cervical Cancer |
| SSTR1 | Cervical tumor |
| GPR27 | Ovary tumor |
| FZD10 | Ovary tumor |
| TSHR | Thyroid Tumor |
| SIGLEC15 | Urothelial cancer |
| SLC6A3 | Renal cancer |
| KISS1R | Renal cancer |
| QRFPR | Renal cancer: |
| GPR119 | Pancreatic cancer |
| CLDN6 | Endometrial cancer/Urothelial cancer |
| UPK2 | Urothelial cancer (including bladder cancer) |
| ADAM12 | Breast cancer, pancreatic cancer and the like |
| SLC45A3 | Prostate cancer |
| ACPP | Prostate cancer |
| MUC21 | Esophageal cancer |
| MUC16 | Ovarian cancer |
| MS4A12 | Colorectal cancer |
| ALPP | Endometrial cancer |
| CEA | Colorectal carcinoma |
| EphA2 | Glioma |
| FAP | Mesotelioma |
| GPC3 | Lung squamous cell carcinoma |
| IL13-Rα2 | Glioma |
| Mesothelin | Metastatic cancer |
| PSMA | Prostate cancer |
| ROR1 | Breast lung carcinoma |
| VEGFR-II | Metastatic cancer |
| GD2 | Neuroblastoma |
| FR-α | Ovarian carcinoma |
| ErbB2 | Carcinomasb |
| EpCAM | Carcinomasa |
| EGFRvIII | Glioma-Glioblastoma |
| EGFR | Glioma-NSCL cancer |
| tMUC 1 | Cholangiocarcinoma, Pancreatic cancer, Breast Cancer |
| PSCA | pancreas, stomach, or prostate cancer |

The term "parenteral administration" of a composition includes, e.g., subcutaneous (s.c.), intravenous (i.v.), intramuscular (i.m.), intrasternal injection, or infusion techniques.

The terms "patient," "subject," and "individual," and the like are used interchangeably herein and refer to any human, or animal, amenable to the methods described herein. In certain non-limiting embodiments, the patient, subject, or individual is a human or animal. In embodiments, the term "subject" is intended to include living organisms in which an immune response can be elicited (e.g., mammals). Examples of subjects include humans, and animals, such as dogs, cats, mice, rats, and transgenic species thereof.

A subject in need of treatment or in need thereof includes a subject having a disease, condition, or disorder that needs to be treated. A subject in need thereof also includes a subject that needs treatment for prevention of a disease, condition, or disorder.

The term "polynucleotide" or "nucleic acid" refers to mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes all forms of nucleic acids including single and double-stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In embodiments, a polypeptide variant is distinguished from a reference polypeptide by one or more substitutions, which may be conservative or non-conservative. In embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted or replaced with different amino acid residues.

The term "promoter" refers to a DNA sequence recognized by the synthetic machinery of the cell or introduced synthetic machinery, required to initiate the specific transcription of a polynucleotide sequence. The term "expression control (regulatory) sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a second molecule in a sample or organism but does not substantially recognize or adhere to other structurally unrelated molecules in the sample. The term "specifically binds," as used herein with respect to an antibody, refers to an antibody which recognizes a specific antigen, but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A" and the antibody, will reduce the amount of labeled A bound to the antibody.

"NFAT promoter" refers to one or more NFAT responsive elements linked to a minimal promoter of any gene expressed by T-cells. In embodiments, the minimal promoter of a gene expressed by T-cells is a minimal human IL-2 promoter. The NFAT responsive elements comprise one or more binding motifs that NFAT proteins, such as NFAT1, NFAT2, NFAT3, and/or NFAT4, bind. The NFAT promoter (or a functional portion or functional variant thereof) can comprise any number of binding motifs, e.g., at least two, at least three, at least four, at least five, or at least six, at least seven, at least eight, at least nine, at least ten, at least eleven, or up to twelve binding motifs. In embodiments, the NFAT promoter comprises six NFAT binding motifs. In an especially preferred embodiment, the NFAT promoter nucleotide sequence comprises or consists of SEQ ID NO: 93 or a functional portion or functional variant thereof.

The NFAT promoter (or a functional portion or functional variant thereof) is operatively associated with the nucleotide sequence encoding FLT3L (or a functional portion or functional variant thereof). "Operatively associated with" means that the nucleotide sequence encoding FLT3L (or a functional portion or functional variant thereof) is transcribed into FLT3L mRNA when the NFAT protein binds to the NFAT promoter sequence (or a functional portion or functional variant thereof). Without being bound to a particular theory, it is believed that NFAT is regulated by a calcium signaling pathway. In particular, it is believed that TCR stimulation (by, e.g., an antigen) and/or stimulation of the calcium signaling pathway of the cell (by, e.g., PMA/Ionomycin) increases intracellular calcium concentration and activates calcium channels. It is believed that the NFAT protein is then dephosporylated by calmoduin and translocates to the nucleus where it binds with the NFAT promoter sequence (or a functional portion or functional variant thereof) and activates downstream gene expression. By providing an NFAT promoter (or a functional portion or functional variant thereof) that is operatively associated with the nucleotide sequence encoding FLT3L (or a functional portion or functional variant thereof), the nucleic acids of the invention advantageously make it possible to express FLT3L (or a functional portion or functional variant thereof) only when the host cell including the nucleic acid is stimulated by, e.g., PMA/Ionomycin and/or an antigen. More information can be found at U.S. Pat. No. 8,556,882, which is incorporated by the reference.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation," refers to a primary response induced by binding of a stimulatory molecule (e.g., a TCR/CD3 complex) with its cognate ligand thereby mediating a signal transduction event, such as signal transduction via the TCR/CD3 complex. Stimulation can mediate altered expression of certain molecules, such as downregulation of TGF-β, and/or reorganization of cytoskeletal structures.

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex. The stimulatory molecule includes a domain responsible for signal transduction.

The term "stimulatory ligand" refers to a ligand that when present on an antigen presenting cell (e.g., an APC, a dendritic cell, a B-cell, and the like.) can specifically bind with a cognate binding partner (referred to herein as a "stimulatory molecule") on a cell, for example a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to a treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease and its severity and the age, weight, etc., of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected"

or "transformed" or "transduced" cell is one which has been transfected, transformed, or transduced with exogenous nucleic acid. The cell includes the primary subject cell and its progeny.

The term "vector" refers to a polynucleotide that comprises an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate the transfer of nucleic acid into cells, such as, for example, polylysine compounds, liposomes, and the like. Examples of viral vectors include adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

A "chimeric antigen receptor" (CAR) molecule is a recombinant polypeptide including at least an extracellular domain, a transmembrane domain and a cytoplasmic domain or intracellular domain. In embodiments, the domains of the CAR are on the same polypeptide chain, for example a chimeric fusion protein. In embodiments, the domains are on different polypeptide chains, for example the domains are not contiguous.

The extracellular domain of a CAR molecule includes an antigen binding domain. The antigen binding domain is for expanding and/or maintaining the modified cells, such as a CAR T cell or for killing a tumor cell, such as a solid tumor. In embodiments, the antigen binding domain for expanding and/or maintaining modified cells binds an antigen, for example, a cell surface molecule or marker, on the surface of a WBC. In embodiments, the WBC is a granulocyte, monocyte and or lymphocyte. In embodiments, the WBC is a lymphocyte, for example, a B cell. In embodiments, the WBC is a B cell. In embodiments, the cell surface molecule of a B cell includes CD19, CD22, CD20, BCMA, CD5, CD7, CD2, CD16, CD56, CD30, CD14, CD68, CD11b, CD18, CD169, CD1c, CD33, CD38, CD138, or CD13. In embodiments, the cell surface molecule of the B cell is CD19, CD20, CD22, or BCMA. In embodiments, the cell surface molecule of the B cell is CD19.

Modified cells (e.g., T-cells) may be derived from a stem cell. The stem cells may be adult stem cells, embryonic stem cells, more particularly non-human stem cells, cord blood stem cells, progenitor cells, bone marrow stem cells, induced pluripotent stem cells, totipotent stem cells or hematopoietic stem cells. A modified cell may also be a dendritic cell, a NK-cell, a B-cell or a T-cell selected from the group consisting of inflammatory T-lymphocytes, cytotoxic T-lymphocytes, regulatory T-lymphocytes or helper T-lymphocytes. In embodiments, modified cells may be derived from the group consisting of CD4+T-lymphocytes and CD8+T-lymphocytes. Prior to expansion and genetic modification of the cells of the invention, a source of cells may be obtained from a subject through a variety of non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In embodiments of the present invention, any number of T cell lines available and known to those skilled in the art, may be used. In embodiments, modified cells may be derived from a healthy donor, from a patient diagnosed with cancer or from a patient diagnosed with an infection. In embodiments, modified cell is part of a mixed population of cells which present different phenotypic characteristics.

The term "stem cell" refers to any of certain types of cell which have the capacity for self-renewal and the ability to differentiate into other kind(s) of cell. For example, a stem cell gives rise either to two daughter stem cells (as occurs in vitro with embryonic stem cells in culture) or to one stem cell and a cell that undergoes differentiation (as occurs e.g. in hematopoietic stem cells, which give rise to blood cells). Different categories of stem cell may be distinguished on the basis of their origin and/or on the extent of their capacity for differentiation into other types of cell. For example, stem cell may include embryonic stem (ES) cells (i.e., pluripotent stem cells), somatic stem cells, Induced pluripotent stem cells, and any other types stem cells.

The pluripotent embryonic stem cells may be found in the inner cell mass of a blastocyst and have high innate capacity for differentiation. For example, pluripotent embryonic stem cells may have the potential to form any type of cell in the body. When grown in vitro for long periods of time, ES cells maintain pluripotency: progeny cells retain the potential for multilineage differentiation.

Somatic stem cells may include the fetal stem cells (from the fetus) and adult stem cells (found in various tissues, such as bone marrow). These cells have been regarded as having a capacity for differentiation lower than that of the pluripotent ES cells—with the capacity of fetal stem cells being greater than that of adult stem cells; they apparently differentiate into only a limited range of types of cell and have been described as multipotent. The 'tissue-specific' stem cells normally give rise to only one type of cell. For example, embryonic stem cells may be differentiated into blood stem cells (e.g., Hematopoietic stem cells (HSCs)), which may be further differentiated into various blood cells (e.g., red blood cells, platelets, white blood cells, etc.).

Induced pluripotent stem cells (i.e., iPS cells or iPSCs) may include a type of pluripotent stem cell artificially derived from a non-pluripotent cell (e.g., an adult somatic cell) by inducing a expression of specific genes. Induced pluripotent stem cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells may be made from adult stomach, liver, skin cells and blood cells.

In embodiments, the modified cells are engineered to express one or more molecules (e.g., CAR and therapeutic agent). For example, the modified cells may include a polynucleotide encoding the one or more molecules. In embodiments, the polynucleotide may integrate into the genome of the modified cell and descendants of the modified cell will also express the polynucleotide, resulting in a stably transfected modified cell. In embodiments, the modified cell may express the polynucleotide encoding the CAR but the polynucleotide does not integrate into the genome of the modified cell such that the modified cell expresses the transiently transfected polynucleotide for a finite period of time (e.g., several days), after which the polynucleotide is lost through cell division or other factors. For example, the polynucleotide is present in the modified cell in a recombinant DNA construct, in an mRNA, or in a viral vector, and/or the polynucleotide is an mRNA, which is not integrated into the genome of the modified cell. In embodiments, expression of the polynucleotide is regulated or modulated by a synthetic Notch receptor comprising, from N-terminal to C-terminal and in covalent linkage: a) an extracellular domain comprising an antibody (e.g., a single-chain Fv (scFv) or a nanobody) that specifically binds to an antigen; b) a Notch regulatory region (NRR) and c) an intracellular domain comprising a transcriptional activator comprising a DNA binding domain. In embodiments, the Notch regulatory region comprises a Lin 12-Notch repeat, a heterodimerization domain comprising an S2 proteolytic cleavage site and a transmembrane domain comprising an S3 proteolytic cleavage site. The intracellular domain is heterologous to the Notch regulatory region. In embodiments, the transcriptional activator replaces a naturally-occurring intracellular notch domain, and binding of the antibody to the antigen induces cleavage at the S2 and S3 proteolytic cleavage sites, thereby releasing the intracellular domain. The release of the intracellular domain causes the transcriptional activator to induce expression of the polynucleotide encoding one or more target proteins in the modified cell. In embodiments, the modified cell comprises a polynucleotide encoding the synthetic Notch receptor and a polynucleotide encoding a transcriptional control element that is responsive to the transcriptional activator and operably linked to the polynucleotide encoding one or more target proteins (e.g., CAR and scFv targeting M2).

Embodiments relate to a method or use of polynucleotide. The method or use includes: providing a viral particle (e.g., AAV, lentivirus or their variants) comprising a vector genome, the vector genome comprising the polynucleotide, wherein the polynucleotide is operably linked to an expression control element conferring transcription of the polynucleotide; and administering an amount of the viral particle to the subject such that the polynucleotide is expressed in the subject. In embodiments, the AAV preparation may include AAV vector particles, empty capsids and host cell impurities, thereby providing an AAV product substantially free of AAV empty capsids. More information of the administration and preparation of the viral particle may be found at the U.S. Pat. No. 9,840,719 and Milani et al., Sci. Transl. Med. 11, eaav7325 (2019) 22 May 2019, which are incorporated herein by reference.

In embodiments, the bioreactor may be inoculated at a cell density of approximately 0.5×10$^6$ cells/mL with viability greater than 95%. When the cell density reaches approximately 1.0×10$^6$ cells/mL, the cells may be transfected with the PEI/DNA complexes (polyplexes) with a PEI to DNA ratio of 2:1. At the time of harvest, AAV from the cell culture in the bioreactor may be released using the Triton X-100 method. All solutions may be added directly to the bioreactor, and the lysate was centrifuged at 4000×g for 20 min. The supernatant may be stored at −80° C. for further processing. AAV may be further purified. For example, AAV samples (12.3 mL) may be purified by overlaying them on top of series of step gradients using 15, 25, 40 and 54% iodixanol concentrations containing 1, 5, 7 and 5 mL, respectively. The 15% iodixanol concentration also contains 1 M NaCl to avoid aggregation of AAV with other cellular proteins and negatively charged nuclear components. After the completion of centrifugation, 5 mL may be withdrawn from 2 mm below the 40/54 interface marked before starting the ultracentrifugation at 385,000×g for 1 h 45 min in Sorvals T-865 rotor in Sorval Ultracentrifuge. The viral vectors may be then quantified. For example, vectors AAV infectivity may be determined by the gene transfer assay (GTA)using GFP as a reporter gene in all cases. AAV infectivity assay where sample may be diluted before addition to the cells to have the GFP positive cells in the range of 2-20% to assure that only single virus has entered the cell for GFP expression. The GFP-positive cells may be quantified by FACS using HEK293 cells in suspension. The AAV may be then administrated to a subject. For example, AAV may be diluted in 0.9% sterile NaCl saline solution (supplemented with 0.25% human serum albumin [HSA]) for infusion in patients and the final volume of infusion will be calculated based on the patient's weight as 3 mL/kg.

In embodiments, expression of the one or more molecules may be regulated by an inducible expression system. The inducible expression system allows for a temporal and spatial controlled activation and/or expression of genes. For example, Tetracycline-Controlled Transcriptional Activation is a method of inducible gene expression where transcription is reversibly turned on or off in the presence of the antibiotic tetracycline or one of its derivatives (e.g., doxycycline). For example, an inducible suicide gene expression system allows for a temporal and spatial controlled activation and/or expression of a suicide gene, which causes a cell to kill itself through apoptosis. "Suicide gene" is a nucleic acid coding for a product, wherein the product causes cell death by itself or in the presence of other compounds. A representative example of such a therapeutic nucleic acid (suicide gene) is one which codes for thymidine kinase of herpes simplex virus (HSV-TK). Additional examples are thymidine kinase of varicella zoster virus and the bacterial gene cytosine deaminase which can convert 5-fluorocytosine to the highly toxic compound 5-fluorouracil.

In embodiments, the modified cells comprise a nucleic acid sequence encoding a reverse tetracycline transactivator (rtTA). In embodiments, expression of the one or more molecules is regulated by the rtTA, such that the one or more molecules are expressed in the presence of tetracycline. In embodiments, a concentration of tetracycline in the cell culture medium is not less than about 2 pg/ml. In embodiments, the tetracycline is selected from the group consisting of tetracycline, demeclocycline, meclocycline, doxycycline, lymecycline, methacycline, minocycline, oxytetracycline, rolitetracycline, and chlortetracycline. In embodiments, the tetracycline is doxycycline.

In embodiments, the inducible suicide system is an HSV-TK system or an inducible caspase-9 system. In embodiments, the modified cells comprise a nucleic acid sequence encoding a suicide gene, such that when the modified cells are in the presence of a nucleoside analogue in a manner permitting expression of the suicide gene, to render the nucleoside analogue cytotoxic to the modified cells. In embodiments, the suicide gene is selected from the group consisting of thymidine kinase of herpes simplex virus, thymidine kinase of varicella zoster virus, and bacterial cytosine deaminase. In embodiments, the suicide gene is thymidine kinase of herpes simplex virus. In embodiments, the nucleoside analogue is selected from the group consisting of ganciclovir, acyclovir, buciclovir, famciclovir, penciclovir, valciclovir, trifluorothymidine, 1-[2-deoxy, 2-fluoro, beta-D-arabino furanosyl]-5-iodouracil, ara-A, araT 1-beta-D-arabinofuranoxyl thymine, 5-ethyl-2'-deoxyuridine, 5-iodo-5'-amino-2,5'-dideoxyuridine, idoxuridine, AZT, AIU, dideoxycytidine, and AraC. In embodiments, the nucleoside analogue is ganciclovir.

In embodiments, expression of the one or more molecules is regulated by one or more promoters. In embodiments, the polynucleotide comprises a promoter comprising a binding site for a transcription modulator that modulates the expression and/or secretion of the one or more molecules in the cell. For example, the transcription modulator is or includes Hif1a, NFAT, FOXP3, and/or NFkB. For example, the one or more molecules comprise at least one cytokine associated with an oxygen-sensitive polypeptide domain, and the oxygen-sensitive polypeptide domain comprises HIF VHL binding domain.

In embodiments, the antigen binding domain for killing a tumor, binds an antigen on the surface of a tumor, for example a tumor antigen or tumor marker. Tumor antigens are proteins that are produced by tumor cells that elicit an immune response, particularly T cell mediated immune responses. Tumor antigens are well known in the art and include, for example, tumor associated MUC1 (tMUC1), a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, surviving, telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, CD19, and mesothelin. For example, when the tumor antigen is CD19, the CAR thereof can be referred to as CD19CAR, which is a CAR molecule that includes a antigen binding domain that binds CD19.

In embodiments, the extracellular antigen binding domain of a CAR includes at least one scFv or at least a single domain antibody. As an example, there can be two scFvs on a CAR. The scFv includes a light chain variable (VL) region and a heavy chain variable (VH) region of a target antigen-specific monoclonal antibody joined by a flexible linker. Single chain variable region fragments can be made by linking light and/or heavy chain variable regions by using a short linking peptide (Bird et al., Science 242:423-426, 1988). An example of a linking peptide is the GS linker having the amino acid sequence (GGGGS)$_3$ (SEQ ID NO: 278), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

The cytoplasmic domain of the CAR molecules described herein includes one or more co-stimulatory domains and one or more signaling domains. The co-stimulatory and signaling domains function to transmit the signal and activate molecules, such as T cells, in response to antigen binding. The one or more co-stimulatory domains are derived from stimulatory molecules and/or co-stimulatory molecules, and the signaling domain is derived from a primary signaling domain, such as the CD3 zeta domain. In embodiments, the signaling domain further includes one or more functional signaling domains derived from a co-stimulatory molecule. In embodiments, the co-stimulatory molecules are cell surface molecules (other than antigens receptors or their ligands) that are required for activating a cellular response to an antigen.

In embodiments, the co-stimulatory domain includes the intracellular domain of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, or any combination thereof. In embodiments, the signaling domain includes a CD3 zeta domain derived from a T cell receptor.

The CAR molecules described herein also include a transmembrane domain. The incorporation of a transmembrane domain in the CAR molecules stabilizes the molecule. In embodiments, the transmembrane domain of the CAR molecules is the transmembrane domain of a CD28 or 4-1BB molecule.

Between the extracellular domain and the transmembrane domain of the CAR, there may be incorporated a spacer domain. As used herein, the term "spacer domain" generally means any oligo- or polypeptide that functions to link the transmembrane domain to the extracellular domain and/or the cytoplasmic domain on the polypeptide chain. A spacer domain may include up to 300 amino acids, preferably 10 to 100 amino acids, and most preferably 25 to 50 amino acids.

Embodiments relate to an isolated nucleic acid sequence comprising a nucleic acid sequence and an additional nucleic acid sequence, the nucleic acid sequence encoding a binding molecule, the additional nucleic acid sequence encoding a therapeutic agent that is or comprises an inflammatory cytokine or a fusion protein associated with the inflammatory cytokine. In embodiments, the binding molecule is a Chimeric antigen receptor (CAR) or a modified TCR. Embodiments relate to a population of CAR cells comprising the nucleic acid sequence and the additional nucleic acid sequence of, wherein the CAR cells comprise lymphocyte, leukocyte, or PBMC; or cells, NK cells, or dendritic cells. Embodiments relate to a population of CAR cells comprising the nucleic acid sequence and the additional nucleic acid sequence of one of embodiments 2 and 3, wherein the CAR cells are T cells, NK cells, or dendritic cells.

Inflammatory cytokines mobilize and activate dendritic cells (DCs), which are essential for efficacious T cell priming and immune responses that clear the infection. inflammatory cytokines have been shown to also enhance DC migration and proliferation and may regulate DC activation state. Example of inflammatory cytokines may include IFN- γ, TNF-α, Fms-related tyrosine kinase 3 ligand (FLT3L), GM-CSF and CCL20. Example of professional APCs include DCs, B-lymphocytes, monocytes, and macrophages. In embodiments, the modified cells may enhance APC (e.g., DC) migration and proliferation and may regulate APC activation state, thereby enhancing T cell therapy. Accordingly, CAR T cells described herein may recruit professional APCs such as dendritic cells and mononuclear macrophages at the tumor site as well as accumulate APC phagocytose tumor antigens at the tumor site and secrete pro-inflammatory factors, recruiting and activating CART cells and other tumor-infiltrating lymphocytes and therefore enhancing anti-tumor ability.

In embodiments, the CAR and the inflammatory cytokine are produced in the form of a polyprotein, which is cleaved to generate separate CAR and inflammatory cytokine molecules. In embodiments, the polyprotein comprises a cleavable moiety between the CAR and the therapeutic agent, the cleavable moiety comprises a 2A peptide, the 2A peptide comprises P2A or T2A, and/or the CAR and the therapeutic agent are each constitutively expressed. In embodiments, the CAR cells comprise: a third nucleic acid sequence encoding an additional CAR binding to an antigen that is different from an antigen that the CAR binds, or the additional CAR binding a solid tumor antigen, and the CAR binds an antigen of a white blood cell, and/or wherein the solid tumor antigen is tMUC 1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, PSCA, or EGFR, and the B cell antigen is CD19, CD20, CD22, or BCMA.

In embodiments, a T cell clone that expresses a TCR with a high affinity for the target antigen may be isolated. Tumor-infiltrating lymphocytes (TILs) or peripheral blood mononuclear cells (PBMCs) can be cultured in the presence of antigen-presenting cells (APCs) pulsed with a peptide representing an epitope known to elicit a dominant T cell response when presented in the context of a defined HLA allele. High-affinity clones may be then selected on the basis of MHC-peptide tetramer staining and/or the ability to recognize and lyse target cells pulsed with low titrated concentrations of cognate peptide antigen. After the clone has been selected, the TCRα and TCRβ chains or TCRγ and TCRδ chains are identified and isolated by molecular cloning. For example, for TCRα and TCRβ chains, the TCRα and TCRβ gene sequences are then used to generate an expression construct that ideally promotes stable, high-level expression of both TCR chains in human T cells. The transduction vehicle, for example, a gammaretrovirus or lentivirus, can then be generated and tested for functionality (antigen specificity and functional avidity) and used to produce a clinical lot of the vector. An aliquot of the final product can then be used to transduce the target T cell population (generally purified from patient PBMCs), which is expanded before infusion into the patient.

Various methods may be implemented to obtain genes encoding tumor-reactive TCR. More information is provided in Kershaw et al., Clin Transl Immunology. 2014 May; 3(5): e16. In embodiments, specific TCR can be derived from spontaneously occurring tumor-specific T cells in patients. Antigens included in this category include the melanocyte differentiation antigens MART-1 and gp100, as well as the MAGE antigens and NY-ESO-1, with expression in a broader range of cancers. TCRs specific for viral-associated malignancies can also be isolated, as long as viral proteins are expressed by transformed cells. Malignancies in this category include liver and cervical cancer, associated with hepatitis and papilloma viruses, and Epstein-Barr virus-associated malignancies. In embodiments, target antigens of the TCR may include CEA (e.g., for colorectal cancer), gp100, MART-1, p53 (e.g., for Melanoma), MAGE-A3 (e.g., Melanoma, esophageal and synovial sarcoma), NY-ESO-1 (e.g., for Melanoma and sarcoma as well as Multiple myelomas).

In embodiments, preparation and transfusion of tumor infiltrating lymphocytes (TIL) may be implemented by the following. For example, tumor tissue comes from surgical or biopsy specimens, may be obtained under aseptic conditions and transported to the cell culture chamber in ice box. Necrotic tissue and adipose tissue may be removed. The tumor tissue may be cut into small pieces of about 1-3 cubic millimeter. Collagenase, hyaluronidase and DNA enzyme may be added, and digested overnight at 4° C. Filtering with 0.2 um filter, cells may be separated and collected by lymphocyte separation fluid, 1500 rpm for 5 min. Expanding the cells with a culture medium comprising PHA, 2-mercaptoethanol and CD3 monoclonal antibody, a small dose of IL-2 (10-20 IU/ml) may be added to induce activation and proliferation. According to the growth situation, the cell density may be carefully detected and maintained within the range of $0.5-2\times10^6$/ml under the condition of 37° C. and 5% $CO_2$ for 7-14 days. TIL positive cells have the ability to kill homologous cancer cell may be screened out by co-culture. The positive cells may be amplified in a serum-free medium containing a high dose of IL2 (5000-6000 IU/ml) until greater than $1\times10^{11}$ TILs may be obtained. To administer TILs, they may be first collected in saline using continuous-flow centrifugation and then filtered through a platelet-administration set into a volume of 200-300 mL containing 5% albumin and 450 000 IU of IL-2. The TILs may be infused into patients through a central venous catheter over a period of 30-60 minutes. In embodiments, TILs may be often infused in two to four separate bags; the infusions may be separated by several hours.

Embodiments relate to a pharmaceutical composition comprising the population of the CAR cells. Embodiments relate to a method of causing or promoting or stimulating a T cell response in a subject in need thereof and/or treating a tumor of the subject, the method comprising administering an effective amount of the composition to the subject.

In embodiments, the inflammatory cytokine is or comprises Fms-related tyrosine kinase 3 ligand (FLT3L), GM-CSF and CCL20. In embodiments, the therapeutic agent is or comprises FLT3L. In embodiments, the therapeutic agent comprises the SEQ ID NO: 94 or 95. In embodiments, the therapeutic agent is or comprises GM-CSF. In embodiments, the therapeutic agent comprises the SEQ ID NO: 96.

FLT3L has the function of promoting the proliferation and activation of dendritic cells and has been shown in the literature. GM-CSF may recruit mononuclear macrophages for enrichment at the tumor site. Therefore, expression of FLT3L or GM-CSF in CART cells, which may be sustained overexpression by IRES or 2A, or induced by NFAT or NF-κB promoter. In embodiments, FLT3L or GM-CSF may be a soluble form of the protein, or it may be in the form of a cell membrane that is added to the transmembrane structure. In embodiments, modified T cells expressing FLT3L or GM-CSF may be further introduced with one or more CARs. For example, modified T cells may include anti-CD19 CAR and/or CAR targeting solid tumor. CD19 CAR T cell kill B cells in the body, causing inflammatory reactions in the body and promoting the proliferation and migration of APC. While APCs present lysed B cell antigens, they may not activate immune cells against solid tumors. Since modified CAR T cells bind to solid tumor antigens, express FLT3L or GM-CSF may be mainly concentrated in the solid tumor sites. Thus, APCs in the body may be recruited to the solid tumor site as well as phagocytose solid tumor cells and present solid tumor antigen or neo-antigen, activating tumor infiltrating lymphocytes to participate in anti-solid tumor inflammation and promote tumor collapse.

In embodiments, FEL3L or GM-CSF may be continuously expressed by 2A, IRES. Alternatively, the NFκB promoter may be used to conditionally express FLT3L or GM-CSF by NFAT. And FLT3L and GM-CSF may be in a form of soluble proteins or associated or anchored to the cell membrane of the CAR T cells. Such CAR T cells can activate dendritic cells, monocytes/macrophages and release myeloid-derived cytokines such as IL6, IL12, etc., in the case of co-culture and activation with PBMC. In turn, CAR T cells are more activated to release IL2, IFNγ, GzmB, and the like.

In embodiments, anti-CD19 CART cells expressing FEL3L or GM-CSF and CD19-positive Nalm6 cells may be co-cultured, and monocytes may be added. For example, the monocytes are activated, and IL12 is released. When the monocytes are separated again, anti-solid tumor CAR T expressing FEL3L or GM-CSF and the cells expressing solid tumor antigens may be co-cultured, which detect higher levels of IFNγ, IL2, IL6, IL12 as compared to CAR T without expressing FEL3L and GM-CSF.

In embodiments, the fusion protein comprises the inflammatory cytokine, a linker, an extracellular domain, a transmembrane domain, and a cytoplasmic domain, wherein the transmembrane domain is selected from a group consist of a transmembrane domain of the receptor of IL15, IL2, IL7, IL6, IL12, IL18, IL21, IL23, IL 33, TNFα, TNFβ, IFNα, and IFNβ, and the cytoplasmic domain is selected from a group consist of a cytoplasmic domain of a receptor of IL15, IL2, IL7, IL6, IL12, IL18, IL21, IL23, IL 33, TNFα, TNFβ, IFNα, and IFNβ, and the extracellular domain is selected from a group consist of an extracellular domain of the receptor of IL15, IL2, IL7, IL6, IL12, IL18, IL21, IL23, IL 33, TNFα, TNFβ, IFNα, and IFNβ. In embodiments, the fusion protein comprises the inflammatory cytokine, a linker, a transmembrane domain, and a cytoplasmic domain, wherein the transmembrane domain is selected from a group consist of a transmembrane domain of a receptor of CD4, CD8, CD28, CD27, CD25, CD137, PD1 and PDL1, and the cytoplasmic domain is selected from a group consist of a cytoplasmic domain of a receptor of CD4, CD8, CD28, CD27, CD25, CD137, PD1 and PDL1. In embodiments, the link is a GS linker.

In embodiments, expression of the additional nucleic acid sequence is regulated by a conditional expression system such that the therapeutic agent is expressed in response to binding of a target antigen. In embodiments, expression of the additional nucleic acid sequence is regulated by Syn-Notch polypeptide. In embodiments, the modified cell or the T cells comprise an additional CAR binding a solid tumor antigen, and the CAR binds an antigen of a white blood cell. In embodiments, the modified cell or the T cells comprise a dominant negative PD-1. In embodiments, the modified cell or the T cells comprise a modified PD-1 lacking a functional PD-1 intracellular domain.

In embodiments, the CAR comprises an extracellular domain, a transmembrane domain, and an intracellular domain, the extracellular domain binds an antigen. In embodiments, the intracellular domain comprises a costimulatory signaling region that comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and one combination thereof. In embodiments, the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

In embodiments, the therapeutic agent is present in the modified cell in a recombinant DNA construct, in an mRNA, or in a viral vector. In embodiments, the modified cell comprises a therapeutic agent mRNA encoding the therapeutic agent, and the mRNA is not integrated into the genome of the modified cell. In embodiments, the modified cell comprises a nucleic acid sequence comprising or the isolated nucleic acid sequence comprises a promoter comprising a binding site for a transcription modulator that modulates the expression and/or secretion of the therapeutic agent in the cell. In embodiments, the transcription modulator is or includes Hif1a, NFAT, FOXP3, and/or NFkB. In embodiments, the promoter is responsive to the transcription modulator. In embodiments, the promoter is operably linked to the nucleic acid sequence encoding the therapeutic agent such that the promoter drives expression and/or secretion of the therapeutic agent in the cell.

In embodiments, expression of the therapeutic agent is regulated by an inducible gene expression system. In embodiments, the inducible gene expression system comprises or is a lac system, a tetracycline system, or a galactose system. In embodiments, the inducible gene expression system comprises or is a tetracycline system. In embodiments, the inducible gene expression system comprises or is a tetracycline on system, and an inducer is tetracycline, doxycycline, or an analog thereof.

Embodiments relate to a method of enhancing expansion of cells in a subject or treating the subject having cancer, the method comprising: administering an effective amount of a composition to the subject having a form of cancer expressing a tumor antigen, the composition comprising a first population of cells comprising a first CAR binding a first antigen, and a second population of cells comprising the therapeutic agent and the binding molecule that binds a second antigen, wherein the second antigen is a tumor antigen and is different from the first antigen.

In embodiments, the first antigen is CD19, CD22, CD20, BCMA, CDS, CD7, CD2, CD16, CD56, CD30, CD14, CD68, CD11b, CD18, CD169, CD1c, CD33, CD38, CD138, or CD13, and/or the solid tumor antigen is tMUC 1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, B7-H3, or EGFR.

Embodiments relate to compositions and methods of modulating lymphocytes' activities and functions (e.g., T cells). Embodiments relate to a modified cell comprising an antigen binding molecule; and a disruption in an endogenous gene associated with T cell apoptosis. In embodiments, the gene comprises at least one of CD80, Fas, Bcl-2, Bax, PI3K, AKT, C-jun, C-fos, C-myc, Gata3, Tox, Mt2 & Pdcd4. In addition to inhibiting the function of CART cells through the classical PD-L1/PD-1 pathway, PD-L1 expressed by tumor cells can also inhibit the function of CART cells by binding to CD80 cells of CART cells, resulting in a decrease in anti-tumor function of CART cells. PD-L1 binds specifically to CD80 (B7-1) to inhibit T cell function, and PD-L1 binds to CD80 of activated CD8 T cells leading to T cell apoptosis. In this decade, immunological checkpoint therapy is well obtained. Efficacy, especially the PD1/PDL1 pathway and the CD28/CTLA4 pathway. However, in the experiment, it was found that the inhibition of T cell by PD1/PDL1 pathway was excluded, and T cells were still inhibited by PDL1/CD80 pathway, but there was no report on inhibiting PDL1/CD80 pathway to improve the anticancer effect of CART. Thus, increasing the anti-tumor ability of CART cells by over-expressing dominantly inactivated CD80 or knocking down CD80 of CART cells. We overexpressed dominant negative CD80 in CART cells (may be intracellular signal domain inactivating mutations) (but no signal sites are reported), which can be deleted from the intracellular domain), compete with endogenous CD80 for binding to PDL1, but do not transmit inhibitory signals, or knock down or knock out CD80 in CART cells. Repressing the inhibition of CART cells by the PDL1/CD80 signaling pathway. Another benefit of overexpression of dominant negative CD80 is the binding of in cis to T cells to PDL1, which abolishes the inhibition of T cell's own PDL1/CD80 pathway and attenuates PDL1 inhibition between T cells and T cells (T The cell itself also expresses PDL1 upon activation. This invention, in combination with dnPD1, can simultaneously disrupt two inhibitory pathways of PDL1 to T cells. CART cell knockout/knockdown, or overexpression of dnCD80, in tumors overexpressing PDL1 The cells were co-cultured and PD1 blocking antibody was added. KART cells knocked out/knocked down, or overexpressing dnCD80, have higher IFNγ/IL2 release and greater proliferative capacity.

Embodiments relate to a modified cell comprising an antigen binding molecule; and an addition or an overexpression of a gene associated with a biosynthesis or transportation pathway of one or more transcription factors playing roles in innate immune responses. In embodiments, the gene comprises at least one of IRF7, IRF3, ILC3s, and RNF2. IRF7 is a lymphoid-specific factor, which is constitutively expressed in the cytoplasm in B cells, pDCs and monocytes in the spleen, thymus, and peripheral blood lymphocytes, and is potently inducible by type I IFNs, virus infection and other stimuli such as 12-o-tetradecanoylphonol-13-acetate, TNFα and lipopolysaccharide in various cell types. The Irf7 gene was originally cloned in 1997, in the context of latent Epstein-Barr virus (EBV) infection where the encoded protein binds to and regulates the EBNA1 Q promoter.21 The human Irf7 gene is located on chromosome 11p15.5, and encodes four isoforms, IRF7A, -B, -C and -D (-H).22 Human IRF7A protein consists of 503 amino acids with molecular size of 55 kD, and mouse IRF7 consists of 457 amino acids with molecular size of 52 kD. IRF3 is the closest family member to IRF7; together they are key regulators of the type I IFN (IFNα/β) responses, which are central to both innate and adaptive immunity. The positive regulatory feedback between IRF7 and type I IFNs during antiviral immune responses is the major source for IRF7 expression in the cell. At the early 'priming' stage of virus infection, the low level of endogenous IRF7 in the cell is phosphorylated and activated by signaling triggered from PRRs, and together with NFκB and IRF3, which are also activated by the same pathways, binds to the virus-responsive elements in the Ifna and Ifnb promoters and induces small amounts of type I IFNs, which secrete and bind to IFNA receptors on other cells. IRF7 has a pivotal role in the priming. Binding of IFNs to IFNA receptor results in the activation of the IFN Janus kinase-signal transducers and activator of transcription signaling cascade, leading to phosphorylation and activation of signal transducers and activator of transcription 1 and −2. The activated signal transducers and activator of transcription ½ then bind to IRF9 as a complex named 'IFN-stimulated gene factor 3', which in turn binds to the IFN-stimulated response element on the IRF7 promoter and induces synthesis of more IRF7. Later, the newly synthesized IRF7 is activated and induces more IFNs so that more and more IRF7 and IFNs are produced, but IRF3 at late stages is degraded by virus infection.

In embodiments, the cell has the disruption in an endogenous gene associated with a biosynthesis or transportation pathway of CD80 and a reduced amount of CD80 as compared to the corresponding wild type of the cell. In embodiments, the disruption is made by a nuclease, siRNA, and/or shRNA. In embodiments, the disruption is made by a zinc finger nuclease (ZFN). In embodiments, the disruption is made by a CRISPR associated protein 9 (Cas9). In embodiments, the disruption is made by a Transcription activator-like effector nuclease (TALEN). In embodiments, the cell has a nucleic acid sequence encoding modified CD80 that lacks a functional intracellular domain as compared to the corresponding wild-type receptor. In embodiments, the modified CD80 is a dominant negative variant of CD80 such that the cell has an altered molecular function of CD80, and/or the modified PD1 is a dominant negative variant of PD1 such that the cell has an altered molecular function of PD1. In embodiments, the modified CD80 is or comprises the amino acid sequence SEQ ID NO: 47 or is a truncated CD80.

In embodiments, the gene is IRF7. In embodiments, the IRF7 is overexpressed as compared to the corresponding wild type of the cell. In embodiments, the genome of the cell comprises a polynucleotide sequence encoding IRF7, the polynucleotide sequence operably linked to a promoter polynucleotide sequence. In embodiments, the genome of the cell comprises a polynucleotide sequence encoding IRF7, the polynucleotide sequence operably linked to a promoter polynucleotide sequence. In embodiments, IRF7 is present in the modified cell in a recombinant DNA construct, in an mRNA, or in a viral vector. In embodiments, the modified cell comprises IRF7 mRNA, and the mRNA is not integrated into the genome of the modified cell. In embodiments, the modified cell comprises a nucleic acid sequence comprising a promoter which comprises a binding site for a transcription modulator that modulates the expression and/or secretion of IRF7 in the cell. In embodiments, the transcription modulator includes Hif1a, NFAT, FOXP3, and/or NFκB. In embodiments, the promoter is responsive to the transcription modulator. In embodiments, the promoter is operably linked to the nucleic acid sequence encoding IRF7 such that the promoter drives expression of the therapeutic agent in the cell. In embodiments, the promoter comprises at least one of SEQ ID Nos: 93 and 124-131.

Embodiments relate to expression modulation of one or more genes in lymphocytes (e.g., T cell, NK cells, and macrophages) to change one or more certain functions of the lymphocytes. Embodiments relate to a method to increase proliferative and/or reconstitute capacities of T cells, the method comprising: providing a T cell; and modulating expression of one or more genes of a T cells, wherein the one or more genes comprise LEF1, CXCR3, FRC, T-bet, PI3K, ezh2, PDCD1, Gfi1, Flt3, FAO, GATA3, Akt, kiaa1324, PDL1, δEF1/ZEB, Kit, Hif-1a Blimp-1, mTOR, fn1, PDL2, FPFIkaros, IL-7R, Hif-2a Myc, Wnt, ITGA9, CTLA4, KLF2, IL-4R, VhI HIF1, Notch1, SMDPD3A, LRBA, HEB, IL-9R PHD1 c-Myb, Notch2, ITPRIPL2, LAG3, MAZR, PDGFRb, PHD2 members of the E2A/HEB family, Activin, PRSS23, Tim3, Tox, gc (II2rg, PHD3 members of the Ikaros family, BMP, CLECL1, BILA, PU.1, IL-2Ra (CD25) FIH1 Ets-family transcription factor PU.1, TGFb, TBX21, CD160, HES1,2,3, IL-2Rb TET2, Runx1, IL7, IKZF2, 2B4, Sox4, PDGFRa, TET1, GATA-2, IL7Ra, EOMES, Foxp3, E12, Pdgfa, TET3, TCF-1 (Tcf7) 1L12, PRDM1, ccr4, E2-2 Pdgfb, DNMT3a, RBPSuh IL15, BTLA, PVRIG, E47, Pdgfc, DNMT3b, 1d3, IL6, CD244, CD16B, MEF2, Pdgfd, DNMT3c, 1d2, IL2, KL6, SIVA1, Nur77/Nor1, TGF-b1, Runx1, MAPK, JUNB, CD33, Ncoa4, TGF-b2 Runx3, AMPK, FOSB, LAGLS9, Basp2, TGF-b3 EBF, NF-Kb, FAM13A, CD122, Pitx1, BMP2, Pax5, NF-AT, BATF3, ID01, Prdm16, BMP4, FOG-1, AP-1, KLRC1, IDO2, Ndn, BMP7, GATA-3, PI-3 kinase, Akt/PKB, and Ras/MAP, KLRC2, CD45, Irf6, ActivinbetaA, GATA-2, CCR7, ZNF704, CVPLBL, Dach1, ALK-5, GATA-1 STAT1, CTHRC1, TNFAIP8L2, Nr4a2, BMPR-1A/B, Groucho/TLE/Grg family proteins or Sin3A, STAT2, FAXC, DNMT3A, Hoxa5, BMPR-II, Helios, STAT3, EGR1, CEACAM-1, Hoxb5, TLR, NFAT, STAT4, RBM47, RUNX3, FoxN1, MyD88, Bcl-6, STATS, ENTPD1, LEXM, Gli1,2,3, SHH, BCL-6b (BAZF), glut1, SUV39H1, PILRA, Smoothen, HIF1, AKAP5, PTNNS1L3, Ptch1, c-Myc, β-catenin, Fegr3a, Fu, IRF4, PI3K, Nat8, Su(fu), NF-kb, GLUL, ccl9, Wnt1,3,4,5b,10b, ThPOK, FAXC, HCK, Smad, Oct3/4, TREM2, CXCL10, Nanog, LNGM, CCL6, CXCL9, Sox2, NUDT16, CD36, INFa,b, KLF4, IGF1, CXCR3, FOXO1, CTSS, CCL5, TSC1, GZMC, CCR5, OxPhos, BATF, CCR7, Zbtb32, CXCL2, SOCS1, E2F2, TNFAIP8L3, SOCS2, SMART, IL-1b, SOCS3, NCOR, IL-1a, SOCS4, TRPV1, SOCS5, TRPV2, SOCS6, TRPV3, SOCS7, TRPV4, CIS, Rgs1, CCR1, PLSCR1, CCR2, ITGB1, CCR3, ITGB2, CCR4, C3AR1, GPCR75, ITGA3, IL-6R, ITGA5, GP130, ITGAL, STAT3, CARD11, MCL1, CD83, PIM-1, CXCL1, CXCL2, CXCR1, CXCR2, CXCR4, IL-1b, and IL-1bR.

In embodiments, the T cells include a dominant negative variant of a receptor associated with a peptide corresponding to the one or more gene above. In embodiments, the modulation is regulated by an inducible expression system. In embodiments, the inducible expression system is a rtTA-TRE system, which increases or activates the expression of the one or more gene. In embodiments, the modified T cells comprise a nucleic acid sequence encoding a suicide gene. In embodiments, the suicide gene is an HSV-TK system. In embodiments, the proliferative and/or reconstitute capacities of T cells are measured based on expression of one or more markers of the T cells. In embodiments, the T cells further include a CAR. For example, Examples of the markers for CAR T cells include CAR that defines the proportion of CAR+ cells, CD8 that defines the proportion of CD8/CD4 cells, CD45RO indicating memory cell/effector cell, CCR7 indicating memory cell/effector cell, CD27 indicating memory cells/effector cells/degree of differentiation, HLA-DR indicating T cell activation status, PD1 monitoring cell depletion signals, CD28 indicating cell differentiation potential, and CD25 monitoring cell activation.

In embodiments, CD45RO(RA)/CCR7/HLA-DR: CD45RO and CCR 7 are sufficient to define T-cm/T-em/Te/T-naive 4 population cells. HLD-DR is used to define the activation state of T cells. This method can be used to identify auto-activated cells and to detect CART cell activation in clinical trials. CD27 is thought to be involved in the differentiation state of T cells. The earlier the T cells with high differentiation potential, the higher the expression of CD27. After the addition of Wnt activator, the T cells were entered into the TSCM state by the trigger, and the expression of CD27 was up-regulated. In recent studies, CD27 has a very high correlation with the prognosis. Patients with better prognosis have stronger CD27 expression than patients with poor prognosis. CD27+PD1−CD8+ cells can play a significant anti-tumor effect. CD27 can be used as a product indicator. CD28 is considered to be one of the functional markers of T cells and is often thought to be involved in the potential differentiation potential of T cells. Can be used with CD27. In some reports, cells of CD8+ CD28− are thought to have some functions similar to Tregs. CD25, a member of the IL2R family, is thought to be a marker of T cell activation and is significantly up-regulated upon contact with antigen. Cells of CD27−CD25+CD4+ are considered to be regulatory T cells or are associated with terminal differentiation. Previously, in an article on the treatment of lymphoma, CD25 was also used as one of detection criteria.

Sequences and references listed in the Embodiments and Examples are provided in Table 2.

TABLE 2

| | | | |
|---|---|---|---|
| Sequences and references | | | |
| SEQ ID NO: | Identity | SEQ ID NO: | Identity |
| 1 | SP | 30 | Tumor-associated MUC1 scFv 1 |
| 2 | Hinge & transmembrane domain | 31 | Tumor-associated MUC1 scFv-1 VH |
| 3 | Co-stimulatory region | 32 | Tumor-associated MUC1 scFv-1 VL |
| 4 | CD3-zeta | 33 | Tumor-associated MUC1 scFv 2 |
| 5 | scFV Humanized CD19 | 34 | Tumor-associated MUC1 scFv2 VH |
| 6 | SCFV CD19 | 35 | Tumor-associated MUC1 scFv2 VL |
| 7 | scFv FZD10 | 36 | ED IL2 receptor |
| 8 | scFv TSHR | 37 | ED IL6 receptor |

TABLE 2-continued

Sequences and references

| SEQ ID NO: | Identity | SEQ ID NO: | Identity |
|---|---|---|---|
| 9 | scFv PRLR | 38 | ED IL7 receptor |
| 10 | scFv Muc 17 | 39 | ED IL12 receptor |
| 11 | scFv GUCY2C | 40 | ED IL15 receptor |
| 12 | scFv CD207 | 41 | ED IL21 receptor |
| 13 | Prolactin (ligand) | 42 | ED IL23 receptor |
| 14 | scFv CD3 | 43 | TM IL2 receptor |
| 15 | scFv CD4 | 44 | TM IL6 receptor |
| 16 | scFv CD4-2 | 45 | TM IL7 receptor |
| 17 | scFv CD5 | 46 | TM IL12 receptor |
| 18 | WTCD3zeta | 47 | TM IL15 receptor |
| 19 | WTCD3zeta-BCMACAR full length | 48 | TM IL21 receptor |
| 20 | BCMACAR | 49 | TM IL23 receptor |
| 21 | MUC1CAR | 50 | CD IL2 receptor |
| 22 | m19CAR-IRES-MUC1CAR | 51 | CD IL6 receptor |
| 23 | hCD19CAR-IRES-MUC1CAR | 52 | CD IL7 receptor |
| 24 | hCD22CAR-IRES-MUC1CAR | 53 | CD IL12 receptor |
| 25 | BCMACAR-IRES-MUC1CAR | 54 | CD IL15 receptor |
| 26 | mCD19CAR-2A-MUC1CAR | 55 | CD IL21 receptor |
| 27 | hCD19CAR-2A-MUC1CAR | 56 | CD IL23 receptor |
| 28 | hCD22CAR-2A-MUC1CAR | 57 | TM CD4 |
| 29 | BCMA-2A-MUC1CAR | 58 | TM CD8 |
| 59 | TM CD27 | 78 | IL33 |
| 60 | TM CD28 | 79 | TNFα |
| 61 | TM CD137 | 80 | TNFβ |
| 62 | TM PD1 | 81 | Hif VHL-interaction domain : Hif amino acid 344-417 |
| 63 | TM PDL1 | 82 | Hif amino acid 380-603 |
| 64 | CD CD4 | 83 | GS linker sequence |
| 65 | CD CD8 | 84 | EA linker sequence |
| 66 | CD CD27 | 85 | FLT3L(Natural Membrane Bound Form Nucleotide) |
| 67 | CD CD28 | 86 | FLT3L(Natural Soluble Form Nucleotide) |
| 68 | CD CD137 | 87 | FLT3L ECD (from Natural Membrane Bound Form Nucleotide) |
| 69 | CD PD1 | 88 | CD8 hinge and TM Nucleotide |
| 70 | CD PDL1 | 89 | GM-CSF(Natural soluble form only Nucleotide) |
| 71 | IL2 | 90 | RQR8 Nucleotide |
| 72 | IL6 | 91 | tEGFR Nucleotide |
| 73 | IL7 | 92 | 3xGGGGS Nucleotide |
| 74 | IL12 | 93 | 6x NFAT enhancer + minimal IL-2 promoter Nucleotide |
| 75 | IL15 | 94 | FLT3L(Natural Membrane Bound Form aa) |
| 76 | IL21 | 95 | FLT3L(Natural Soluble Form aa) |
| 77 | IL23 | 96 | FLT3L ECD (from Natural Membrane Bound Form aa) |
| 97 | CD8 hinge and TM aa | 98 | GM-CSF(Natural soluble form only aa) |
| 99 | RQR8 aa | 100 | tEGFR aa |
| 101 | 3xGGGGS aa | 116 | CD80 ECD + TM |
| 102 | CD80 siRNA 1 sense | 117 | CD80 Crispr target 1 |
| 103 | CD80 siRNA 1 anti-sense | 118 | CD80 Crispr target 2 |
| 104 | CD80 siRNA 2 sense | 119 | CD80 Crispr target 3 |
| 105 | CD80 siRNA 2 anti-sense | 120 | CD80 Crispr target 4 |
| 106 | CD80 siRNA 3 sense | 121 | CD80 Crispr target 5 |
| 107 | CD80 siRNA 3 anti-sense | 122 | PD1-mutant |
| 108 | CD80 siRNA 4 sense | 123 | PD1-truncated |
| 109 | CD80 siRNA 4 anti-sense | 124 | 41BB promoter |
| 110 | CD80 siRNA 5 sense | 125 | CD25 enhancer + minimal TK promoter |
| 112 | CD80 siRNA 5 anti-sense | 126 | CD69 enhancer + minimal TK promoter |
| 113 | wtCD80 | 127 | IFN-gamma promoter |
| 114 | CD80 ECD | 128 | NFAT promoter (example 1) Transcription factor binding sites. |
| 115 | CD8 hinge and TM | 129 | NFAT promoter (example 2) Transcription factor binding sites. |
| 130 | NFAT promoter (example 1) the minimal promoter | 131 | NFAT promoter (example 2) the minimal promoter |

TABLE 2-continued

Sequences and references

| SEQ ID NO: | Identity | SEQ ID NO: | Identity |
|---|---|---|---|
| 132 | Vector h19CAR | 133 | Vector H19-bbz-NFAT6x-sFLT3L |
| 134 | Vector H19bbz-2a-sFLT3L | | |

Note:
EM: Extracellular Domain;
TM: Transmembrane Domain;
CD: Cytoplasmic Domain FLT3L/GMCSF co-expressed with solid tumor CAR may be selected form:
1. FLT3L natural membrane anchoring form
2. FLT3L natural membrane anchored form of extracellular segment/natural soluble form + 3xGGGGS (flexible connection, with or without one original design) + CD8 hinge and TM
3. FLT3L natural membrane anchored form of extracellular domain/natural soluble form + 3xGGGGS (with or without one) + RQR8 (RQR8 is a CD34 and CD20 epitope, can be identified by CD34 antibody, cleared with CD20 antibody drug)
4. FLT3L natural membrane anchored form of extracellular domain/natural soluble form + 3xGGGGS (with or without each) + tEGFR (tEGFR is a modified inactivated EGF receptor, which can be recognized and killed by the corresponding antibody)
5. GM-CSF natural soluble form + 3xGGGGS (flexible connection, with or without one original design) + CD8 hinge and TM
6. GM-CSF natural soluble form + 3xGGGGS (with or without each) + RQR8 (RQR8 is a CD34 and CD20 epitope, which can be identified by CD34 antibody and cleared with CD20 antibody)
7. GM-CSF natural soluble form + 3xGGGGS (with or without each) + tEGFR (tEGFR is a modified inactivated EGF receptor that can be recognized and killed by the corresponding antibody)
Related genes can be linked to CAR by 2A or IRES, or induced by 6x NFAT enhancer + minimal IL-2 promoter.

EXEMPLARY EMBODIMENTS

The following are exemplary embodiments:
1. An isolated nucleic acid comprising a nucleic acid sequence and an additional nucleic acid sequence, the nucleic acid sequence encoding a binding molecule, the additional nucleic acid sequence encoding a therapeutic agent that is or comprises an inflammatory cytokine or encoding a fusion protein associated with the inflammatory cytokine.
2. The isolated nucleic acid of embodiment 1, wherein the binding molecule is a Chimeric antigen receptor (CAR) or a modified TCR.
3. A population of CAR cells comprising the nucleic acid sequence and the additional nucleic acid sequence of one of embodiments 2 or 3, wherein the CAR cells comprises lymphocytes, leukocytes, PBMCs, NK cells, or dendritic cells.
4. A population of CAR cells comprising the nucleic acid sequence and the additional nucleic acid sequence of one of embodiments 2 or 3, wherein the CAR cells are T cells, NK cells, or dendritic cells.
5. The population of CAR cells of embodiment 4, wherein the CAR and the inflammatory cytokine are produced in the form of a polyprotein, which is cleaved to generate separate CAR and inflammatory cytokine molecules.
6. The population of CAR cells of one of embodiments 1, 4, or 5, wherein the polyprotein comprises a cleavable moiety between the CAR and the therapeutic agent, the cleavable moiety comprises a 2A peptide, the 2A peptide comprises P2A or T2A, and/or the CAR, and the therapeutic agent and CAR are constitutively expressed.
7. The population of CAR cells of one of embodiments 1, 4, or 5, wherein the CAR cells comprise: a third nucleic acid sequence encoding an additional CAR binding to an antigen that is different from the antigen that the CAR binds, or the additional CAR binds a solid tumor antigen, and the CAR binds an antigen of a white blood cell, and/or wherein the solid tumor antigen is tMUC 1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, QRFPR, GPR119, CLDN6, UPK2, ADAM12, SLC45A3, ACPP, MUC21, MUC16, MS4Al2, ALPP, CEA, EphA2, FAP, GPC3, IL13-Rα2, Mesothelin, PSMA, ROR1, VEGFR-II, GD2, FR-α, ErbB2, EpCAM, EGFRvIII, PSCA, or EGFR, and the B cell antigen is CD19, CD20, CD22, or BCMA.
8. A pharmaceutical composition comprising the population of the CAR cells of one of embodiments 1 or 4-7.
9. A method of causing or promoting or stimulating a T cell response in a subject in need thereof and/or treating a tumor of the subject, the method comprising administering an effective amount of the composition of embodiment 8 to the subject.
10. The isolated nucleic acid, the population of CAR cells, the pharmaceutical composition, or the method of one of embodiments 1-9, wherein the inflammatory cytokine is or comprises Fms-related tyrosine kinase 3 ligand (FLT3L), GM-CSF or CCL20.
11. The isolated nucleic acid, the population of CAR cells, the pharmaceutical composition, or the method of one of embodiments 1-9, wherein the therapeutic agent is or comprises FLT3L.
12. The isolated nucleic acid, the population of CAR cells, the pharmaceutical composition, or the method of one of embodiments 1-9, wherein the therapeutic agent comprises amino acid sequence SEQ ID NO: 94 or 95.
13. The isolated nucleic acid, the population of CAR cells, the pharmaceutical composition, or the method of one of embodiments 1-9, wherein the therapeutic agent is or comprises GM-CSF.
14. The isolated nucleic acid, the population of CAR cells, the pharmaceutical composition, or the method of one of embodiments 1-9, wherein the therapeutic agent comprises amino acid sequence SEQ ID NO: 96.
15. The isolated nucleic acid, the population of CAR cells, the pharmaceutical composition, or the method of one of embodiments 1-14, wherein the fusion protein comprises the inflammatory cytokine, a linker, an extracellular domain, a transmembrane domain, and a cytoplasmic domain, wherein the transmembrane domain is selected from the group consisting of a transmembrane domain of the receptor of IL15, IL2, IL7, IL6, IL12, IL18, IL21, IL23, IL 33, TNFα, TNFβ, IFNα, and IFNβ, the cytoplasmic domain is selected from the group consisting of a cytoplasmic domain of a receptor of IL15, IL2, IL7, IL6, IL12, IL18, IL21, IL23, IL 33, TNFα, TNFβ, IFNα, and IFNβ, and the extracellular domain is selected from the group consisting of an extracellular domain of the receptor of IL15, IL2, IL7, IL6, IL12, IL18, IL21, IL23, IL 33, TNFα, TNFβ, IFNα, and IFNβ.

16. The isolated nucleic acid, the population of CAR cells, the pharmaceutical composition, or the method of one of embodiments 1-14, wherein the fusion protein comprises the inflammatory cytokine, a linker, a transmembrane domain, and a cytoplasmic domain, wherein the transmembrane domain is selected from the group consisting of a transmembrane domain of a receptor of CD4, CD8, CD28, CD27, CD25, CD137, PD1 and PDL1, and the cytoplasmic domain is selected from the group consisting of a cytoplasmic domain of a receptor of CD4, CD8, CD28, CD27, CD25, CD137, PD1, and PDL1.

17. The isolated nucleic acid, the population of CAR cells, the pharmaceutical composition, or the method of one of embodiments 15 and 16, wherein the link is a GS linker.

18. The isolated nucleic acid, the population of CAR cells, the pharmaceutical composition, or the method of one of embodiments 1-9, wherein expression of the additional nucleic acid sequence is regulated by a conditional expression system such that the therapeutic agent is expressed in response to binding of a target antigen.

19. The isolated nucleic acid, the population of CAR cells, the pharmaceutical composition, or the method of one of embodiments 1-18, wherein expression of the additional nucleic acid sequence is regulated by SynNotch polypeptide.

20. The modified cell or the method of one of embodiments 12-19, wherein the modified cell or the T cells comprise an additional CAR binding a solid tumor antigen, and the CAR binds an antigen of a white blood cell.

21. The isolated nucleic acid, the population of CAR cells, the pharmaceutical composition, the modified cell, or the method of one of embodiments 1-20, wherein the modified cell or the T cells comprise a dominant negative PD-1.

22. The isolated nucleic acid, the population of CAR cells, the pharmaceutical composition, the modified cell, or the method of one of embodiments 1-20, wherein the modified cell or the T cells comprise a modified PD-1 lacking a functional PD-1 intracellular domain.

23. The isolated nucleic acid, the population of CAR cells, the pharmaceutical composition, the modified cell, or the method of one of embodiments 1-22, wherein the CAR comprises an extracellular domain, a transmembrane domain, and an intracellular domain, and the extracellular domain binds an antigen.

24. The isolated nucleic acid, the population of CAR cells, the pharmaceutical composition, the modified cell, or the method of one of embodiments 1-23, wherein the intracellular domain comprises a costimulatory signaling region that comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and a combination thereof.

25. The isolated nucleic acid, the population of CAR cells, the pharmaceutical composition, the modified cell, or the method of embodiment 23, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

26. The isolated nucleic acid, the population of CAR cells, the pharmaceutical composition, the modified cell, or the method of one of embodiments 1-25, wherein nucleic acid encoding the therapeutic agent is present in the modified cell in a recombinant DNA construct, in an mRNA, or in a viral vector.

27. The isolated nucleic acid, the population of CAR cells, the pharmaceutical composition, the modified cell, or the method of one of embodiments 1-26, wherein the modified cell comprises an mRNA encoding the therapeutic agent, and the mRNA is not integrated into the genome of the modified cell.

28. The isolated nucleic acid, the population of CAR cells, the pharmaceutical composition, the modified cell, or the method of one of embodiments 1-27, wherein the modified cell comprises a nucleic acid sequence comprising or the isolated nucleic acid comprises a promoter comprising a binding site for a transcription modulator that modulates the expression and/or secretion of the therapeutic agent in the cell.

29. The isolated nucleic acid, the population of CAR cells, the pharmaceutical composition, the modified cell, or the method of embodiment 28, wherein the transcription modulator is or includes Hif1a, NFAT, FOXP3, and/or NFkB.

30. The isolated nucleic acid, the population of CAR cells, the pharmaceutical composition, the modified cell, or the method of embodiment 28, wherein the promoter is responsive to the transcription modulator.

31. The isolated nucleic acid, the population of CAR cells, the pharmaceutical composition, the modified cell, or the method of embodiment 28, wherein the promoter is operably linked to the nucleic acid sequence encoding the therapeutic agent such that the promoter drives expression and/or secretion of the therapeutic agent in the cell.

32. The isolated nucleic acid, the population of CAR cells, the pharmaceutical composition, the modified cell, or the method of one of embodiments 1-26, wherein expression of the therapeutic agent is regulated by an inducible gene expression system.

33. The isolated nucleic acid, the population of CAR cells, the pharmaceutical composition, the modified cell, or the method of embodiment 32, wherein the inducible gene expression system comprises or is a lac system, a tetracycline system, or a galactose system.

34. The isolated nucleic acid, the population of CAR cells, the pharmaceutical composition, the modified cell, or the method of embodiment 32, wherein the inducible gene expression system comprises or is a tetracycline system.

35. The isolated nucleic acid, the population of CAR cells, the pharmaceutical composition, the modified cell, or the method of embodiment 32, wherein the inducible gene expression system comprises or is a tetracycline on a system, and an inducer corresponding to the inducible gene expression system is tetracycline, doxycycline, or an analog thereof.

36. A method of enhancing the expansion of cells (e.g., T cells, NK cells, or macrophages) in a subject, or treating the subject having cancer, the method comprising:
administering an effective amount of a composition to the subject having a form of cancer expressing a tumor antigen, the composition comprising a first population of cells comprising a first CAR binding a first antigen, and a second population of cells comprising the therapeutic agent and the binding molecule that binds a second antigen listed in embodiment 7, wherein the second antigen is a tumor antigen and is different from the first antigen.

37. The method of embodiment 36, wherein the first antigen is CD19, CD22, CD20, BCMA, CDS, CD7, CD2, CD16, CD56, CD30, CD14, CD68, CD11 b, CD18, CD169, CD1c, CD33, CD38, CD138, or CD13, and/or the solid tumor antigen is tMUC 1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC15, SLC6A3, KISS1R, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, B7-H3, or EGFR.

38. A method of increasing proliferative and/or reconstitutive capacities of T cells, the method comprising: providing a T cell; and modulating expression of one or more genes of a T cells, wherein the one or more genes comprise LEF1, CXCR3, FRC, T-bet, PI3K, ezh2, PDCD1, Gfi1, Flt3, FAO, GATA3, Akt, kiaa1324, PDL1, δEF1/ZEB, Kit, Hif-1a Blimp-1, mTOR, fn1, PDL2, FPFIkaros, IL-7R, Hif-2a Myc, Wnt, ITGA9, CTLA4, KLF2, IL-4R, VhI HIF1, Notch1, SMDPD3A, LRBA, HEB, IL-9R PHD1 c-Myb, Notch2, ITPRIPL2, LAG3, MAZR, PDGFRb, PHD2 members of the E2A/HEB family, Activin, PRSS23, Tim3, Tox, gc (Il2rg, PHD3 members of the Ikaros family, BMP, CLECL1, BILA, PU.1, IL-2Ra (CD25) FIH1 Ets-family transcription factor PU.1, TGFb, TBX21, CD160, HES1,2,3, IL-2Rb TET2, Runx1, IL7, IKZF2, 2B4, Sox4, PDGFRa, TET1, GATA-2, IL7Ra, EOMES, Foxp3, E12, Pdgfa, TET3, TCF-1 (Tcf7) IL12, PRDM1, ccr4, E2-2 Pdgfb, DNMT3a, RBPSuh IL15, BTLA, PVRIG, E47, Pdgfc, DNMT3b, Id3, IL6, CD244, CD166, MEF2, Pdgfd, DNMT3c, 1d2, IL2, KL6, SIVA1, Nur77/Nor1, TGF-b1, Runx1, MAPK, JUNB, CD33, Ncoa4, TGF-b2 Runx3, AMPK, FOSB, LAGLS9, Basp2, TGF-b3 EBF, NF-Kb, FAM13A, CD122, Pitx1, BMP2, Pax5, NF-AT, BATF3, IDO1, Prdm16, BMP4, FOG-1, AP-1, KLRC1, IDO2, Ndn, BMP7, GATA-3, PI-3 kinase, Akt/PKB, and Ras/MAP, KLRC2, CD45, Irf6, ActivinbetaA, GATA-2, CCR7, ZNF704, CVPLBL, Dach1, ALK-5, GATA-1 STAT1, CTHRC1, TNFAIP8L2, Nr4a2, BMPR-1A/B, Groucho/TLE/Grg family proteins or Sin3A, STAT2, FAXC, DNMT3A, Hoxa5, BMPR-II, Helios, STAT3, EGR1, CEACAM-1, Hoxb5, TLR, NFAT, STAT4, RBM47, RUNX3, FoxN1, MyD88, Bcl-6, STAT5, ENTPD1, LEXM, Gli1,2,3, SHH, BCL-6b (BAZF), glut1, SUV39H1, PILRA, Smoothen, HIF1, AKAP5, PTNNS1L3, Ptch1, c-Myc, β-catenin, Fegr3a, Fu, IRF4, PI3K, Nat8, Su(fu), NF-kb, GLUL, cc19, Wnt1,3,4,5b, 10b, ThPOK, FAXC, HCK, Smad, Oct3/4, TREM2, CXCL10, Nanog, LNGM, CCL6, CXCL9, Sox2, NUDT16, CD36, INFa,b, KLF4, IGF1, CXCR3, FOXO1, CTSS, CCL5, TSC1, GZMC, CCR5, OxPhos, BATF, CCR7, Zbtb32, CXCL2, SOCS1, E2F2, TNFAIP8L3, SOCS2, SMART, IL-1b, SOCS3, NCOR, IL-1a, SOCS4, TRPV1, SOCS5, TRPV2, SOCS6, TRPV3, SOCS7, TRPV4, CIS, Rgs1, CCR1, PLSCR1, CCR2, ITGB1, CCR3, ITGB2, CCR4, C3AR1, GPCR75, ITGA3, IL-6R, ITGA5, GP130, ITGAL, STAT3, CARD11, MCL1, CD83, PIM-1, CXCL1, CXCL2, CXCR1, CXCR2, CXCR4, IL-1b, or IL-1bR.

39. The method of embodiment 38, wherein the proliferative and/or reconstitutive capacities of T cells are measured based on the expression of one or more markers of T cells.

40. The method of embodiment 39, wherein the expression of the one or more markers of T cells without the presence of an antigen that the T cell recognizes is greater or lower than the expression of the same marker of T cells whose corresponding gene is not modulated and the one or more markers are provided in Table 3 below.

TABLE 3

| Markers | Expression level |
|---|---|
| CD45RO | lower |
| CCR7 | greater |
| CD45RA | greater |
| CD62L | greater |
| CD27 | greater |
| CD28 | greater |
| IL-7Rα | greater |
| CD95 | greater |
| IL-2Rβ | greater |
| CXCR3 | greater |
| LFA-1 | greater |
| CD25 | lower |
| KLRG1 | lower |

41. The method of embodiment 39, wherein the expression of the one or more markers of the T cell in response to the presence of an antigen that the T cell recognizes is greater or lower than the expression of the same marker of T cells whose corresponding gene is not modulated and the one or more markers are provided in Table 4 below.

TABLE 4

| Markers | Expression level |
|---|---|
| CD25 | lower |
| CD69 | lower |
| CD107α | lower |
| CD137 | lower |
| CD40L | lower |
| OX40 | lower |
| CD27 | greater |
| CD28 | greater |
| Erk phosphorylation | lower |
| Akt phosphorylation | lower |

42. The method of embodiment 46, wherein the proliferative and/or re-constitutive capacities of T cells are measured based on release and/or expression of one or more proteins of the T cells.

43. The method of embodiment 42, wherein the one or more proteins are one or more cytokines released and/or expressed by the T cells.

44. The method of embodiment 48, wherein the release and/or expression of one or more cytokines by the T cells in response to the presence of an antigen that the T cell recognizes is greater or lower than the expression of the same marker of T cells whose corresponding gene is not modulated and the one or more markers are provided in Table 5 below.

TABLE 5

| Markers | Expression level |
| --- | --- |
| IL2 | lower |
| IL4 | lower |
| IL6 | lower |
| IL10 | lower |
| TNFα | lower |
| IFNγ | lower |

45. A method to enhance inhibitory capacities of T cells on tumor cells, the method comprising: providing a T cell; and
modulating the expression of one or more genes of T cells, which are provided in Table 1.
46. The method of embodiment 45, wherein the inhibitory capacities of T cells are measured based on the expression of one or more markers of the T cells.
47. The method of embodiment 46, wherein the expression of the one or more markers of the T cell without the presence of an antigen that the T cell recognizes is greater or lower than the expression of the same marker of T cells whose corresponding gene is not modulated and the one or more markers are provided in Table 6 below.

TABLE 6

| Markers | Expression level |
| --- | --- |
| CD45RO | greater |
| CCR7 | lower |
| CD45RA | lower |
| CD62L | lower |
| CD27 | lower |
| CD28 | lower |
| IL-7Rα | lower |
| CD95 | lower |
| IL-2Rβ | lower |
| CXCR3 | lower |
| LFA-1 | lower |
| CD25 | greater |
| KLRG1 | greater |

48. The method of embodiment 46, wherein the expression of the one or more markers of the T cell in response to the presence of an antigen that the T cell recognizes is greater or lower than the expression of the same marker of T cells whose corresponding gene is not modulated and the one or more markers are provided in Table 7 below.

TABLE 7

| Markers | Expression level |
| --- | --- |
| CD25 | greater |
| CD69 | greater |
| CD107α | greater |
| CD137 | greater |
| CD40L | greater |
| OX40 | greater |
| CD27 | lower |
| CD28 | lower |
| Erk phosphorylation | greater |
| Akt phosphorylation | greater |

49. The method of embodiment 46, wherein the proliferative and/or reconstitutive capacities of T cells are measured based on release and/or expression of one or more proteins of the T cells.
50. The method of embodiment 49, wherein the one or more proteins are one or more cytokines released and/or expressed by the T cells.
51. The method of embodiment 50, wherein the release and/or expression of one or more cytokines by the T cells in response to the presence of an antigen that the T cell recognizes is greater or lower than the expression of the same marker of T cells whose corresponding gene is not modulated and the one or more markers are provided in Table 7 below.

TABLE 8

| Markers | Expression level |
| --- | --- |
| IL2 | greater |
| IL4 | greater |
| IL6 | greater |
| IL10 | greater |
| TNFα | greater |
| IFNγ | greater |

52. The method of any one of embodiments 38-51, wherein the T cells comprise an antigen binding receptor that is a T cell receptor (TCR) or chimeric antigen receptor (CAR).
53. The method of embodiment 52, wherein the T cells comprise a chimeric antigen receptor (CAR), or the isolated nucleic acid comprises a nucleic acid sequence encoding the CAR.
54. The method of embodiment 53, wherein the CAR comprises an extracellular domain, a transmembrane domain, and an intracellular domain, and the extracellular domain binds an antigen.
55. The method of embodiment 54, wherein the intracellular domain comprises a costimulatory signaling region that comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, or a combination thereof.
56. The method of embodiment 54, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.
57. The method of embodiment 52, wherein the modified cell comprises a modified T Cell Receptor (TCR), or the isolated nucleic acid comprises a nucleic acid sequence encoding the modified TCR.
58. The method of embodiment 57, wherein the TCR is derived from spontaneously occurring tumor-specific T cells in patients.
59. The method of embodiment 57, wherein the TCR binds to a tumor antigen.
60. The method of embodiment 57, wherein the tumor antigen comprises CEA, gp100, MART-1, p53, MAGE-A3, or NY-ESO-1.

61. The method of embodiment 57, wherein the TCR comprises TCRγ and TCRδ chains or TCRα and TCRβ chains, or a combination thereof.
62. A modified lymphocyte comprising a greater or lower expression of one or more genes listed in Table 1 as compared to a wild type lymphocyte.
63. The modified lymphocyte of embodiment 62, wherein the modified lymphocyte comprises the antigen recognizing receptor of one of embodiments 15-26.
64. A pharmaceutical composition comprising a population of the lymphocytes of embodiment 63.
65. A method of treating a condition in a subject in need thereof and/or treating a tumor of the subject, the method comprising administering an effective amount of the composition of embodiment 64 to the subject.
66. A modified cell comprising an antigen binding molecule, wherein expression or function of an endogenous gene associated with T cell apoptosis has been reduced or eliminated.
67. The modified cell of embodiment 66, wherein the gene comprises at least one of CD80, Fas, Bcl-2, Bax, PI3K, AKT, C-jun, C-fos, C-myc, Gata3, Tox, Mt2, or Pdcd4.
68. A modified cell comprising an antigen binding molecule, wherein expression or function of one or more transcription factors playing roles in innate immune responses has been increased or enhanced.
69. The modified cell of embodiment 68, wherein the gene comprises at least one of IRF7, IRF3, ILC3s, or RNF2.
70. A modified cell comprising an antigen binding molecule, wherein expression or function of CD80 has been reduced or eliminated.
71. The modified cell of embodiment 70, wherein the expression or function of PD1 has been reduced or eliminated.
72. A modified cell comprising an antigen binding molecule, wherein expression or function of IRF3 and/or IRF7 has been increased or enhanced.
73. The modified cell of one of embodiments 67-72, wherein the antigen binding molecule comprises a chimeric antigen receptor (CAR) and/or a second antigen binding molecule is a T Cell Receptor (TCR).
74. The modified cell of embodiment 73, wherein the antigen binding molecule is the CAR comprising an extracellular domain, a transmembrane domain, and an intracellular domain, and the extracellular domain binds an antigen.
75. The modified cell of embodiment 74, wherein the intracellular domain comprises a costimulatory signaling region that comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, or a combination thereof.
76. The modified cell of embodiment 74, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.
77. The modified cell of embodiment 73, wherein the antigen binding molecule is a modified TCR.
78. The modified cell of embodiment 77, wherein the TCR is derived from spontaneously occurring tumor-specific T cells in patients.
79. The modified cell of embodiment 77, wherein the TCR binds to a tumor antigen.
80. The modified cell of embodiment 79, wherein the tumor antigen comprises CEA, gp100, MART-1, p53, MAGE-A3, or NY-ESO-1.
81. The modified cell of embodiment 79, wherein the TCR comprises TCRγ and TCRδ chains or TCRα and TCRβ chains, or a combination thereof.
82. The modified cell of one of embodiments 66-81, wherein the cell is a T cell, a dendritic cell, an NK cell, or a macrophage cell.
83. The modified cell of one of embodiments 66, 67, 70, 71, or 73-82, wherein the cell has a disruption in an endogenous gene associated with a biosynthesis or transportation pathway of CD80 and reduced expression of CD80 as compared to the corresponding wild type of the cell.
84. The modified cell of embodiment 83, wherein the disruption is caused by a nuclease, siRNA, and/or shRNA.
85. The modified cell of embodiment 83, wherein the disruption is caused by a zinc finger nuclease (ZFN).
86. The modified cell of embodiment 83, wherein the disruption is caused by a CRISPR associated protein 9 (Cas9).
87. The modified cell of embodiment 83, wherein the disruption is caused by a Transcription activator-like effector nuclease (TALEN).
88. The modified cell of any of embodiments 66, 67, 70, 71, or 73-82, wherein the cell has a nucleic acid sequence encoding modified CD80 that lacks a functional intracellular domain as compared to the corresponding wild-type receptor.
89. The modified cell of embodiment 88, wherein the modified CD80 is a dominant negative variant of CD80 such that the cell has an altered molecular function of CD80, and/or the modified PD1 is a dominant negative variant of PD1 such that the cell has an altered molecular function of PD1.
90. The cell of embodiment 88, wherein the modified CD80 is or comprises the amino acid sequence SEQ ID NO: 116 or is a truncated CD80 having the amino acid sequence SEQ ID NO: 114 without the intracellular domain of CD80.
91. The modified cell of one of embodiments 68, 69, or 72-82, wherein the gene is IRF7.
92. The modified cell of embodiment 91, wherein the IRF7 is overexpressed as compared to its expression in a corresponding wild type cell.
93. The modified cell of embodiment 91, wherein the genome of the cell comprises a polynucleotide sequence encoding IRF7, the polynucleotide sequence operably linked to a promoter.
94. The modified cell of embodiment 91, wherein the genome of the cell comprises a polynucleotide sequence encoding IRF7, the polynucleotide sequence operably linked to a promoter such as NFAT.
95. A pharmaceutical composition comprising the population of the CAR cells of one of embodiments 67-94.

96. A method of causing or promoting T cell response in a subject in need thereof and/or treating a tumor of the subject, the method comprising administering an effective amount of the composition of embodiment 95 to the subject.

97. The isolated nucleic acid, the modified T cell or the method of any preceding suitable embodiments, wherein the cell or modified cell is a T cell derived from a healthy donor or a subject having cancer, and the modified T cell comprises a dominant negative form of a receptor associated with an immune checkpoint inhibitor.

98. The isolated nucleic acid, the modified T cell or the method of any preceding suitable embodiments, wherein the immune checkpoint inhibitor is selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRI), natural killer cell receptor 2B4 (2B4), and CD 160.

99. The isolated nucleic acid, the modified T cell, or the method of embodiment 98, wherein immune checkpoint inhibitor is modified PD-1.

100. The isolated nucleic acid, the modified T cell or the method of embodiment 98, wherein the modified PD-1 lacks a functional PD-1 intracellular domain for PD-1 signal transduction, interferes with a pathway between PD-1 of a human T cell and PD-L1 of a certain cell, comprises or is a PD-1 extracellular domain or a PD-1 transmembrane domain, or a combination thereof, or a modified PD-1 intracellular domain comprising a substitution or deletion as compared to a wild-type PD-1 intracellular domain, or comprises or is a soluble receptor comprising a PD-1 extracellular domain that binds to PD-L1 of a certain cell.

101. The isolated nucleic acid, the modified T cell or the method of embodiment 98, wherein an inhibitory effect of PD-L1 on cytokine production of the human T cells of the population is less than an inhibitory effect of PD-L1 on cytokine production of human T cells that do not comprise at least a part of the nucleic acid sequence that encodes the modified PD-1.

102. The isolated nucleic acid, the modified T cell, or the method of any preceding suitable embodiments, wherein the modified T cell is engineered to express and secrete a therapeutic agent such as a cytokine or a small protein.

103. The isolated nucleic acid, the modified T cell or the method of embodiment 102, wherein the therapeutic agent that is or comprises IFN-γ.

104. The isolated nucleic acid, the modified T cell, or the method of embodiment 102, wherein the therapeutic agent is or comprises at least one of IL-6 or IFN-γ, IL-17, or CCL19.

105. The isolated nucleic acid, the modified T cell, or the method of embodiment 102, wherein the therapeutic agent that is or comprises IL-15 or IL-12, or a combination thereof.

106. The isolated nucleic acid, the modified T cell, or the method of embodiment 102, wherein the small protein or the therapeutic agent is or comprises a recombinant or native cytokine.

107. The isolated nucleic acid, the modified T cell, or the method of embodiment 102, wherein the therapeutic agent comprises an FC fusion protein associated with a small protein.

108. The isolated nucleic acid, the modified T cell or the method of embodiment 102, wherein the small protein is or comprises IL-12, IL-15, IL-6, or IFN-γ.

109. The isolated nucleic acid, the modified T cell, or the method of embodiment 102, wherein the therapeutic agent is regulated by Hif1a, NFAT, FOXP3, and/or NFkB.

110. The isolated nucleic acid, the modified T cell or the method of embodiment 102, wherein the small protein or the therapeutic agent is or comprises two or more recombinant or native cytokines are collected via 2A or /IRES component.

111. The isolated nucleic acid, the modified T cell, or the method of any preceding suitable embodiments, wherein the modified T cell comprises a first targeting vector and a second targeting vector, the first targeting vector comprising a nucleic acid sequence encoding a CAR binding a blood antigen and encoding the therapeutic agent, and the second targeting vector comprises a nucleic acid sequence encoding a CAR binding solid tumor antigen and encoding a dominant-negative form of the immune checkpoint molecule.

112. The isolated nucleic acid, the modified T cell or the method of any preceding suitable embodiments, wherein the modified T cell comprises a first targeting vector and a second targeting vector, the first targeting vector comprising a nucleic acid sequence encoding a CAR binding CD19 and encoding the therapeutic agent, and the second targeting vector comprise a nucleic acid sequence encoding a CAR binding UPK2, ACPP, SIGLEC15 or KISS1R and encoding a dominant negative form of PD-1.

113. The isolated nucleic acid, the modified T cell, or the method of any preceding suitable embodiments, wherein the modified T cell comprises a first targeting vector and a second targeting vector, the first targeting vector comprising a nucleic acid sequence encoding a CAR binding a blood antigen, and the second targeting vector comprises a nucleic acid sequence encoding a CAR binding solid tumor antigen.

114. The isolated nucleic acid, the modified T cell, or the method of any preceding suitable embodiments, wherein the modified T cell comprises a first targeting vector and a second targeting vector, the first targeting vector comprising a nucleic acid sequence encoding a CAR binding a B cell antigen, and the second targeting vector comprises a nucleic acid sequence encoding a CAR binding solid tumor antigen.

115. The isolated nucleic acid, the modified T cell, or the method of embodiment 114, wherein the solid tumor antigen is at least one of antigens listed in Table 1, and/or the B cell antigen is CD19, CD20, CD22, or BCMA.

116. The isolated nucleic acid, the modified T cell, or the method of embodiment 114, wherein the solid tumor antigen comprises at least one of antigens listed in Table 1.

117. A method of enhancing T cell expansion in a subject in need thereof, wherein the method comprising administering an effective amount of the composition of T cells of any preceding suitable embodiments to the subject, the subject having a higher level of T cell expansion as compared with a subject that is administered an effective amount of the CAR T cells that do not have the CAR binding the B cell antigen.

118. The isolated nucleic acid, the modified T cell, or the method of any preceding suitable embodiments, wherein the modified T cell comprises a nucleic acid sequence encoding hTERT, SV40LT, or a combination thereof.

119. The isolated nucleic acid, the modified T cell, or the method of embodiment 118, wherein the modified T cell is more proliferable than T cells without the nucleic acid.

120. The isolated nucleic acid, the modified T cell, or the method of embodiment 119, wherein the proliferable T cell retains functions of normal T cells/CAR T cells such as cell therapy functions.

121. The isolated nucleic acid, the modified T cell or the method of embodiment 119, wherein the T cell comprises a CAR and is cultured in the presence of an agent that is recognized by the extracellular domain of the CAR, thereby producing a modified CAR cell.

122. The isolated nucleic acid, the modified T cell or the method of any preceding suitable embodiments, wherein integration of the nucleic acid encoding hTERT, the nucleic acid encoding SV40LT, or a combination thereof includes genomic integration of the nucleic acid encoding hTERT, a nucleic acid encoding SV40LT, or a combination thereof and constitutive expression of hTERT, SV40LT, or a combination thereof.

123. The isolated nucleic acid, the modified T cell or the method of any preceding suitable embodiments, wherein expression of hTERT, SV40LT, or a combination thereof, is regulated by an inducible expression system such as a rtTA-TRE system.

124. The isolated nucleic acid, the modified T cell, or the method of any preceding suitable embodiments, wherein the modified T cell comprises a nucleic acid sequence encoding a suicide gene such as an HSV-TK system.

125. The isolated nucleic acid, the modified T cell, or the method of any preceding suitable embodiments, wherein the cell has a reduced graft-versus-host disease (GVHD) response in a bioincompatible human recipient as compared to the GVHD response of the primary human T cell.

126. The isolated nucleic acid, the modified T cell, or the method of any preceding suitable embodiments, wherein the cell has reduced expression of endogenous TRAC gene.

The related sequences are provided in Innovative Cellular Therapeutics' PCT Patent Applications Nos: PCT/CN2016/075061, PCT/CN2018/08891, and PCT/US19/13068, which are incorporated as a reference herein,

EXAMPLES

Lentiviral vectors that encode individual CAR molecules were generated and transfected into T cells, which are described below. Techniques related to cell cultures and construction of cytotoxic T lymphocyte assay can be found in "Control of large, established tumor xenografts with genetically retargeted human T cells containing CD28 and CD137 domains," PNAS, Mar. 3, 2009, vol. 106, no. 9, 3360-3365 and "Chimeric Receptors Containing CD137 Signal Transduction Domains Mediate Enhanced Survival of T Cells and Increased Antileukemic Efficacy In Vivo," Molecular Therapy, August 2009, vol. 17, no. 8, 1453-1464, which are incorporated herein by reference in their entirety On day 0, the peripheral blood of healthy volunteers was drawn. CD3+ T cells were sorted with pan T Kit, and CD3/CD28 Dynabeads were added at a 1:1 ratio to stimulate the T cells. On day 1, the T cell were transfected with the vectors listed in Table 9: H19CAR/$10^6$ T cells according to MIO=8.79, H19-bbz-NFAT6x-sFLT3L/$10^6$ T cells according to MOI=46.20, H19bbz-2a-sFLT3L/$10^6$ T cells according to MOI=47.20, and $10^6$ T cells as the control. On day 2, the media were changed, lentivirus and Dynabeads were removed, and the T cells were resuspended and added with fresh media.

TABLE 9

| Cells' Name | Construct Included |
| --- | --- |
| 1234 | h19CAR |
| 7204 | H19-bbz-NFAT6x-sFLT3L |
| 7407 | H19bbz-2a-sFLT3L |

On day 6, CAR expression ratio and cell phenotypes were determined using flow cytometry. Since all three antibodies are humanized antibodies, they were detected with human CAR antibodies. After testing, the non-transduced cells (NT) cells were used to adjust the CAR expression ratio to the level of 48.27%. The experiment was performed according to Table 10. The cells were co-cultured for 24 hours (h), and samples of co-cultured cells were tested using flow staining. The supernatant of the co-cultured cells was collected to detect the expression of FLT3L by ELISA.

TABLE 10

| Experimental design | | | |
| --- | --- | --- | --- |
| | Substrate cell | E:T | system |
| T cell | K562-CD19 | 3:1 | 24-well plate 400 ul x-vivo without IL2 added |
| NT | − | | |
| NT | + | | |
| 1234 | − | | |
| 1234 | + | | |
| 7204 | − | | |
| 7204 | + | | |
| 7407 | − | | |
| 7407 | + | | |

Figure 5:
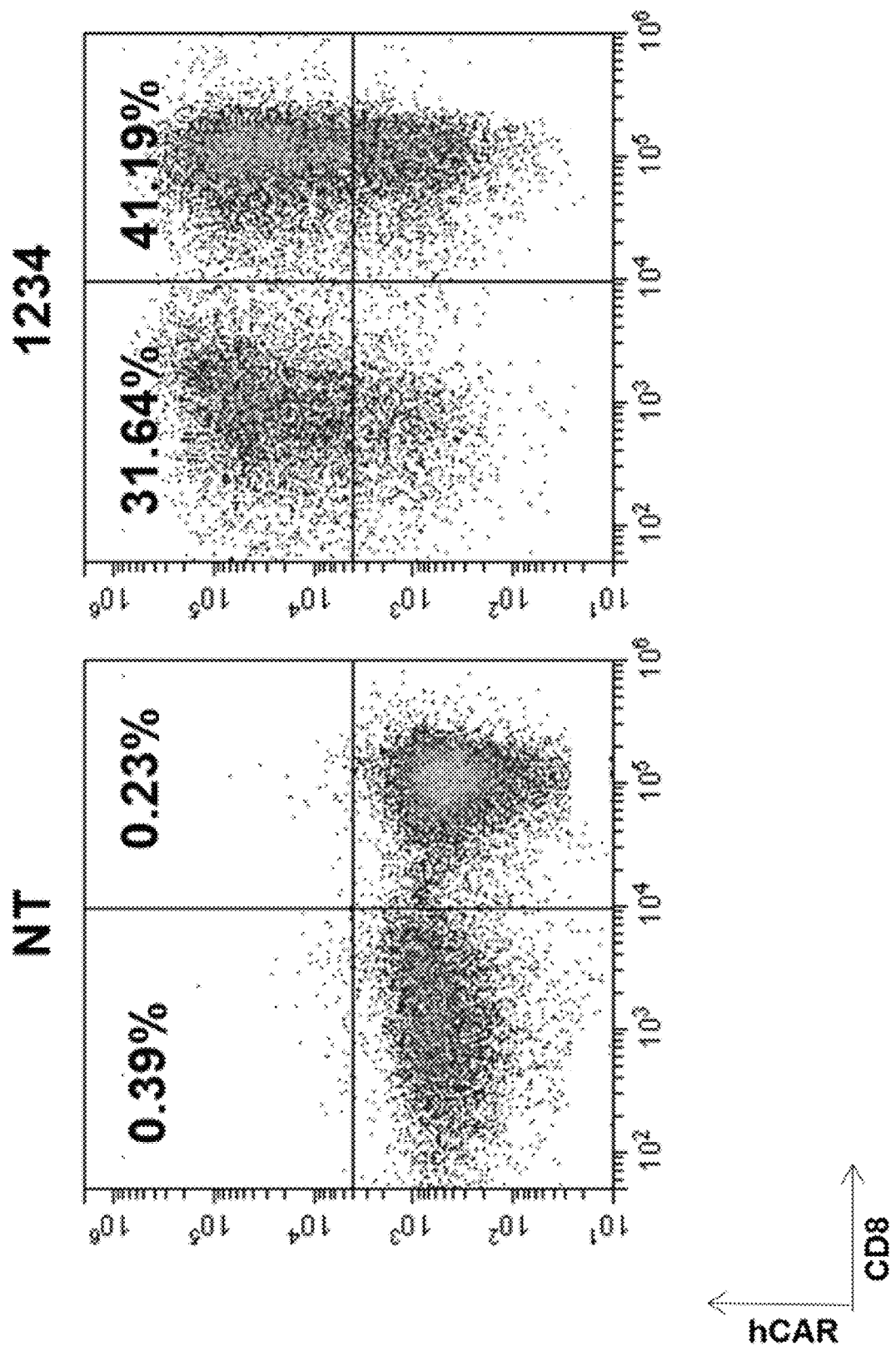
FIGS. 5 and 6 show the expression of the vectors shown in FIG. 4.
Figure 6:
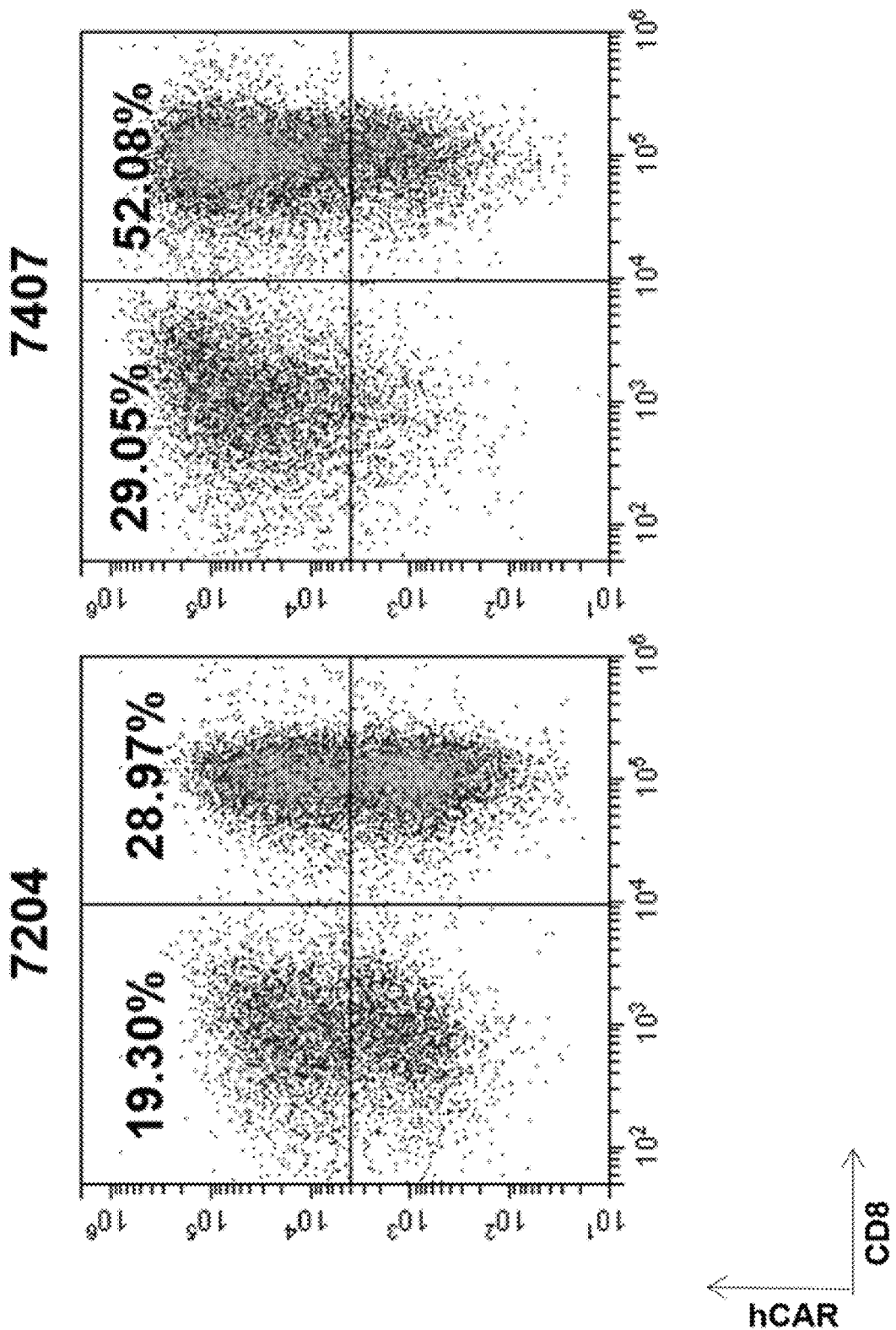
Figure 7:
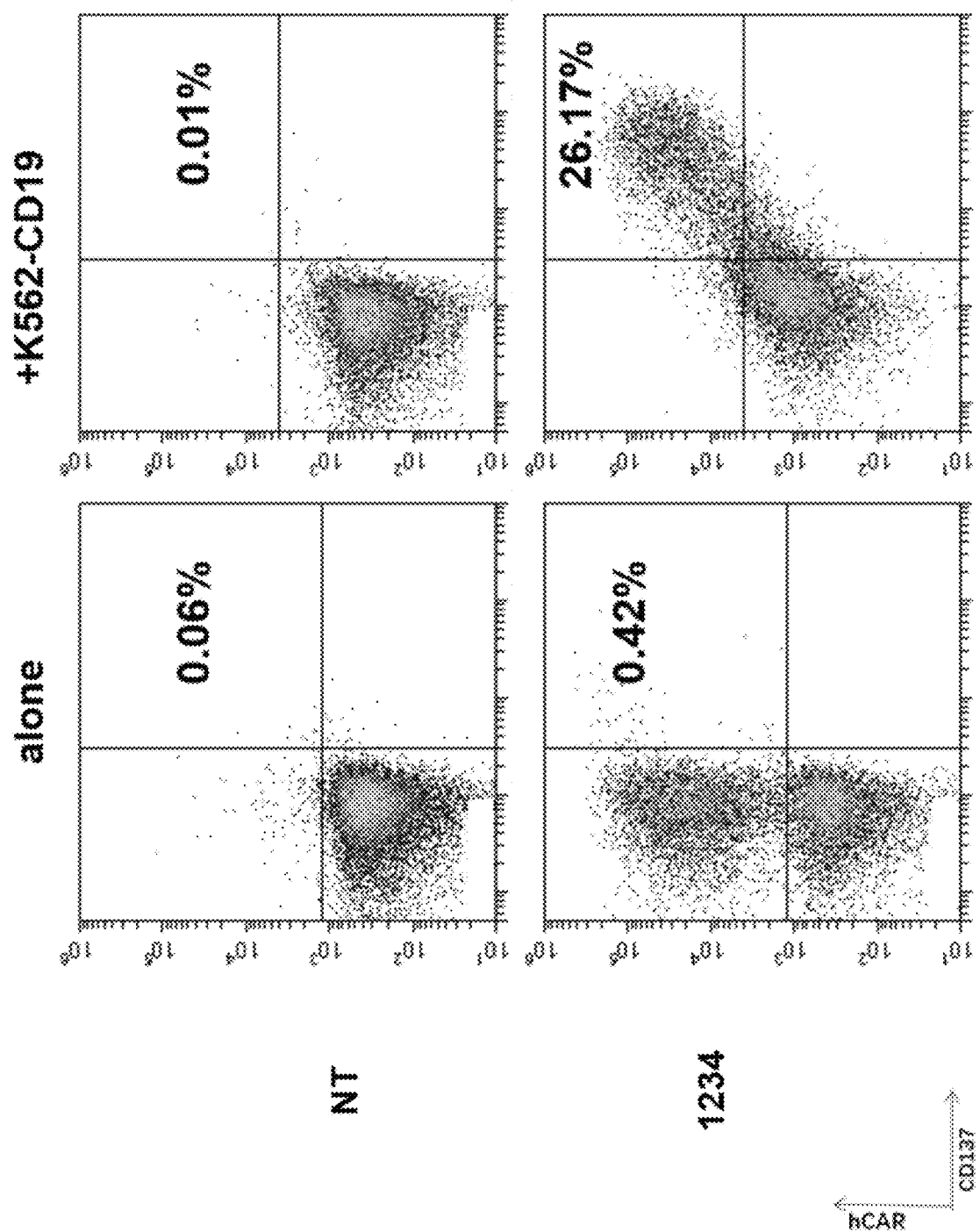
FIGS. 7, 8, 9, 10, and 11 show flow cytometry results of co-cultured CAR T cells and corresponding substrate cells.
Figure 8:
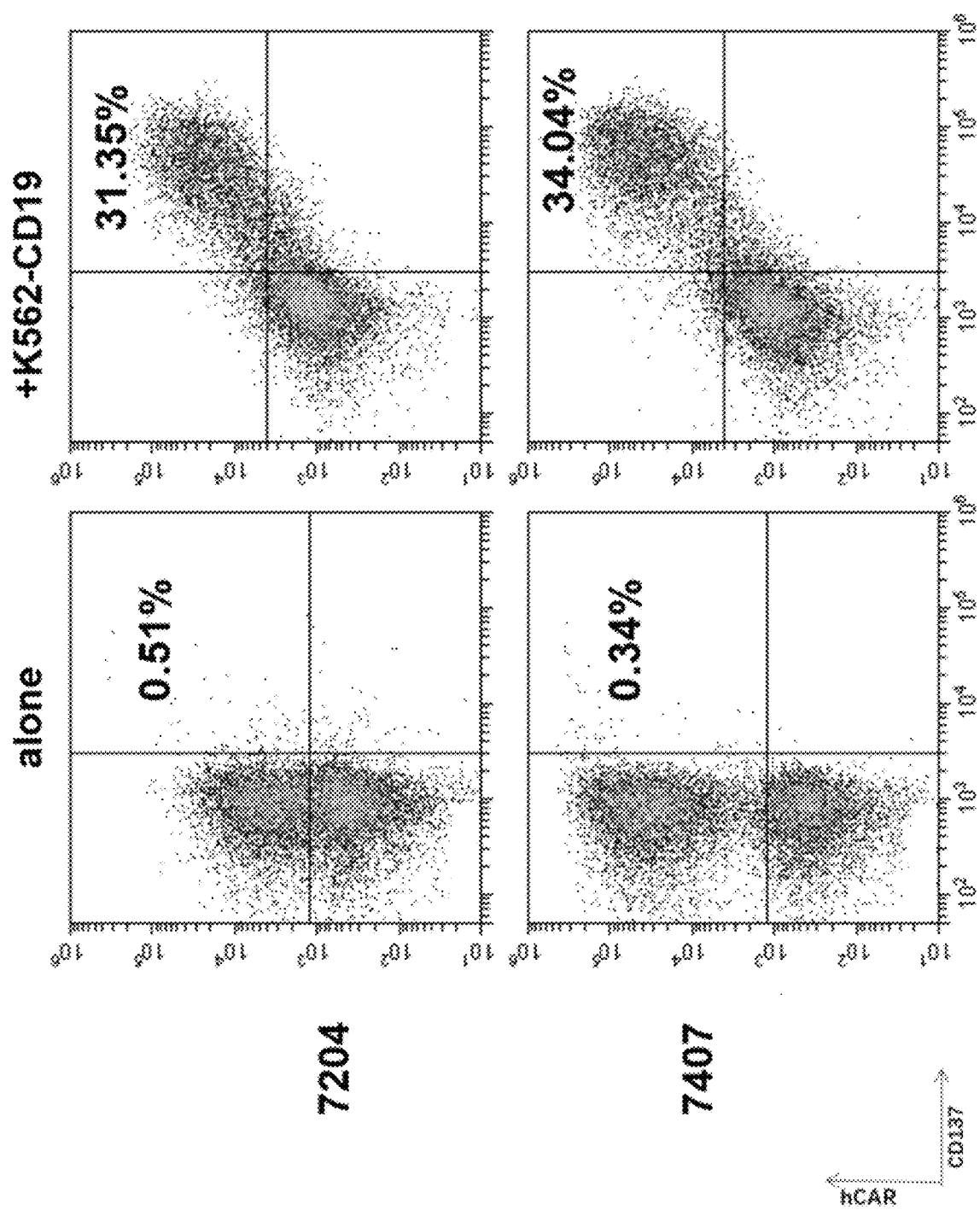
Figure 9:
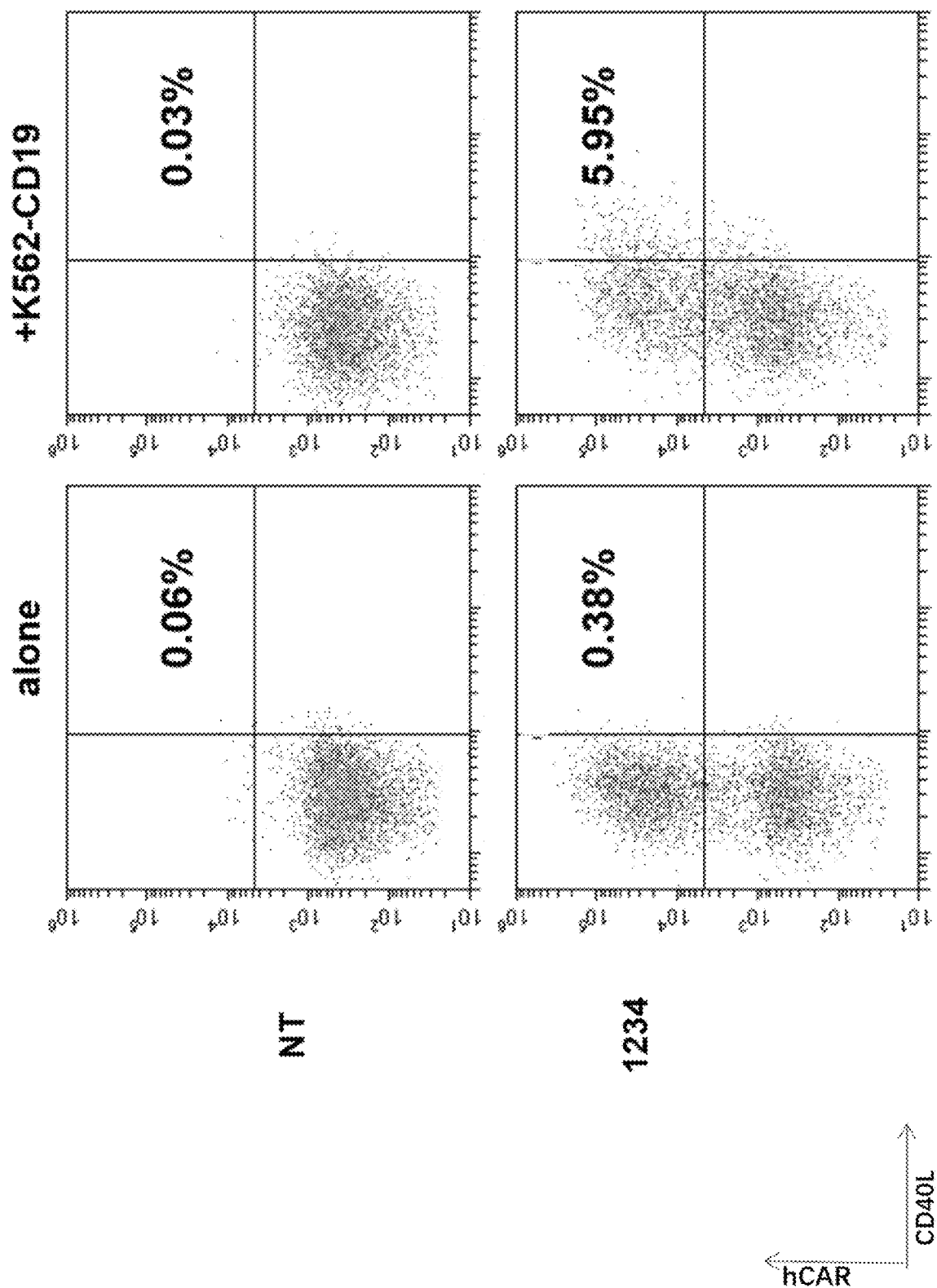
Figure 10:
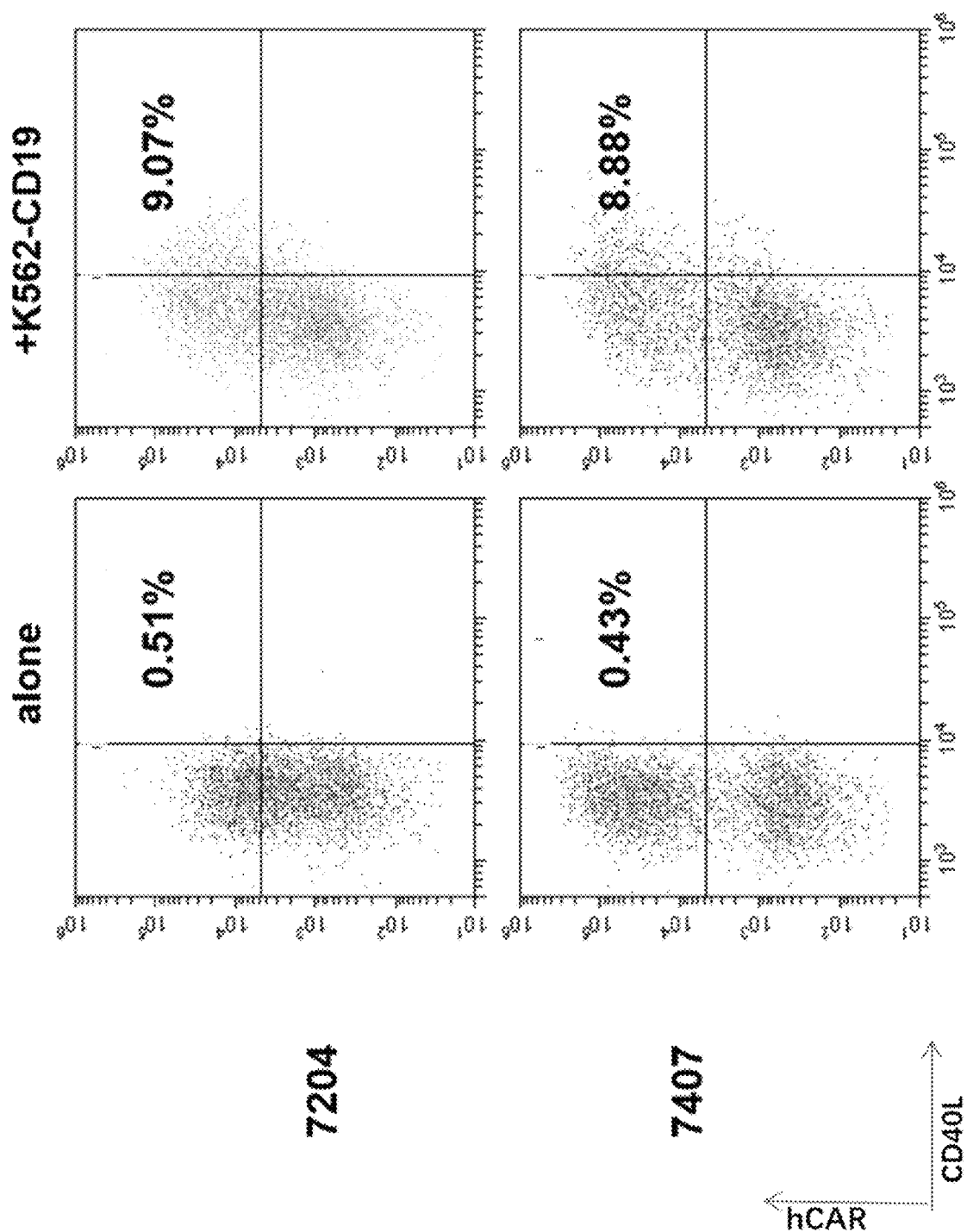
Figure 11:
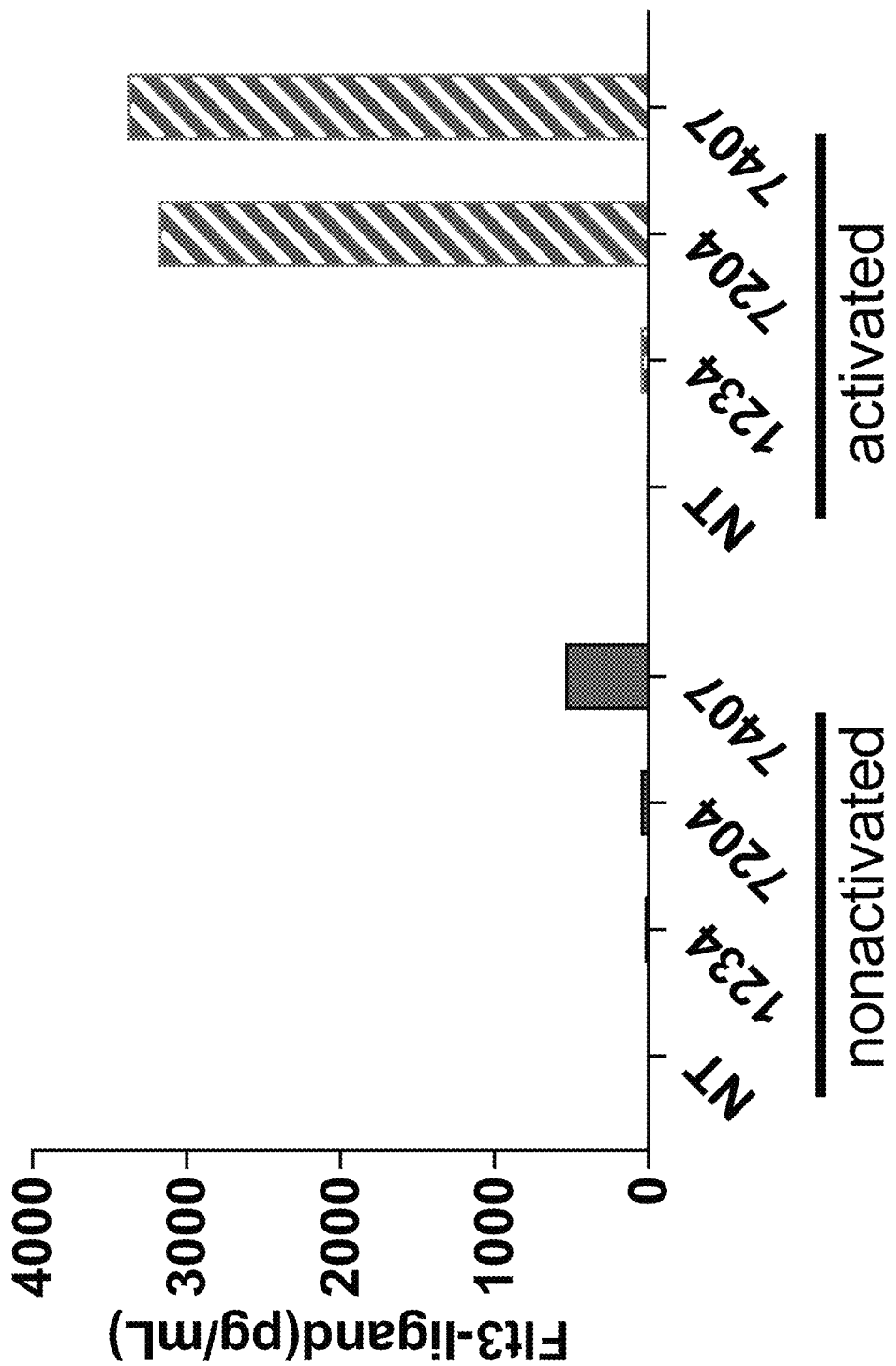
Figure 12:
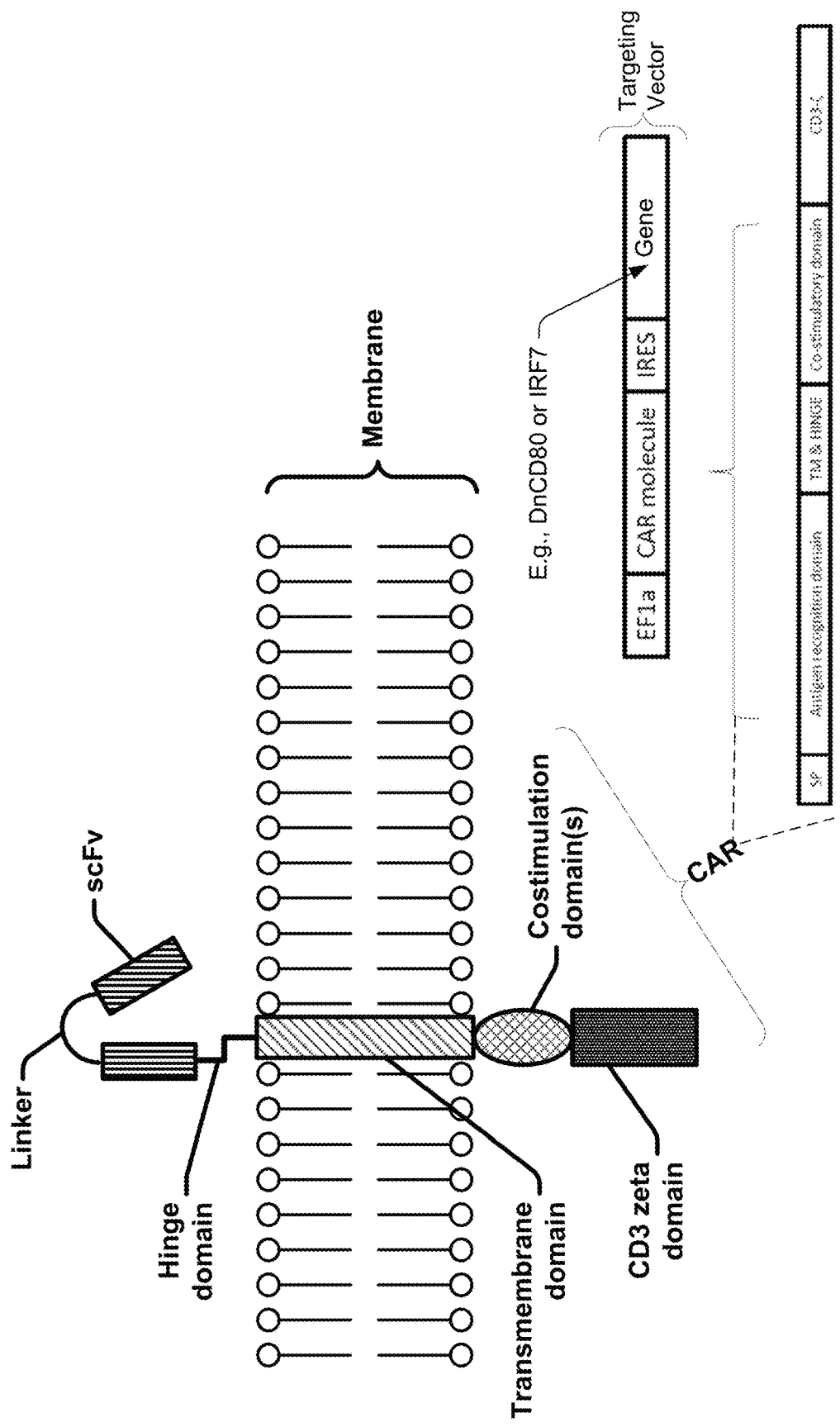
FIG. 12 shows a schematic diagram of an exemplary CAR and a construct of a target gene.

As shown in FIGS. 5 and 6, h19CAR showed 72.83% hCAR expression, H19-bbz-NFAT6x-sFLT3L showed 48.27% hCAR expression, and H19bbz-2a-sFLT3L showed 81.13% hCAR expression in corresponding cell cultures.

CD19-CAR-sFLT3L experimental results showed flow cytometry protein expression of NT cells, 1234 cells, 7204 cells, 7407 cells (See description in Table 9), and co-culture with CD19 positive cells (K562-CD19 cells) for 24 h. The analysis showed that, after co-cultivation for 24 h, K562-CD19 stimulated the expression of CD137 and CD40L in 7024 and 7047-infected T cells relative to the control group without CD19 positive substrate cells. The expression intensity was similar to that of the positive control group 1234.

FIGS. 7-11 showed that the modified CD19-CAR function was not affected, and the up-regulation of CD137 indicates that the cells were in an activated state. The expression of CD40L indicated that this T cell activated other CD40+ immune cells in the body, such as DC cells. Further analysis showed that, after 24 h of co-cultivation, the supernatants of each group of cells were collected, and the expression of sFLT3L was detected by ELISA. 7024 cells released a large amount of sFlt3L upon activation. 7047 cells released a certain amount of sFlt3L when it was not activated, but the release of sFlt3L was more significant after being activated. Through the construction of the two vectors, the release of sFIT3L was controlled in CAR T after activation.

All publications, patents, and patent applications cited in this specification are incorporated herein by reference in their entireties as if each individual publication, patent, or patent application were specifically and individually indicated to be incorporated by reference. While the foregoing has been described in terms of various embodiments, the skilled artisan will appreciate that various modifications, substitutions, omissions, and changes may be made without departing from the spirit thereof.

The invention claimed is:

1. An isolated polynucleotide comprising a polynucleotide encoding a nuclear factor of activated T cells (NFAT) promoter operatively linked to a polynucleotide encoding Fms-related tyrosine kinase 3 ligand (FLT3L), wherein the polynucleotide comprises SEQ ID NO: 133 or 134.

2. The isolated polynucleotide of claim 1, wherein the polynucleotide comprises SEQ ID NO: 133.

3. The isolated polynucleotide of claim 1, wherein the isolated polynucleotide further comprises a nucleic acid encoding amino acid sequence SEQ ID NO: 113 or 114.

4. A vector comprising the isolated polynucleotide of claim 1.

5. A modified cell comprising the isolated polynucleotide of claim 1.

6. The modified cell of claim 5, wherein the modified cell further comprises a modified T cell receptor (TCR) or a chimeric antigen receptor (CAR).

7. The modified cell of claim 6, wherein the TCR is derived from spontaneously occurring tumor-specific T cells in patients, and wherein the TCR binds to a tumor antigen that comprises CEA, gp100, MART-1, p53, MAGE-A3, or NY-ESO-, or the TCR comprises TCRγ and TCRδ chains or TCRα and TCRβ chains, or a combination thereof.

8. The modified cell of claim 6, wherein the CAR comprises an antigen binding domain, a transmembrane domain, and an intracellular domain.

9. The modified cell of claim 8, wherein the antigen binding domain binds to a tumor antigen comprising TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, Lewis Y, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin, PCTA-1/Galectin 8, MelanA/MART1, Ras mutant, sarcoma translocation breakpoints, ML-IAP, ERG (TM-PRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, GUCY2C, or IGLL1.

10. The modified cell of claim 9, wherein the intracellular domain comprises a co-stimulatory signaling domain, or a primary signaling domain and a co-stimulatory signaling domain, wherein the co-stimulatory signaling domain comprises a signaling domain of a protein comprising CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, or NKG2D.

11. The modified cell of claim 5, wherein the modified cell is a T cell, an NK cell or a macrophage.

12. The modified cell of claim 5, wherein the modified cell is engineered to express and secrete a therapeutic agent.

13. The modified cell of claim 12, wherein the therapeutic agent comprises IL-12, IL-6, or IFN-γ.

14. The modified cell of claim 5, wherein the modified cell is derived from a healthy donor or a subject having cancer.

15. The modified cell of claim 5, wherein the modified cell further comprises a CAR targeting a WBC antigen or CAR targeting a solid tumor antigen, or a combination thereof.

16. A population of cells comprising the modified cell of claim 5, wherein the modified cell is a T cell.

17. A pharmaceutical composition comprising the population of cells of claim 16.

18. A method of stimulating an anti-tumor immune response in a subject in need thereof, the method comprising administering an effective amount of the pharmaceutical composition of claim 17 to the subject, thereby stimulating the anti-tumor immune response.

* * * * *